(12) United States Patent
Kondo et al.

(10) Patent No.: US 6,174,456 B1
(45) Date of Patent: *Jan. 16, 2001

(54) LIQUID CRYSTAL COMPOUNDS HAVING SUBSTITUTED ALKYL GROUPS, LIQUID CRYSTAL COMPOSITION AND LIQUID CRYSTAL DISPLAY ELEMENT

(75) Inventors: Tomoyuki Kondo; Kouichi Shibata; Shuichi Matsui; Kazutoshi Miyazawa; Norihisa Hachiya; Etsuo Nakagawa, all of Ichihara (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/981,145

(22) PCT Filed: Jun. 7, 1996

(86) PCT No.: PCT/JP96/01550

§ 371 Date: Dec. 8, 1997

§ 102(e) Date: Dec. 8, 1997

(87) PCT Pub. No.: WO96/41787

PCT Pub. Date: Dec. 27, 1996

(30) Foreign Application Priority Data

Jun. 8, 1995 (JP) .................................................. 7-166802

(51) Int. Cl.[7] .......................... C09K 19/30; C09K 19/12; C09K 19/34; C07C 22/00

(52) U.S. Cl. ................................ 252/299.63; 252/299.66; 252/299.61; 568/671; 570/144

(58) Field of Search ...................... 252/299.61, 299.63, 252/299.66; 570/144; 568/671

(56) References Cited

U.S. PATENT DOCUMENTS

| | | | |
|---|---|---|---|
| 5,382,379 | * 1/1995 | Onji et al. | 252/299.63 |
| 5,578,241 | * 11/1996 | Plach et al. | 252/299.01 |
| 5,653,911 | * 8/1997 | Kondo et al. | 252/299.01 |
| 5,827,450 | * 10/1998 | Numata et al. | 252/299.63 |
| 5,837,162 | * 11/1998 | Reiffenrath et al. | 252/299.63 |
| 5,932,138 | * 8/1999 | Plach et al. | 252/299.66 |

FOREIGN PATENT DOCUMENTS

3237367 * 10/1982 (DE).

* cited by examiner

Primary Examiner—C. H. Kelly
(74) Attorney, Agent, or Firm—Browdy & Neimark

(57) ABSTRACT

The present invention provides liquid crystalline compounds having compatibility with the other liquid crystal materials and having low viscosity and excellent stability, and high transition temperature of the isotropic phase, liquid crystal compositions containing at least one kind of the liquid crystalline compounds, and liquid crystal display devices constituted by using the liquid crystal compositions. The liquid crystalline compounds are represented by the following formula:

$$R-A_1-Z_1-A_2-Z_2-A_3-Z_3-A_4-(CH_2)_m-X \quad (1)$$

wherein R indicates H or an alkyl group having 1 to 10 carbon atoms (one or more methylene group (—$CH_2$—) in the alkyl group may be replaced by —O—, —S—, —CO—, —CH=CH— or —C≡C—, but —O— or —S— are not continuous), m indicates an integer of 1 to 10; X indicates F, Cl, Br, I or OH; $A_1$, $A_2$, $A_3$ and $A_4$, each independently, indicate a trans-1,4-cyclohexylene group, a 1,4-phenylene group in which one or more hydrogen atoms on the ring may be substituted by a fluorine atom, a cyclohexenylenediyl group, a pyrimidine-2,5-diyl group, a pyridine-2,5-diyl group or a 1,3-dioxane-2,5-diyl group; $Z_1$, $Z_2$ and $Z_3$, each independently, indicate —($CH_2$)$_2$— or a covalent bond, and at least two of $Z_1$, $Z_2$ and $Z_3$ indicate covalent bonds.

18 Claims, 1 Drawing Sheet

LIQUID CRYSTAL COMPOUNDS HAVING SUBSTITUTED ALKYL GROUPS, LIQUID CRYSTAL COMPOSITION AND LIQUID CRYSTAL DISPLAY ELEMENT

TECHNICAL FIELD

The present invention relates to a liquid crystalline compound and a liquid crystal composition, more particularly, it relates to a new liquid crystalline compound having substituted alkyl groups, a liquid crystal composition containing the liquid crystalline compound, and a liquid crystal display device constituted by using the liquid crystal composition.

BACKGROUND ART

Liquid crystal devices using liquid crystalline compounds (in the present specification, the term of the liquid crystalline compound is used as a generic name of the compound showing liquid crystal phases and the compound not showing liquid crystal phases but useful as ingredients of the liquid crystal compositions) are broadly used in displays of clocks, watches and electronic calculators, word processors and the like. To these display devices, an optical anisotropy, a dielectric anisotropy and the like of the liquid crystalline compound are applied.

As the liquid crystal phases, a nematic liquid crystal phase, a smectic liquid crystal phase, and a cholesteric liquid crystal phase are used, and particularly, the nematic liquid crystal phase is broadly utilized. As display modes, there are a dynamic scatter (DS) type, a deformation type of an aligning phase (DAP), a guest/host (GH) type, a twisted nematic (TN) type, a super twisted nematic (STN) type, a thin film transistor (TFT) type and the like.

Although the liquid crystalline compounds used in these display modes must show liquid crystal phases at broad temperature ranges, mainly at room temperature, they must be sufficiently stable under conditions that the display devices are used, and they must have characteristics enough to drive the display devices, a single liquid crystalline compound satisfying these conditions is still not found. For these reasons, a few kinds or several tens of kinds of liquid crystalline compounds are conventionally mixed to prepare the liquid crystal compositions satisfying desired properties. It is required that these liquid crystal compositions are stable to moisture, light, heat and air which exist in normal conditions using the display devices, stable to electric field and electromagnetic radiation, and chemically stable to mixed compounds. Further, it is required that these liquid crystal compositions show proper valuer physical properties such as a refractive index anisotropy value ($\Delta n$) and a dielectric anisotropy value ($\Delta \epsilon$) of the liquid crystal compositions dictate the display modes or the forms of the display devices. Further, it is important that each ingredient of these liquid crystal compositions has mutually good solubility.

In recent years, various environment using the liquid crystal devices requires the liquid crystal compositions showing liquid crystal phases at a higher temperature. To achieve the requirement, the ingredient may be constituted from the compounds having high transition temperature of an isotropic phase. Such compounds are known from the compounds represented by formula (a) of Japanese Patent Publication No. 62-46527 and formula (b) of Japanese patent Publication No. 4-28693.

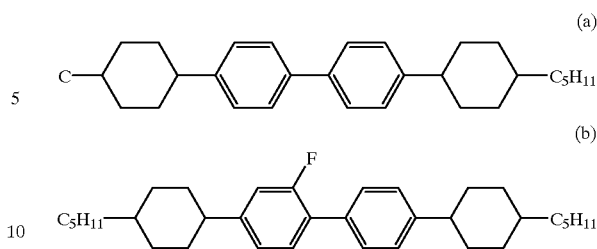

These compounds have a high transition temperature of an isotropic phase and relatively low viscosity, but the compounds have problems that the compatibility with the other ingredients in the composition is not enough, so that the compounds should be used in limited amounts.

Objects of the present invention are to solve the problems of the above conventional techniques, and to provide liquid crystalline compounds having excellent compatibility with the other liquid crystal materials and stability, low viscosity, and a high transition temperature of an isotropic phase; liquid crystal compositions comprising the compounds and liquid crystal devices constituted by using the liquid crystal compositions.

DISCLOSURE OF INVENTION

For achieving the above objects, the present invention is as follows.

(1) A liquid crystalline compound which is represented by general formula (1):

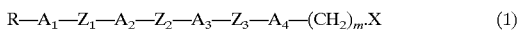

$$R-A_1-Z_1-A_2-Z_2-A_3-Z_3-A_4-(CH_2)_m-X \quad (1)$$

wherein R indicates H or an alkyl group having 1 to 10 carbon atoms (one or more methylene groups (—$CH_2$—) in the alkyl group may be replaced by —O—, —S—, —CO—, —CH=CH— or —C≡C—, but —O— or —S— are not continuous), m indicates an integer of 1 to 10; X indicates F, Cl, Br, I or OH; $A_1$, $A_2$, $A_3$ and $A_4$, each independently, indicate a trans-1,4-cyclohexylene group, a 1,4-phenylene group in which one or more hydrogen atoms on the ring may be substituted by a fluorine atom, a cyclohexenylenediyl group, a pyrimidine-2,5-diyl group, a pyridine-2,5-diyl group or a 1,3-dioxane-2,5-diyl group; $Z_1$, $Z_2$ and $Z_3$, each independently, indicate —$(CH_2)_2$— or a covalent bond, and at least two of $Z_1$, $Z_2$ and $Z_3$ indicate covalent bonds.

(2) A liquid crystalline compound according to (1), wherein X is F.

(3) A liquid crystalline compound according to (1), wherein X is OH.

(4) A liquid crystalline compound according to (2), wherein $Z_1$, $Z_2$ and $Z_3$ are covalent bonds.

(5) A liquid crystalline compound according to (2), wherein $Z_1$ is —$(CH_2)_2$—.

(6) A liquid crystalline compound according to (2), wherein $Z_2$ is —$(CH_2)_2$—.

(7) A liquid crystalline compound according to (2), wherein $Z_3$ is -$(CH_2)2$-.

(8) A liquid crystalline compound according to (4), wherein both $A_1$ and $A_4$ are the trans 1,4-cyclohexylene group, and both $A_2$ and $A_3$ are the 1,4-phenylene group in which one or more hydrogen atoms on the ring may be substituted by a fluorine atom.

(9) A liquid crystalline compound according to (4), wherein both $A_1$ and $A_2$ are the 1,4-phenylene group in which one or more hydrogen atoms on the ring may be substituted by a fluorine atom, and both $A_3$ and $A_4$ are the trans 1,4-cyclohexylene group.

(10) A liquid crystalline compound according to (6), wherein both $A_1$ and $A_2$ are the 1,4-phenylene group in which one or more hydrogen atoms on the ring may be substituted by a fluorine atom, and both $A_3$ and $A_4$ are the trans 1,4-cyclohexylene group.

(11) A liquid crystal composition comprising at least one of liquid crystalline compounds according to any one of (1) to (10).

(12) A liquid crystal composition, characterized in that it comprises as the first constituent at least one compound selected from the group consisting of the liquid crystalline compounds described in any one of (1) to (10), and as the second constituent at least one compound selected from the group consisting of the compounds represented by general formulas (2), (3) and (4):

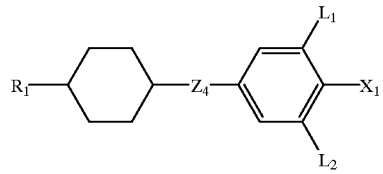
(2)

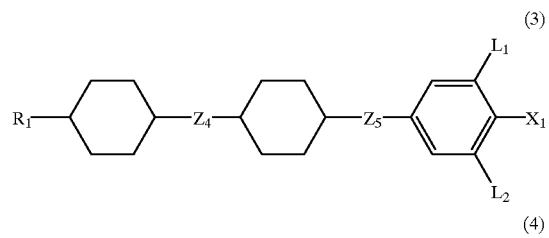
(3)

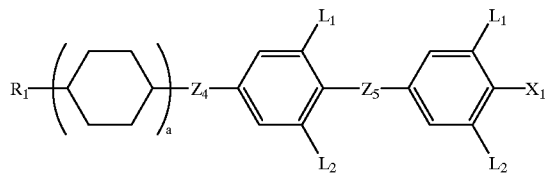
(4)

wherein $R_1$ indicates an alkyl group having 1 to 10 carbon atoms; $X_1$ indicates F, Cl, $OCF_3$, $OCF_2H$, $CF_3$, $CF_2H$ or $CFH_2$; $L_1$, $L_2$, $L_3$ and $L_4$, each independently indicate H or F; $Z_4$ and $Z_5$, each independently, indicate —$(CH_2)_2$—, —CH=CH— or a covalent bond, and a indicates 1 or 2.

(13) A liquid crystal composition, characterized in that it comprises as the first constituent at least one compound selected from the group consisting of the liquid crystalline compounds described in any one of (1) to (10), and as the second constituent at least one compound selected from the group consisting of the compounds represented by general formulas (5), (6), (7), (8) and (9):

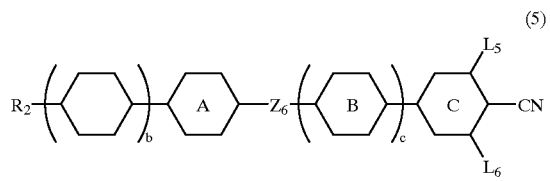
(5)

wherein $R_2$ indicates F, an alkyl group having 1 to 10 carbon atoms or an alkenyl group having 2 to 10 carbon atoms; any methylene group (—$CH_2$—) in the alkyl group or the alkenyl group may be replaced by an oxygen atom(—O—), but two or more methylene groups are not continuously replaced by the oxygen atom; ring A indicates a trans-1,4-cyclohexylene group, a 1,4-phenylene group or a 1,3-dioxane-2,5-diyl group; ring B indicates a trans-1,4-cyclohexylene group, a 1,4-phenylene group or a pyrimidine-2,5-diyl group; ring C indicates a trans-1,4-cyclohexylene group or a 1,4-phenylene group; $Z_6$ indicates —$(CH_2)_2$—, —COO— or a covalent bond; $L_5$ and $L_6$, each independently, indicate H or F; and b and c, each independently, indicate 0 or 1,

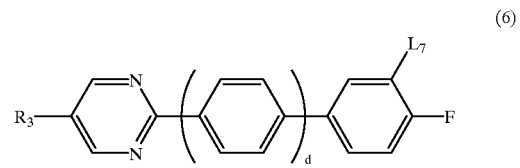
(6)

wherein $R_3$ indicates an alkyl group having 1 to 10 carbon atoms, $L_7$ indicates H or F, and d indicates 0 or 1,

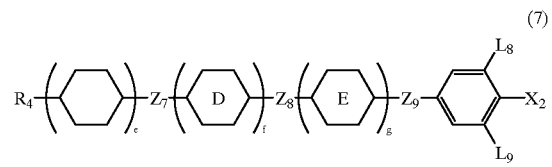
(7)

wherein $R_4$ indicates an alkyl group having 1 to 10 carbon atoms; ring D and ring E, each independently, indicate trans-1,4-cyclohexylene group or a 1,4-phenylene group; $Z_7$ and $Z_8$, each independently, indicate -COO- or a covalent bond; $Z_9$ indicates —COO— or —C≡C—; $L_8$ and $L_9$, each independently, indicate H or F; $X_2$ indicates F, $OCF_3$, $OCF_2H$, $CF_3$, $CF_2H$ or $CFH_2$, when $X_2$ indicates $OCF_3$, $OCF_2H$, $CF_3$, $CF_2H$ or $CFH_2$, $L_8$ and $L_9$ both indicate H; e, f and g, each independently, indicate 0 or 1,

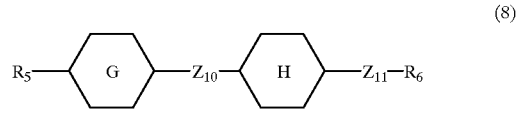
(8)

wherein $R_5$ and $R_6$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring G indicates a trans-1,4-cyclohexylene group, a 1,4-phenylene group or a pyrimidine-2,5-diyl group; ring H indicates a trans-1,4-cyclohexylene group or a 1,4-phenylene group; $Z_{10}$ indicates —C≡C—, —COO—, —$(CH_2)_2$—, —CH=CH— C≡C— or a covalent bond; $Z_{11}$ indicates —COO— or a covalent bond, and

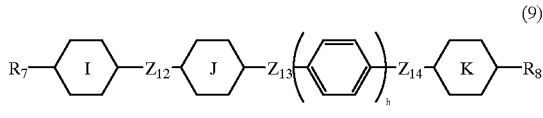

(9)

wherein $R_7$ and $R_8$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring I indicates a trans-1,4-cyclohexylene group, a 1,4-phenylene group or a pyrimidine-2,5-diyl group; ring J indicates a trans-1,4-cyclohexylene group, a 1,4-phenylene group in which one or more hydrogen atoms on the ring may be substituted by a fluoric atom, or a pyrimidine-2,5-diyl group; ring K indicates a trans-1,4-cyclohexylene group or a 1,4-phenylene group, $Z_{12}$ and $Z_{14}$, each independently, indicate —COO—, —($CH_2$)$_2$— or a covalent bond, $Z_{13}$ indicates —CH=CH—, —C≡C—, —COO— or a covalent bond; and h indicates 0 or 1.

(14) A liquid crystal composition, characterized in that it comprises as the first constituent at least one compound selected from the group consisting of the liquid crystalline compounds described in any one of (1) to (10), and as a part of the second constituent at least one compound selected from the group consisting of the compounds represented by general formulas (2), (3) and (4), and the other part of the second constituent at least one compound selected from the group consisting of the compounds represented by general formulas (5), (6), (7), (8) and (9).

(15) A liquid crystal display device constituted by using the liquid crystal compositions described in any one of (1) to (14).

The liquid crystalline compounds represented by general formula (1) in the present invention have excellent compatibility with the other liquid crystal materials, and a high transition temperature of an isotropic phase. These compounds do not show increase of viscosity by introduction of substituted alkyl groups. Further, these liquid crystalline compounds are physically and chemically stable under conditions using commonly display devices. In addition, by appropriate selection of six-membered rings, substituted groups and/or bond groups from molecular constituents, it is possible to obtain a compound having desired physical properties. Accordingly, when the compounds of the present invention are used as ingredients of liquid crystal compositions, it is possible to provide new liquid crystal compositions having preferable characteristics.

The compounds represented by general formula (1) in the present invention are classified as follows:

In the following formulas, Q indicates —($CH_2$)$_m$—X, wherein m indicates the same meaning as described above. Cyc indicates a trans-1,4-cyclohexylene group, Phe indicates a 1,4-phenylene group, Hex indicates a cyclohexenylenediyl group, Pyr indicates a pyrimidine-2,5-diyl group, Pyd indicates a pyridine-2,5-diyl group, Dio indicates a 1,3-dioxane-2,5-diyl group, and one or more hydrogen atoms of the above Phe may be substituted by fluorine atoms; $A_1$, $A_2$, $A_3$ and $A_4$ are selected from Cyc, Phe, Hex, Pyr, Pyd or Dio, preferably, there are not two or more hetero rings.

| | |
|---|---|
| R-$A_1$-$A_2$-$A_3$-$A_4$-Q | (1a) |
| R-$A_1$-($CH_2$)$_2$-$A_2$-$A_3$-$A_4$-Q | (1b) |
| R-$A_1$-$A_2$-($CH_2$)$_2$-$A_3$-$A_4$-Q | (1c) |
| R-$A_1$-$A_2$-$A_3$-($CH_2$)$_2$-$A_4$-Q | (1d) |

The compounds represented by formula (1a) are developed into the compounds represented by the following formulas (1aa)–(1ap).

| | |
|---|---|
| R-Cyc-Cyc-Cyc-Cyc-Q | (1aa) |
| R-Cyc-Cyc-Cyc-Phe-Q | (1ab) |
| R-Cyc-Cyc-Phe-Phe-Q | (1ac) |
| R-Cyc-Phe-Phe-Phe-Q | (1ad) |
| R-Phe-Phe-Phe-Phe-Q | (1ae) |
| R-Phe-Phe-Phe-Cyc-Q | (1af) |
| R-Phe-Phe-Cyc-Cyc-Q | (1ag) |
| R-Phe-Cyc-Cyc-Cyc-Q | (1ah) |
| R-Cyc-Cyc-Phe-Cyc-Q | (1ai) |
| R-Cyc-Phe-Phe-Cyc-Q | (1ak) |
| R-Phe-Phe-Cyc-Phe-Q | (1al) |
| R-Hex-Phe-Phe-Hex-Q | (1am) |
| R-Phe-Pyr-Phe-Cyc-Q | (1an) |
| R-Dio-Cyc-Phe-Phe-Q | (1ao) |
| R-Pyr-Phe-Cyc-Cyc-Q | (1ap) |

The compounds represented by formula (1b) are developed into the compounds represented by the following formulas (1ba)–(1bp).

| | |
|---|---|
| R-Cyc-($CH_2$)$_2$-Cyc-Cyc-Cyc-Q | (1ba) |
| R-Cyc-($CH_2$)$_2$-Cyc-Cyc-Phe-Q | (1bb) |
| R-Cyc-($CH_2$)$_2$-Cyc-Phe-Phe-Q | (1bc) |
| R-Cyc-($CH_2$)$_2$-Phe-Phe-Phe-Q | (1bd) |
| R-Phe-($CH_2$)$_2$-Phe-Phe-Phe-Q | (1be) |
| R-Phe-($CH_2$)$_2$-Phe-Phe-Cyc-Q | (1bf) |
| R-Phe-($CH_2$)$_2$-Phe-Cyc-Cyc-Q | (1bg) |
| R-Phe-($CH_2$)$_2$-Cyc-Cyc-Cyc-Q | (1bh) |
| R-Cyc-($CH_2$)$_2$-Cyc-Phe-Cyc-Q | (1bi) |
| R-Cyc-($CH_2$)$_2$-Phe-Cyc-Cyc-Q | (1bj) |
| R-Cyc-($CH_2$)$_2$-Phe-Phe-Cyc-Q | (1bk) |
| R-Phe-($CH_2$)$_2$-Phe-Cyc-Phe-Q | (1bl) |
| R-Phe-($CH_2$)$_2$-Cyc-Phe-Phe-Q | (1bm) |
| R-Phe-($CH_2$)$_2$-Cyc-Cyc-Phe-Q | (1bn) |
| R-Cyc-($CH_2$)$_2$-Cyc-Phe-Pyd-Q | (1bo) |
| R-Cyc-($CH_2$)$_2$-Cyc-Cyc-Dio-Q | (1bp) |

The compounds represented by formula (1c) are developed into the compounds represented by the following formulas (1ca)–(1cp).

| | |
|---|---|
| R-Cyc-Cyc-($CH_2$)$_2$-Cyc-Cyc-Q | (1ca) |
| R-Cyc-Cyc-($CH_2$)$_2$-Cyc-Phe-Q | (1cb) |
| R-Cyc-Cyc-($CH_2$)$_2$-Phe-Phe-Q | (1cc) |
| R-Cyc-Phe-($CH_2$)$_2$-Phe-Phe-Q | (1cd) |
| R-Phe-Phe-($CH_2$)$_2$-Phe-Phe-Q | (1ce) |
| R-Phe-Phe-($CH_2$)$_2$-Phe-Cyc-Q | (1cf) |
| R-Phe-Phe-($CH_2$)$_2$-Cyc-Cyc-Q | (1cg) |
| R-Phe-Cyc-($CH_2$)$_2$-Cyc-Cyc-Q | (1ch) |
| R-Cyc-Cyc-($CH_2$)$_2$-Phe-Cyc-Q | (1ci) |
| R-Cyc-Phe-($CH_2$)$_2$-Cyc-Cyc-Q | (1cj) |
| R-Cyc-Phe-($CH_2$)$_2$-Phe-Phe-Q | (1ck) |
| R-Phe-Phe-($CH_2$)$_2$-Cyc-Phe-Q | (1cl) |
| R-Phe-Cyc-($CH_2$)$_2$-Phe-Phe-Q | (1cm) |
| R-Phe-Cyc-($CH_2$)$_2$-Cyc-Phe-Q | (1cn) |
| R-Dio-Cyc-($CH_2$)$_2$-Phe-Phe-Q | (1co) |
| R-Hex-Phe-($CH_2$)$_2$-Phe-Cyc-Q | (1cp) |

The compounds represented by formula (1d) are developed into the compounds represented by the following formulas (1da)–(1dp).

| | |
|---|---|
| R-Cyc-Cyc-Cyc-(CH$_2$)$_2$-Cyc-Q | (1da) |
| R-Cyc-Cyc-Cyc-(CH$_2$)$_2$-Phe-Q | (1db) |
| R-Cyc-Cyc-Phe-(CH$_2$)$_2$-Phe-Q | (1dc) |
| R-Cyc-Phe-Phe-(CH$_2$)$_2$-Phe-Q | (1dd) |
| R-Phe-Phe-Phe-(CH$_2$)$_2$-Phe-Q | (1de) |
| R-Phe-Phe-Phe-(CH$_2$)$_2$-Cyc-Q | (1df) |
| R-Phe-Phe-Cyc-(CH$_2$)$_2$-Cyc-Q | (1dg) |
| R-Phe-Cyc-Cyc-(CH$_2$)$_2$-Cyc-Q | (1dh) |
| R-Cyc-Cyc-Phe-(CH$_2$)$_2$-Cyc-Q | (1di) |
| R-Cyc-Phe-Cyc-(CH$_2$)$_2$-Cyc-Q | (1dj) |
| R-Cyc-Phe-Phe-(CH$_2$)$_2$-Cyc-Q | (1dk) |
| R-Phe-Phe-Cyc-(CH$_2$)$_2$-Phe-Q | (1dl) |
| R-Phe-Cyc-Phe-(CH$_2$)$_2$-Phe-Q | (1dm) |
| R-Phe-Cyc-Cyc-(CH$_2$)$_2$-Phe-Q | (1dn) |
| R-Cyc-Phe-Cyc-(CH$_2$)$_2$-Phe-Q | (1do) |
| R-Cyc-Dio-Phe-(CH$_2$)$_2$-Phe-Q | (1dp) |

In the above all compounds, Q is a ω-substituted alkyl group, preferably, fluoromethyl, 2-fluoroethyl, 3-fluoropropyl, 4-fluorobutyl, 5-fluoropentyl, 6-fluorohexyl, 10-fluorodecyl, chloromethyl, 2-chloroethyl, 3-chloropropyl, 4-chlorobutyl, 5-chloropentyl, 6-chlorohexyl, 9-chlorononyl, bromomethyl, 2-bromoethyl, 3-bromopropyl, 4-bromobutyl, 5-bromopentyl, 6-bromohexyl, 8-bromooctyl, iodomethyl, 2-iodoethyl, 3-iodopropyl, 4-iodobutyl, 5-iodopentyl, 6-iodohexyl, 7-iodoheptyl, hydroxymethyl, 2-hydroxyethyl, 3-hydroxypropyl, 4-hydroxybutyl, 5-hydroxypentyl, 6-hydroxyhexyl or 10-hydroxydecyl.

As shown in the above, the compounds represented by formulas (1aa)–(1ap), (1ba)–(1bp), (1ca)–(1cp) and (1da)–(1dp) are preferable compounds. Most preferably, the compounds represented by the following formulas (1-1)–(1-44) are exemplified.

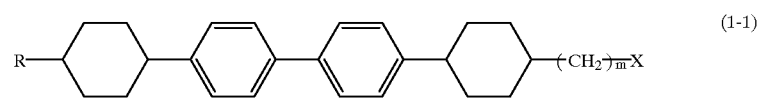
(1-1)

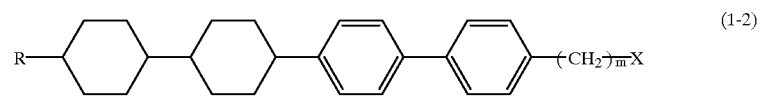
(1-2)

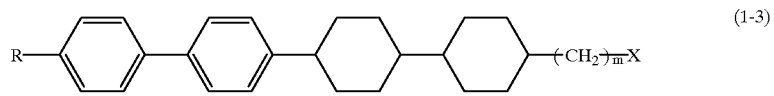
(1-3)

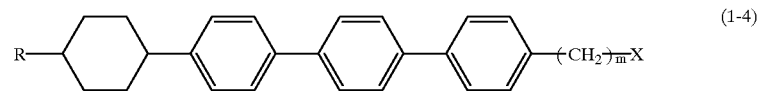
(1-4)

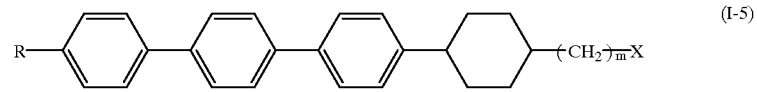
(I-5)

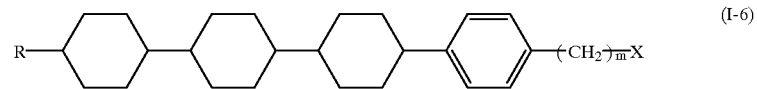
(I-6)

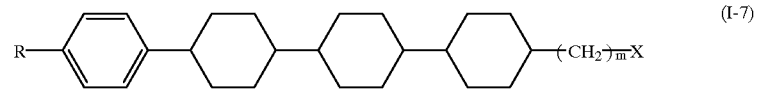
(I-7)

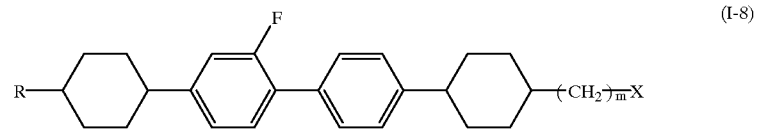
(I-8)

-continued
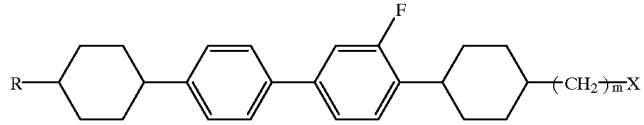
(I-9)
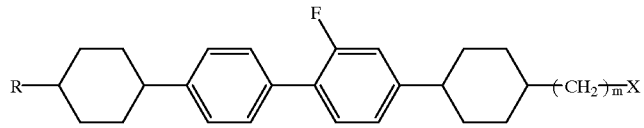
(I-10)
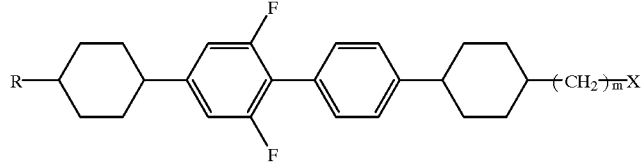
(I-11)
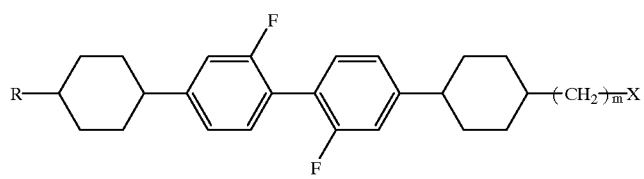
(I-12)
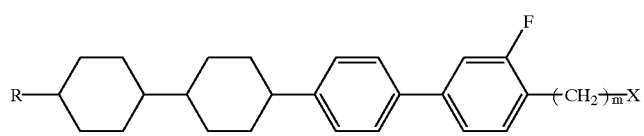
(I-13)
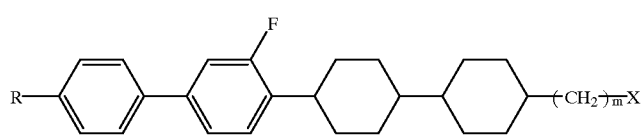
(I-14)
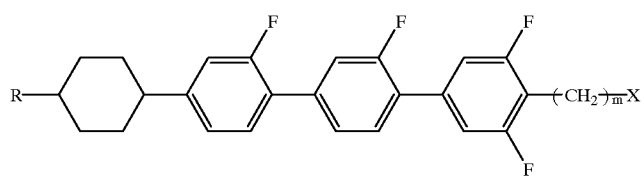
(I-15)
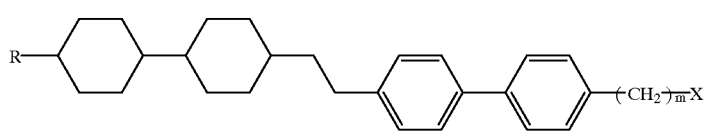
(I-16)
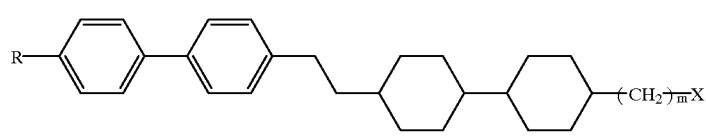
(I-17)
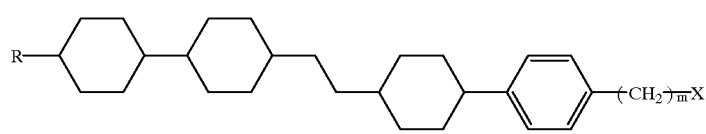
(I-18)

-continued
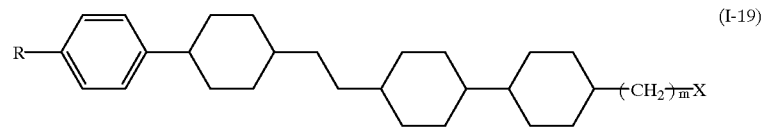
(I-19)
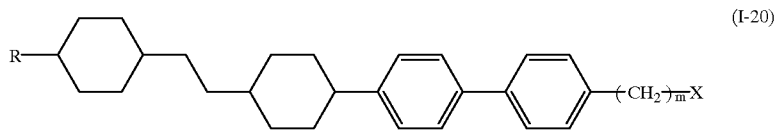
(I-20)
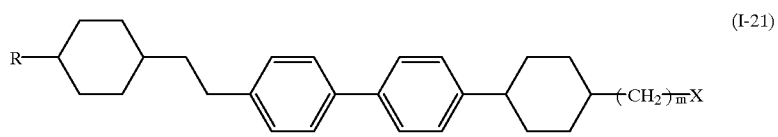
(I-21)
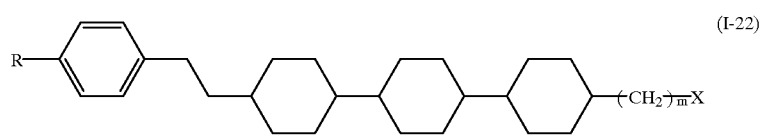
(I-22)
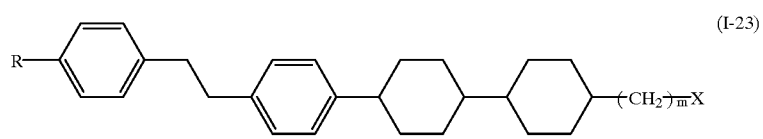
(I-23)
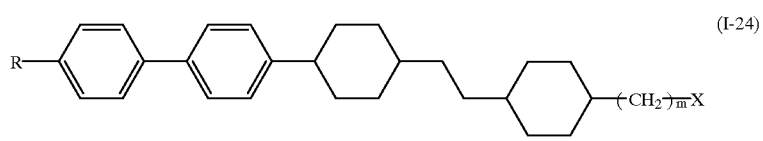
(I-24)
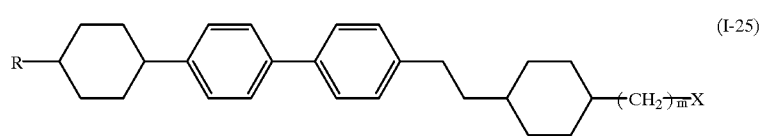
(I-25)
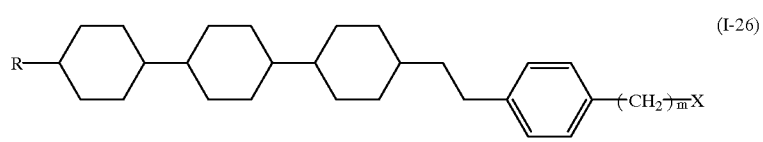
(I-26)
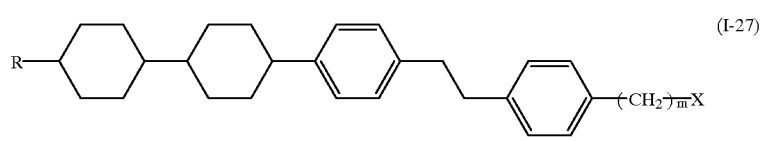
(I-27)
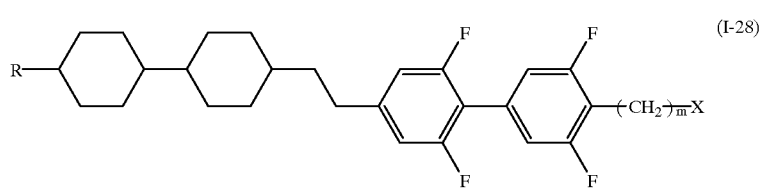
(I-28)

-continued
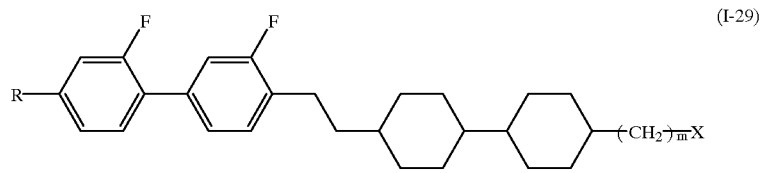
(I-29)
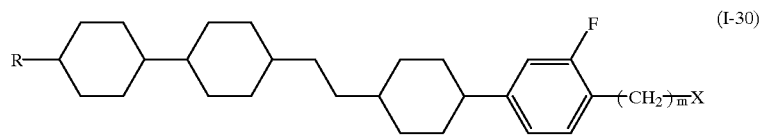
(I-30)
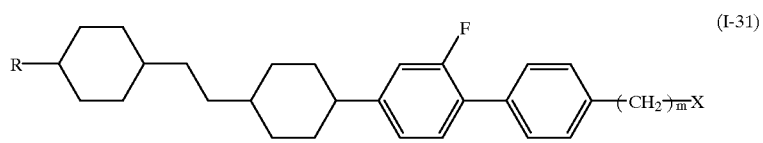
(I-31)
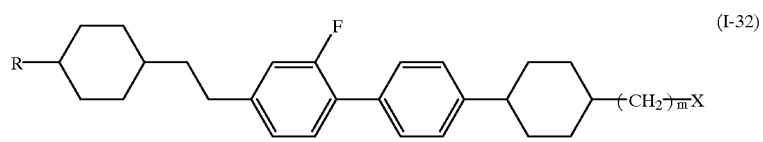
(I-32)
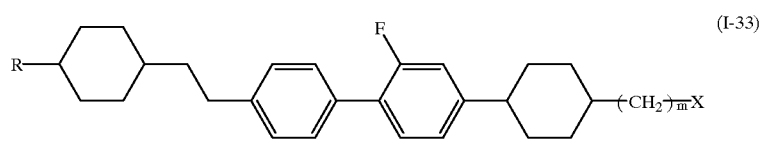
(I-33)
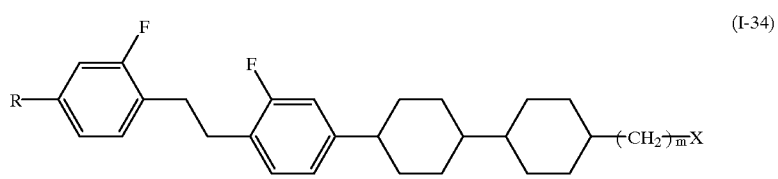
(I-34)
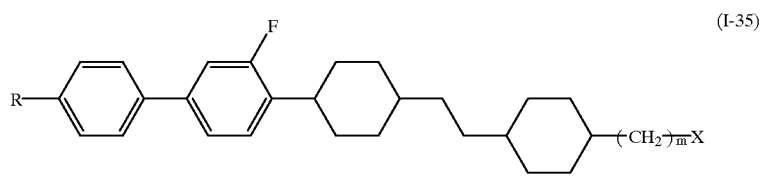
(I-35)
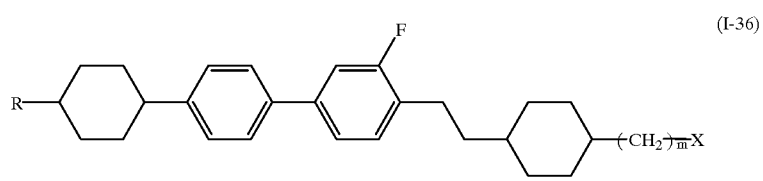
(I-36)
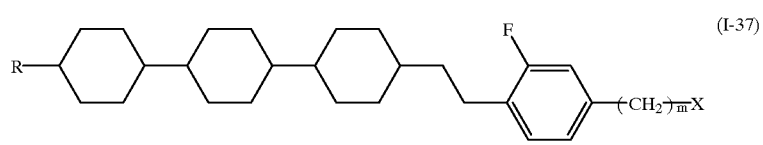
(I-37)

-continued
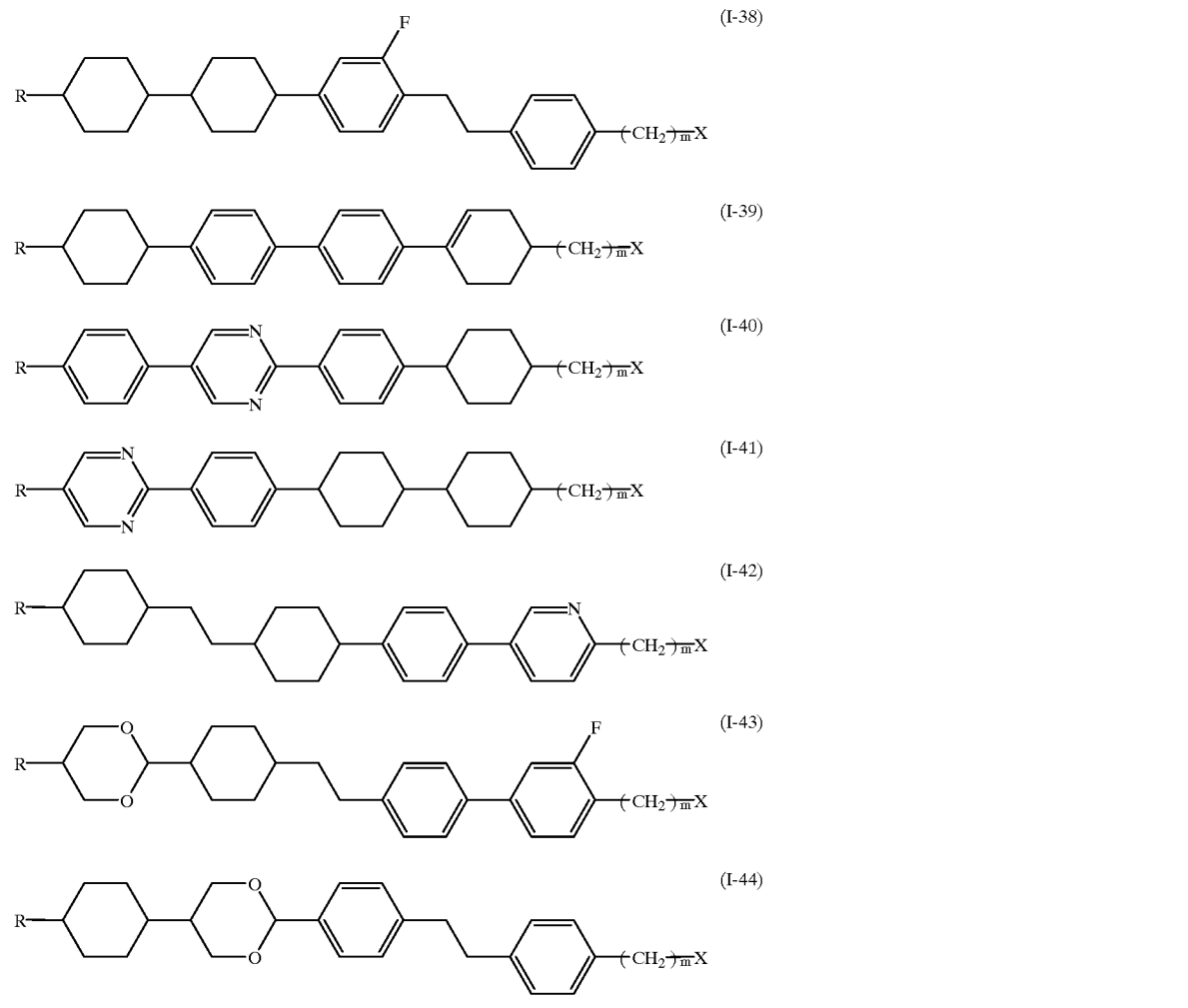
The liquid crystalline compounds represented by general formula (1) in the present invention can be prepared by well-known common organic synthetic methods, for example, by the following process.
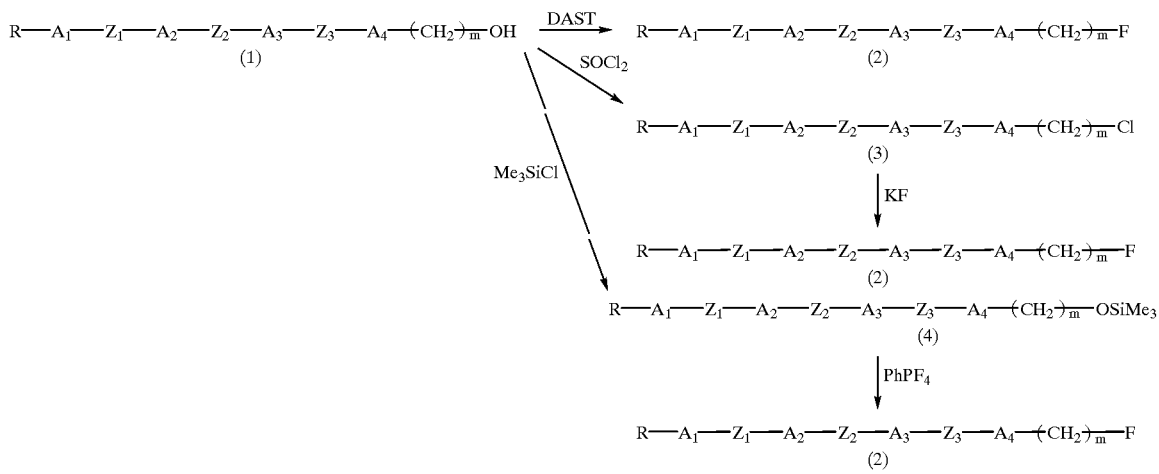

Namely, compound (1) that X is OH in formula (1) can be treated with a fluorinating agent such as diethylamino sulfur trifluoride (DAST) (M. Hudlicky, Organic Reactions, 35, 513 (1988), P. A. Messina et al., The Journal of Fluorine Chemistry, 42, 137 (1989)), (2-chloro-1,1,2-trifluoroethyl) diethylamine (C. M. Sharts et al., Organic Reactions, 21, 158 (1974)), molpholino sulfur trifluoride (K. C. Mange et al., The Journal of Fluorine Chemistry, 43, 405 (1989)) or diethylamine-hexafluoropropene (Ishikawa et al., Bulletin of the Chemical Society of Japan, 52 (11), 3377 (1979)), to produce compound (2) that X is F in formula (1).

Compound (2) also can be obtained by reaction of the above alcohol (1) with a halogenation agent such as hydrogen chloride/zinc chloride, hydrobromic acid, hydroiodic acid, thionyl chloride, thionyl bromide, potassium iodide, phosphorus triiodide, phosphorus trichloride, phosphorus tribromide, phosphorus pentachloride or phosphorus oxychloride, and further, by reaction of compound (3) that X is a halogen atom in formula (1) with a fluorinating agent such as KF (Ishikawa et al., Chemistry Letters, 761 (1981)), pyridynium poly (hydrogen fluoride) (HF—Py) (G. A. Olah et al., The Journal of Organic Chemistry, 44, 3872 (1979)), n-Bu$_4$NF (D. O. Kiesewetter et al., The Journal of Organic Chemistry, 49, 4900 (1984)) or a Ph$_4$PF—HF complex (S. J. Brown et al., Journal of the Chemical Society Chemical Communications, 672 (1985)).

Moreover, after changing the above alcohol (1) is into silyl ether (4), the above compound (2) can be produced by fluorination of silyl ether (4) with a fluorinating agent such as PhPF$_4$ (H. Koop et al., Journal of Fluorine Chemistry, 1, 252 (1972), n-Bu$_4$NF/CH$_3$SO$_2$F or DAST and the like.

The above alcohol (1) which is a starting material can be produced by a well-known common organic synthetic process, for example, it is easily obtained by the following methods as shown in scheme 1-12.

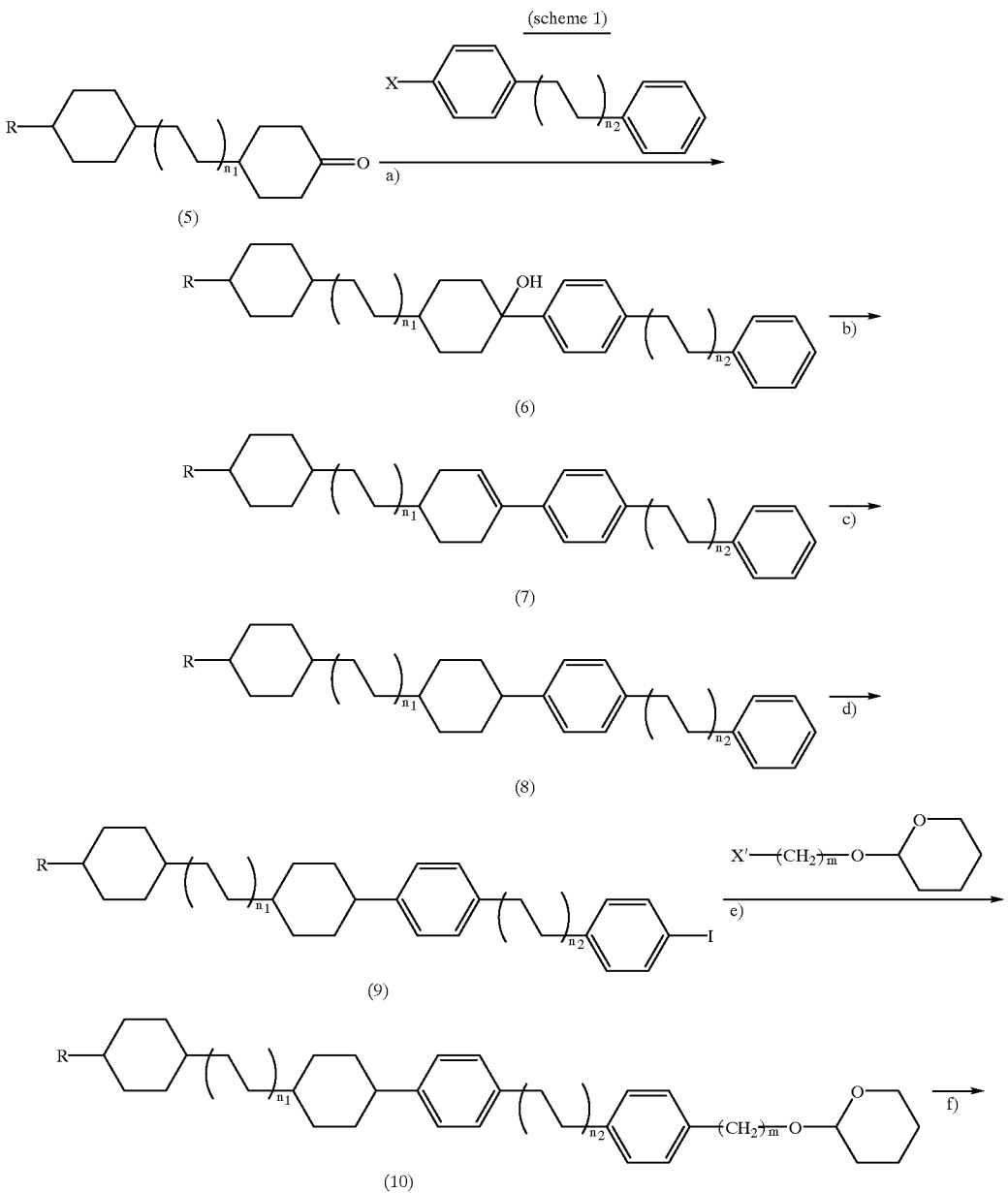

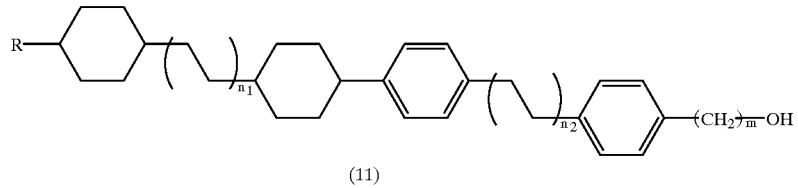
(scheme 2)
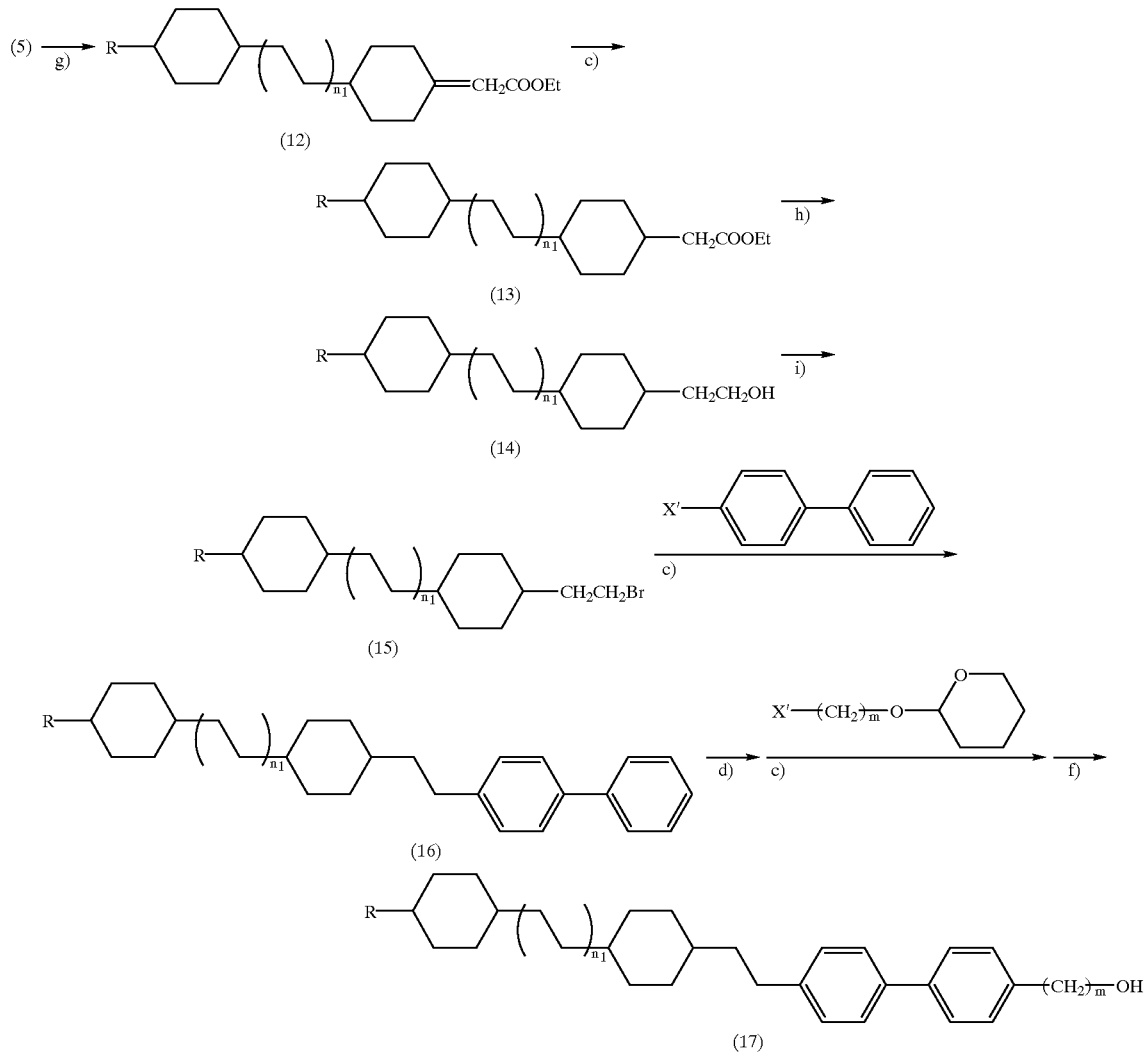
(scheme 3)
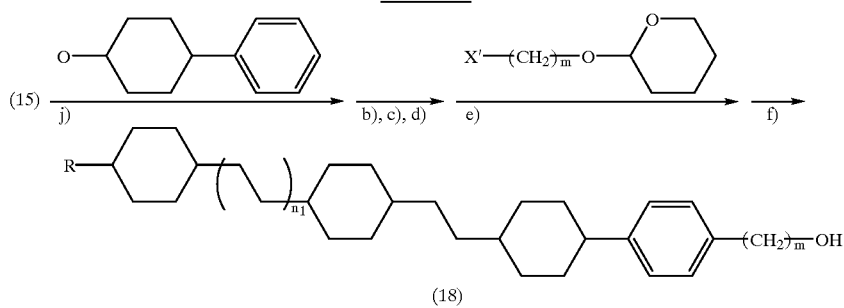

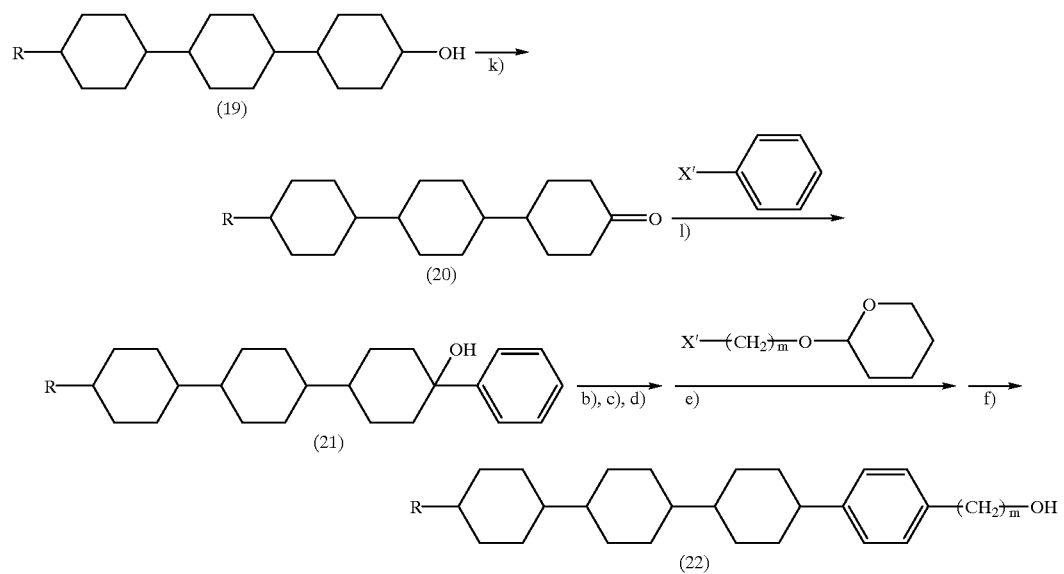
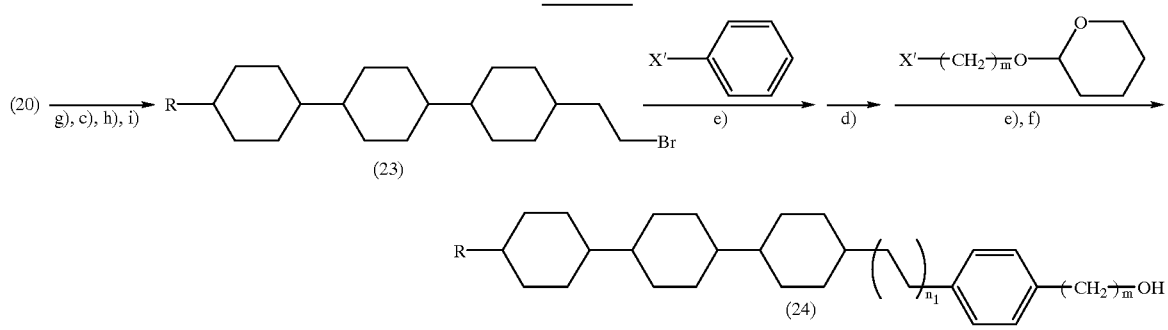
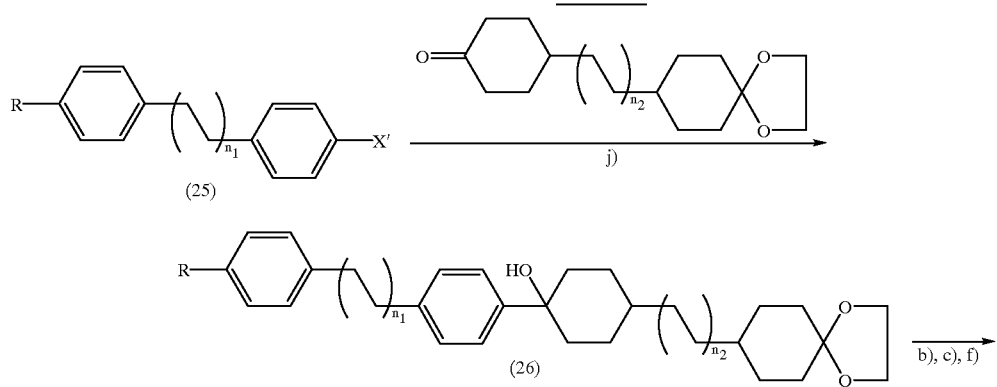

-continued
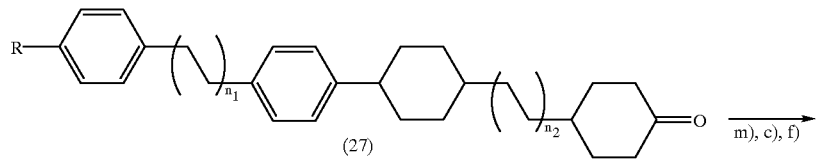
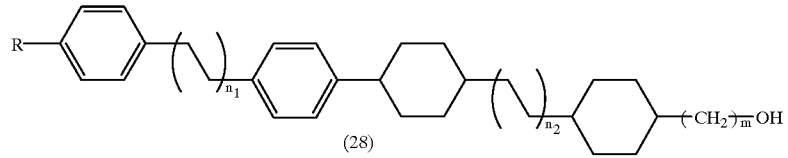
(scheme 7)
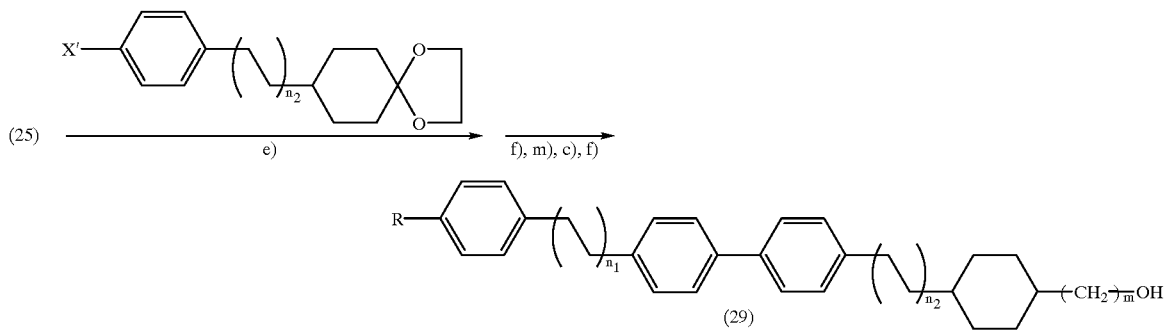
(scheme 8)
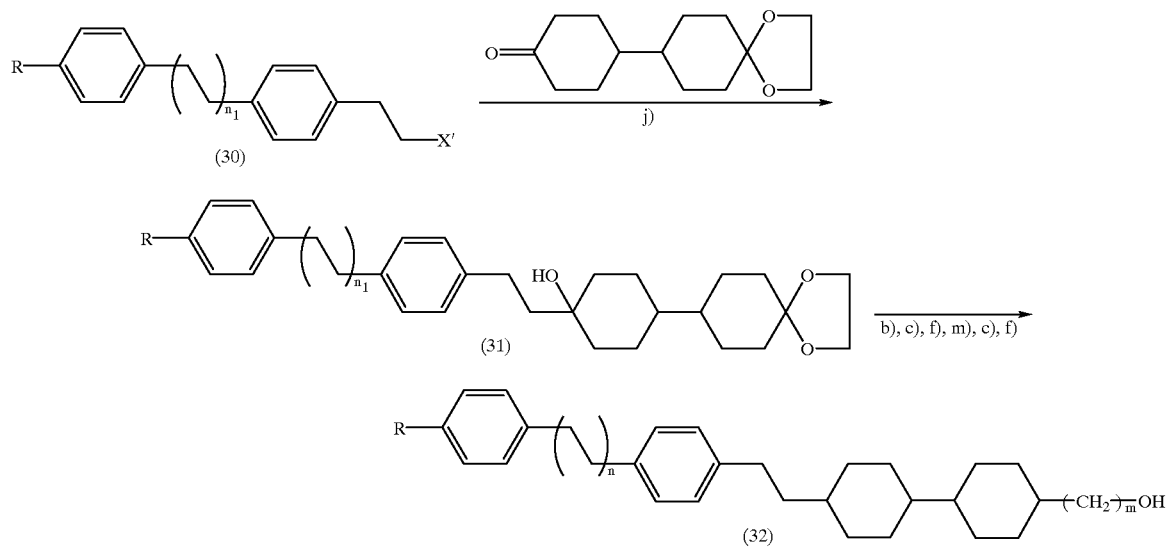

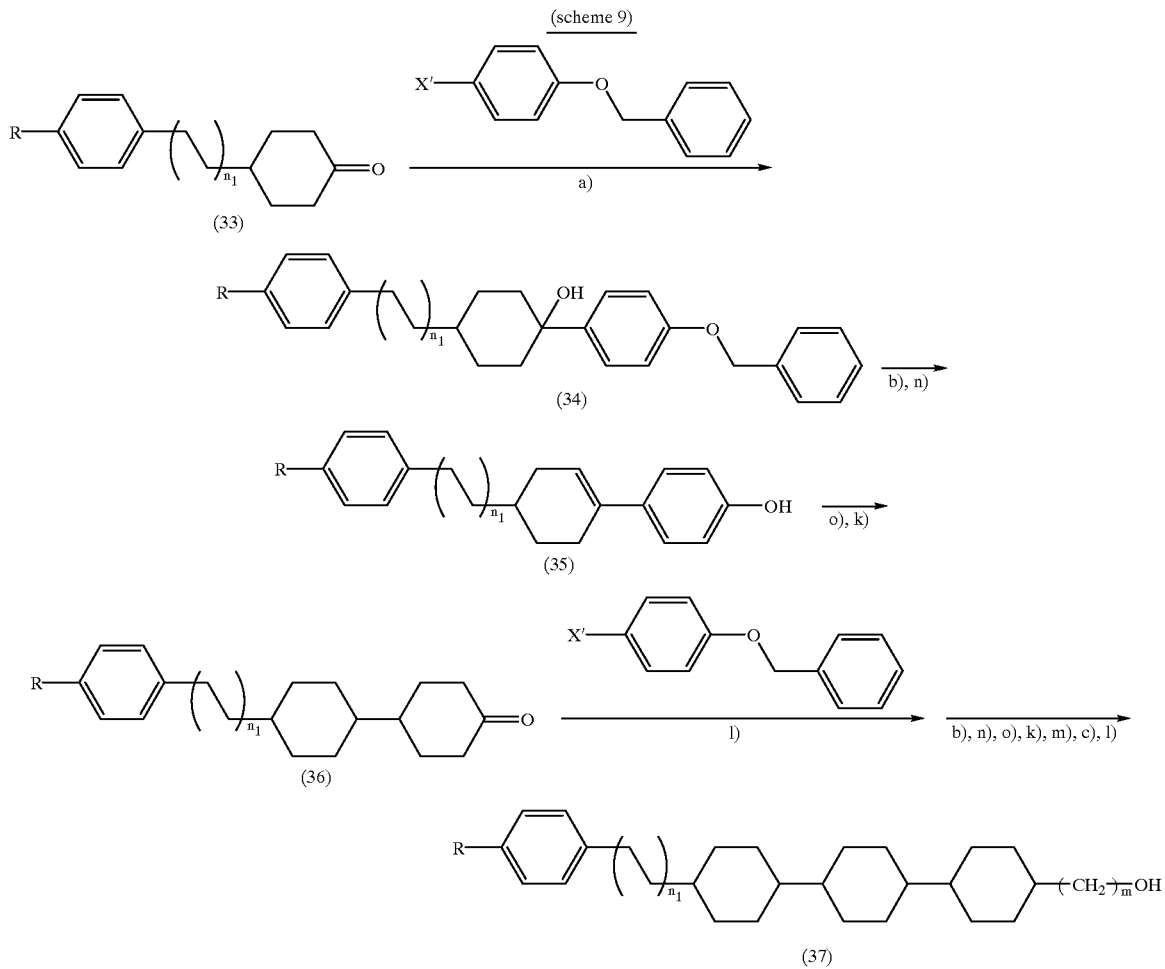
(scheme 9)
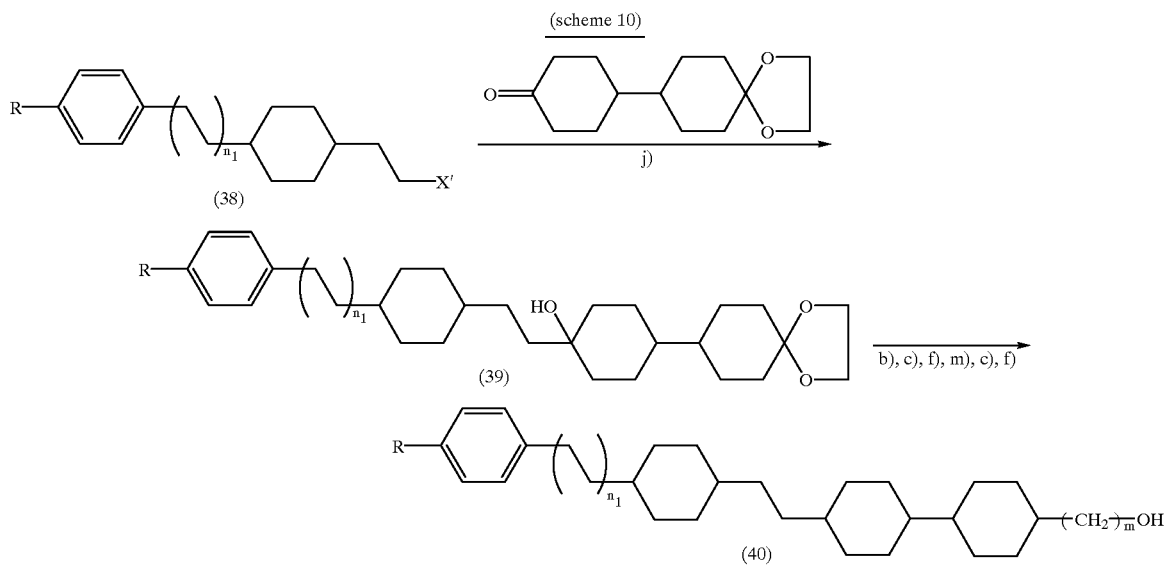
(scheme 10)

(scheme 11)

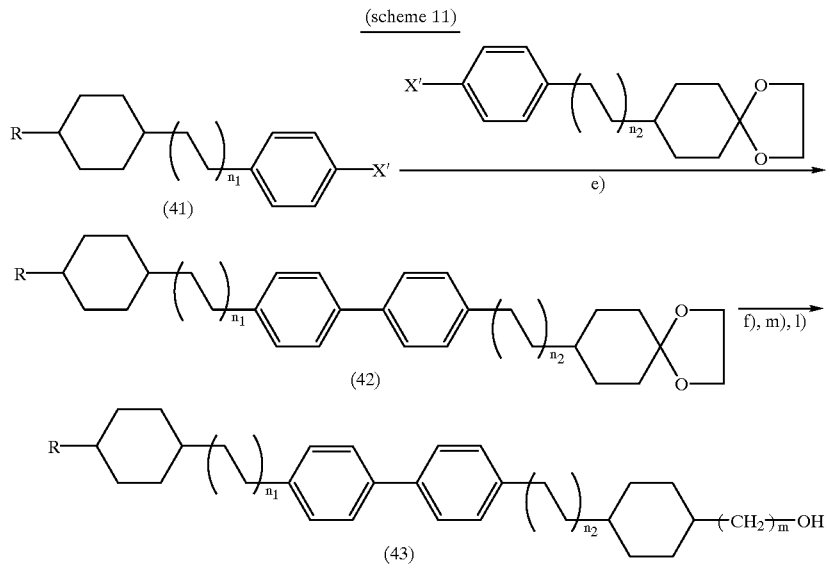

(scheme 12)

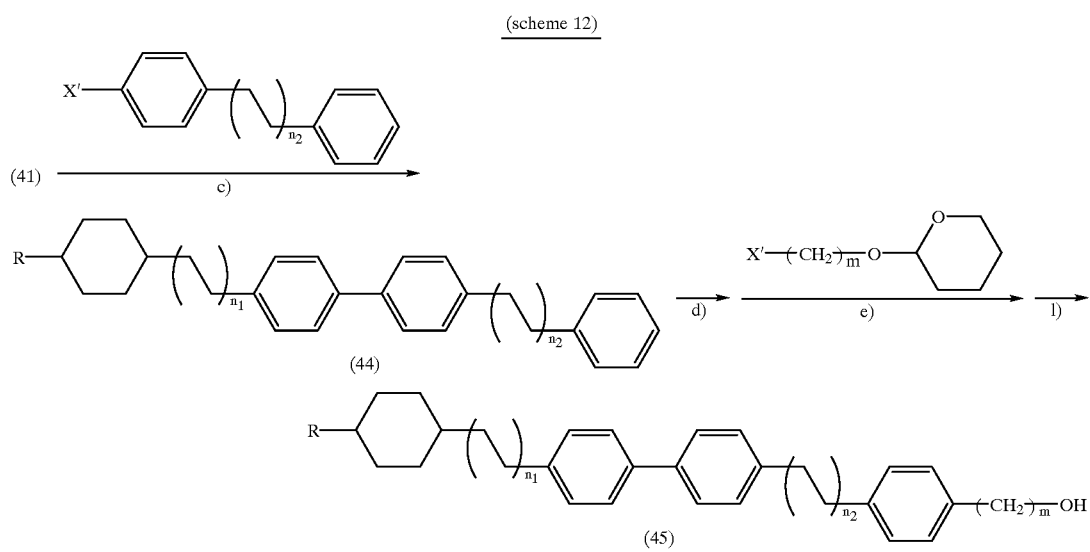

In each scheme, $n_1$ and $n_2$, each independently, indicates 0 or

Reaction conditions: 1, and X' indicates Br or I.

a) halide/n-BuLi
b) —$H_2O$/acid catlyst
c) $H_2$/Pd-C
d) $I_2$/SbCl$_5$
e) halide/n-BuLi/ZnCl$_2$
f) H$^+$
g) (EtO)$_2$POCH$_2$COOEt/base
h) LAH
i) HBr
j) cyclohexanone derivative/n-Buli
k) PCC
l) halide/Mg -continued m)

<img> O—(CH$_2$)$_{\overline{m}}$—P'Ph$_3$X"/base </img> n) Me$_3$SiI
o) Ru-C

Namely, as shown in scheme 1, after compound (5) is changed into compound (6) by the method of J. D. Buhler et al. described in The Journal of Organic Chemistry, 38, 904 (1973)) or the method of Imamoto et al. described in Journal of the American Chemical Society, 111, 4392 (1989)), compound (7) is obtained by heating and dehydration in a solvent such as toluene or xylene in the presence of an acidic catalyst such as p-toluenesulfonic acid. After compound (7) is changed into compound (8) by catalytic hydrogenation in the presence of a catalyst such as Pd—C, halide (9) is obtained by a method of Uemura et al., Bulletin of the Chemical Society of Japan, 47, 147 (1974) or a method of H. Becker et al, Organikum, VEB Deutscher Verlag der Wissenschaften, 189 (1973)).

After compound (9) is treated by cross coupling reaction of a method of Hayashi et al.(Journal of the American Chemical Society, 106, 158 (1984)) or a method of Negishi et al. (The Journal of Organic Chemistry, 42 (10), 1821 (1977)), compound (11) of an example of an alcohol derivative is obtained by deprotection.

In addition, after a Grignard reagent or a lithium reagent of compound (9) is prepared, it is reacted with formaldehyde, or a cyclic ether of ethyleneoxide or propyleneoxide, corresponding alcohol derivatives are obtained, respectively.

Then, as shown in scheme 2, after compound (5) is changed into compound (12) by a method of W. S. Wardsworth et al. (Journal of the American Chemical Society, 83, 1733 (1961), it is reacted by catalytic hydrogenation to obtain compound (13). Then, the resulting compound (13) is reduced with a reducing agent such as lithium aluminum hydride (LAH), bis(2-methoxyethoxy)aluminum sodium hydride, boron lithium hydride or diisobuthyl aluminum hydride to obtain compound (4).

Said compound (14) is changed to a halide (15) by a method of those of H. Becker et al. (Organikum, VEB Deutscher Verlag der Wissenschaften, 212 (1973), C. R. Noller et al. (Organic Synthesis, II, 358 (1943)), G. A. Wiley et al. (Journal of the American Chemical Society, 86, 964 (1964)), S. Manna et al. (Synthetic Communications, 15, 633 (1985)), G. Cainelli et al. (Synthesis, 306 (1983)), G. H. Daub et al. (The Journal of Organic Chemistry, 19, 1571 (1954)), H. Stone et al. (Organic Synthesis, IV, 323 (1963)), G. A. Olah et al. (Synthesis, 653 (1974), The Journal of Organic Chemistry, 44, 1247 (1979)), Imamoto et al. (Synthesis, 460 (1983)) and the like; a cross coupling method such as a method of Hayashi et al., and halogenation of a method of Uemura et al., and a cross coupling method of Hayashi et al. are conducted; the resulting product are deprotected to obtain compound (17) as an example of alcohol derivatives.

Further, as shown in scheme 3, said compound (15) is reacted into compound (18) as an example of alcohol derivatives through the steps of the method of aforementioned J. D. Buhler et al., dehydration, catalytic hydrogenation, halogenation by the method of Uemura et al., and cross coupling by the method of Hayashi et al., and deprotection.

As shown in scheme 4, compound (19) obtained by a method of W. Sucrow et al. (Chemische Berichte, 121, 219 (1988)) is oxidized with an oxidizing agent such as pyridinium chlorochromate (PCC), pyridinium dichromate, pyridinium fluorochromate, chromium oxide, activated manganese dioxide or dimethyl sulfoxide/oxaryl chloride to obtain compound (20).

Then, compound (20) is reacted with phenyl magnesium halide of a Grignard reagent, dehydrated, reacted by catalytic hydrogenation, by halogenation of the above method of Uemura et al, by a cross coupling reaction of the above method of Hayashi et al., and by deprotection to obtain compound (22) which is an example of alcohol derivatives.

Moreover, as shown in scheme 5, the above compound (20) is reacted by the above method of W. S. Wardsworth et al., by catalytic hydrogenation, by reduction, and by the above method of H. Becker et al. to obtain compound (23). Then, after the cross coupling reaction of Hayashi et al., halogenation by the method of Uemura et al., and cross coupling by the method of Hayashi et al., the resulting compound can be deprotected to obtain compound (24) of the example of alcohol derivatives.

Moreover, as shown in scheme 6, compound (25) is changed into compound (27) through the steps of the method of aforementioned J. D. Buhler et al., dehydration, catalytic hydrogenation and deprotection. Then, after compound (27) is reacted by Wittig reaction (G. Wittig et al., Angewandte Chemie, 71, 121, 1373 (1959), Organic Reactions, Vol. 14, Chapter 3) and catalytic hydrogenation, the resulting compound can be deprotected to obtain compound (28) as an example of alcohol derivatives.

Further, as shown in scheme 7, after compound (25) is reacted by the cross coupling reaction of Hayashi et al., deprotection, a Wittig reaction and catalytic hydrogenation, the resulting compound can be deprotected to obtain compound (29) as an example of alcohol derivatives.

As shown in scheme 8, compound (30) is reacted by the method of J. D. Buhler et al to obtain compound (31). Compound (31) is reacted by dehydration, catalytic hydrogenation, deprotection, a Wittig reaction and catalytic hydrogenation, and the resulting compound is deprotected to obtain compound (32) as an example of alcohol derivatives.

As shown in scheme 9, after compound (33) is changed into compound (34) by the method of J. D. Buhler et al. and the compound is changed into compound (35) by dehydration and deprotection with iode trimethyl silane, boron trifluoride or the like. Compound (35) is reacted by catalytic hydrogenation in the presence of a catalyst such as Ru—C and oxidized to obtain compound (36).

After repeating the reaction from compound (33) to compound (36) to obtain a cyclohexanone derivative, the derivative is reacted by the Wittig reaction and catalytic hydrogenation, and the resulting compound can be deprotected to obtain compound (37) as an example of alcohol derivatives.

Moreover, as shown in scheme 10, after compound (38) is reacted by the method of J. D. Buhler et al., dehydration, catalytic hydrogenation, deprotection, the Wittig reaction and catalytic hydrogenation, the resulting compound can be deprotected to obtain compound (40) as an example of alcohol derivatives.

As shown in scheme 11, after compound (41) is reacted by the cross coupling method of Hayashi et al., deprotection and the Wittig reaction, the resulting compound can be deprotected to obtain compound (43) as an example of alcohol derivatives.

Further, as shown in scheme 12, the above compound (41) is reacted by the cross coupling method of Hayashi et al., halogenation of the method of Uemura and the cross coupling method of Hayashi et al, and then the resulting compound can be deprotected to obtain compound (45) as an example of alcohol derivatives.

Compounds of the present invention other than the above-mentioned examples, for example, the compounds substituting hydrogen atoms for fluorine atoms in aromatic rings, can be produced by the above methods or combinations of these methods.

The liquid crystalline compounds of the present invention obtained by the above methods have excellent compatibility with other liquid crystal materials and a high transition temperature of an isotropic phase, and an increase in viscosity is not found by introduction of substituted alkyl groups. Since they have excellent stability, these compounds can be used as excellent ingredients constituting the nematic liquid crystal compositions.

Hitherto, it is known that, when the hydrogen atoms in molecules of a liquid crystalline compound are substituted by fluorine atoms, there are disadvantages that the transition temperature of an isotropic phase is lowered and the viscosity is increased as shown in the following:

Since the compounds wherein R is an alkenyl group show a large elastic constant ratio (bend elastic constant/splay elastic constant), and the change of transmission is steep, the compounds are preferred in a STN type of liquid crystal compositions.

| | NI (° C.)[1] | η (mPa · s)[2] |
|---|---|---|
|  | 62.7 | 22.3 |
| 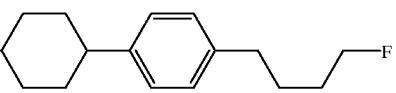 | 61.6 | 24.5 |
| 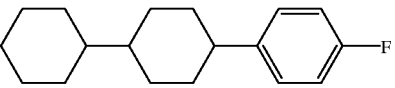 | 82.2 | 26.1 |
| 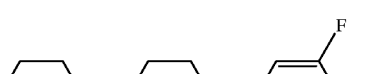 | 77.4 | 27.1 |
|  | 73.0 | 27.3 |

[1]Measurement results after dissolving the compound in liquid crystal composition ZLI-1132 manufactured by Merck Company.
[2]Measurement results at 20° C.

However, in the compounds of the present invention, these disadvantages are not found, and there is the unexpected effect that a high transition temperature of an isotropic phase and low viscosity are maintained and the compatibility is improved.

Since the compounds of the present invention have excellent stability and a high voltage holding ratio, in addition to a TN type and a STN type, in a TFT type of liquid crystal compositions requiring the high voltage holding ratio, the compounds can be preferably used as the ingredients constituting the compositions.

In the compounds of the present invention, the compounds having 3 or 4 cyclohexane rings in a molecule show very high transition temperature of an isotropic phase and small Δn and relatively low viscosity. On the other hand, the compounds having 3 or 4 aromatic rings show large Δn, and the compounds having a pyrimidine ring, pyridine ring or dioxane ring show relatively large Δε. Further, by substituting fluorine atoms for hydrogen atoms, it is possible to improve Δε and the compatibility.

Moreover, where X denotes F, Cl, Br, I or OH, F is specifically preferred for imparting stability and viscosity.

As shown in the above, by selecting any six-membered rings, substituting groups and/or bonding groups, new liquid crystalline compounds having desired physical properties may be obtained.

The liquid crystal compositions provided by the present invention may be the first constituent containing at least one kind of the liquid crystalline compounds represented by the general formula (1), and in addition, as the second constituent, a mixture of at least one kind of the compounds selected from the group of aforesaid general formulas (2), (3) and (4) (designated as the second 2A constituent) and/or at least one kind of the compounds selected from the group of aforesaid general formulas (5), (6), (7), (8) and (9) (designated as the second 2B constituent) is preferred. Further, to adjust a threshold voltage, a temperature range of the liquid crystal phase, the refractive index anisotropy value, the dielectric anisotropy value, viscosity and the like, known compounds may be mixed as the third constituent.

In the above-mentioned second 2A constituent, the following compounds (2-1)–(2-15) preferably contained in general formula (2), the following compounds (3-1)–(3-48) preferably contained in general formula (3), and the following compounds (4-1)–(4-55) preferably contained in general formula (4) can be exemplified, respectively.
 (2-1)
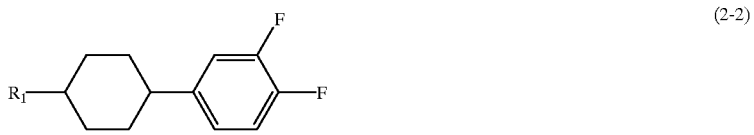 (2-2)
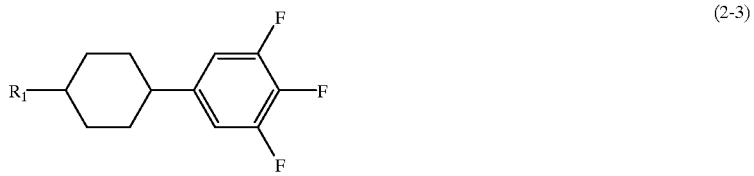 (2-3)
 (2-4)
 (2-5)
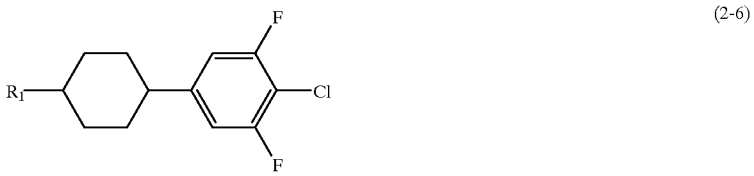 (2-6)
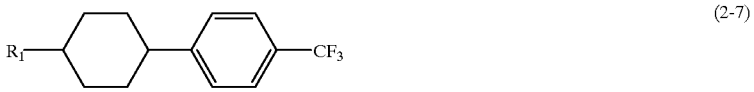 (2-7)
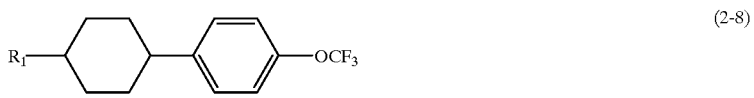 (2-8)
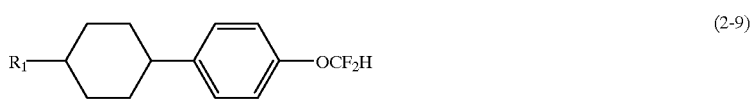 (2-9)
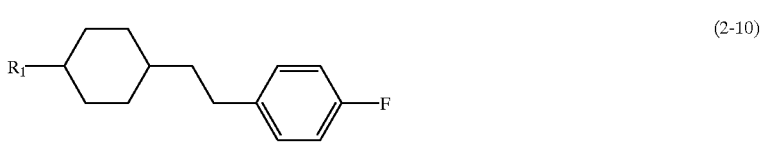 (2-10)
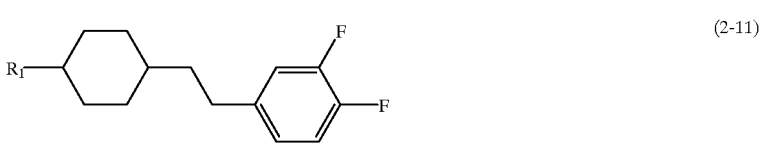 (2-11)

-continued
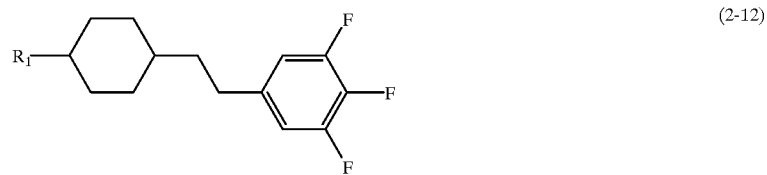 (2-12)
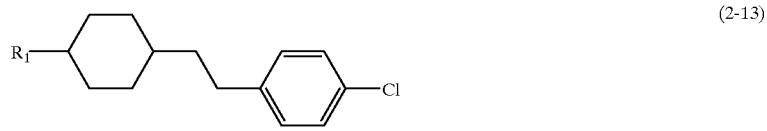 (2-13)
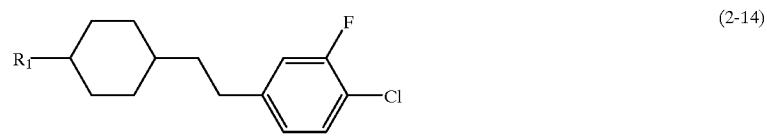 (2-14)
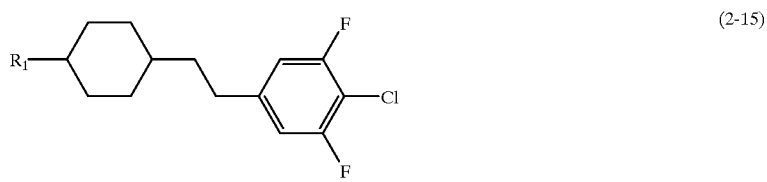 (2-15)
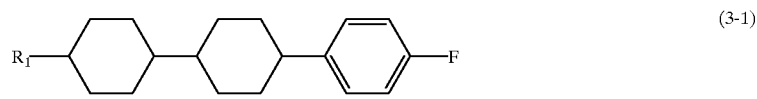 (3-1)
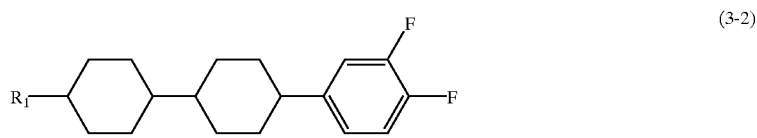 (3-2)
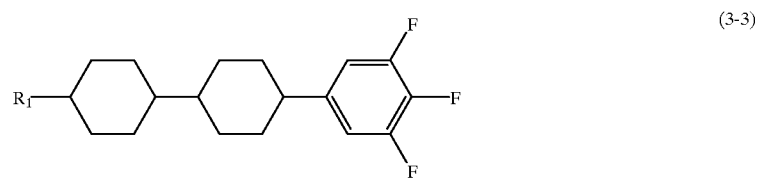 (3-3)
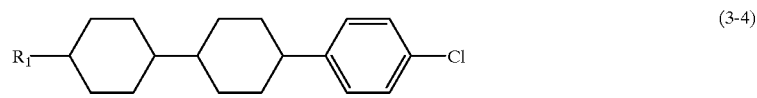 (3-4)
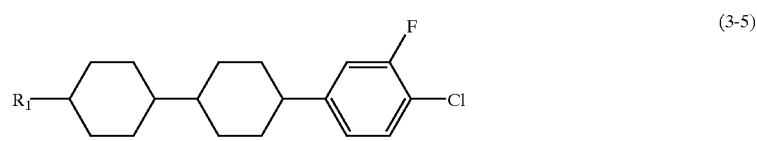 (3-5)
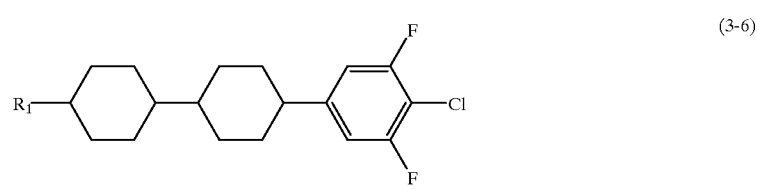 (3-6)

-continued
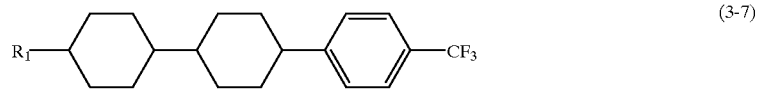 (3-7)
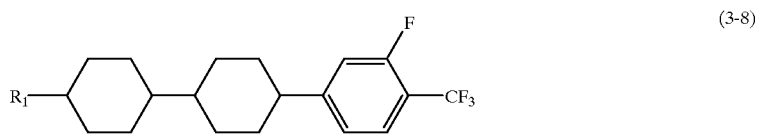 (3-8)
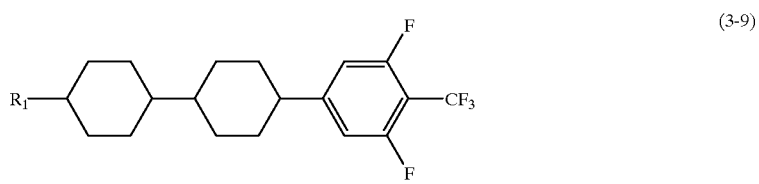 (3-9)
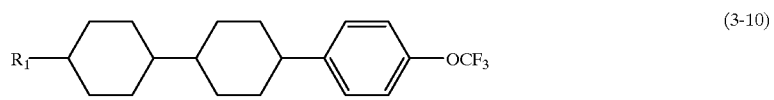 (3-10)
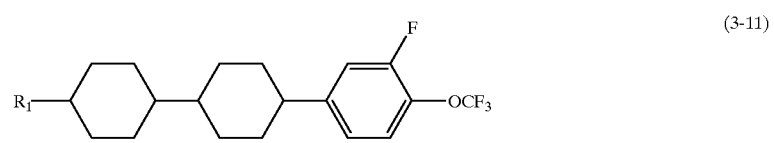 (3-11)
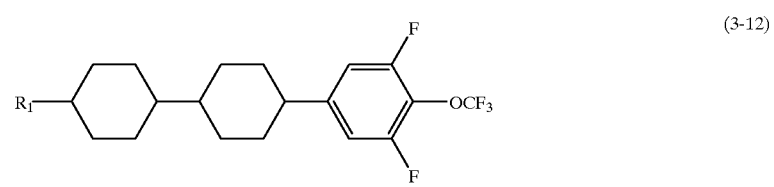 (3-12)
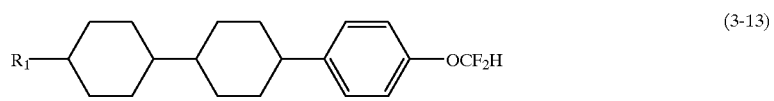 (3-13)
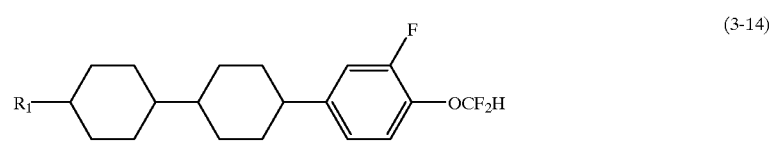 (3-14)
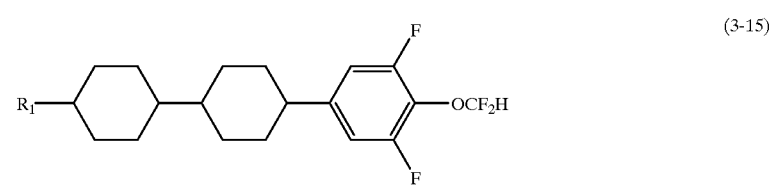 (3-15)
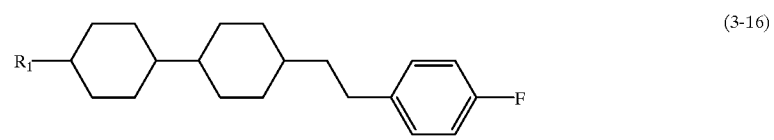 (3-16)

-continued
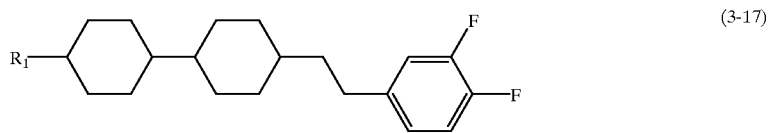 (3-17)
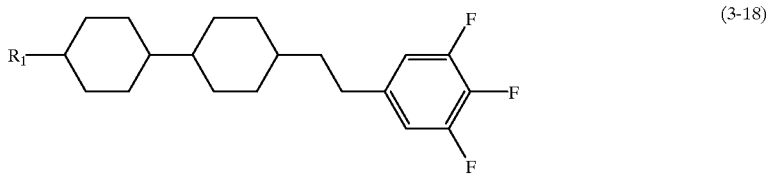 (3-18)
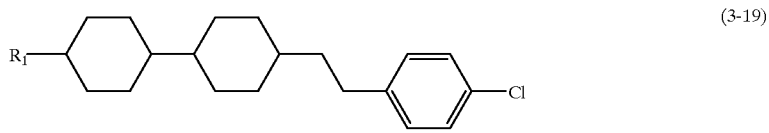 (3-19)
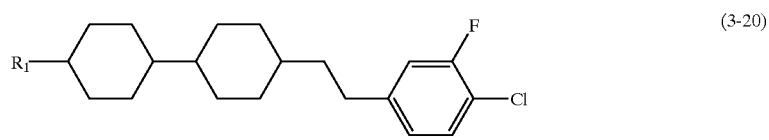 (3-20)
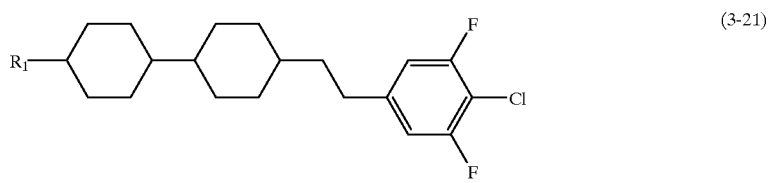 (3-21)
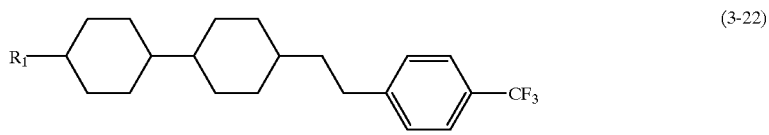 (3-22)
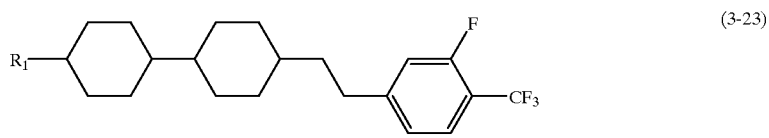 (3-23)
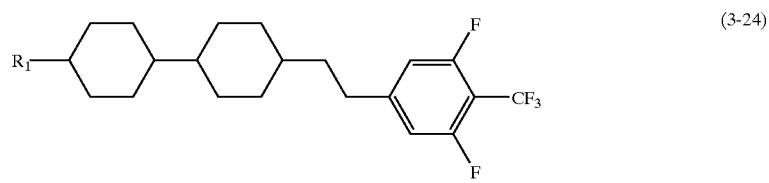 (3-24)
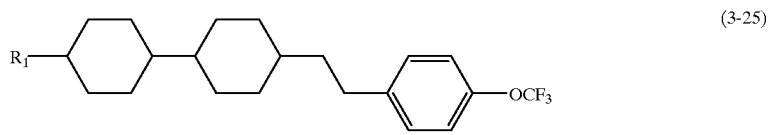 (3-25)
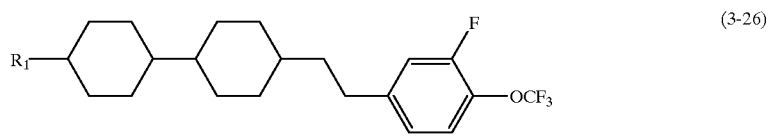 (3-26)

-continued
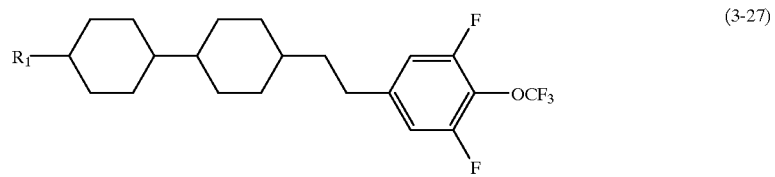
(3-27)
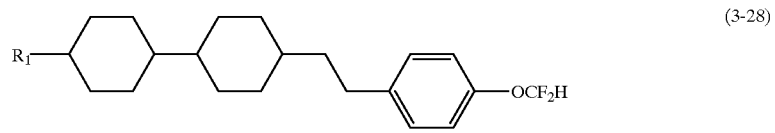
(3-28)
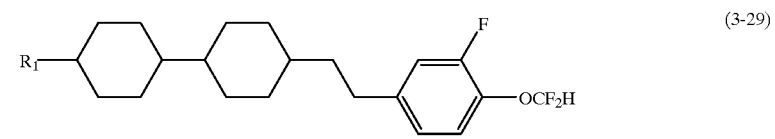
(3-29)
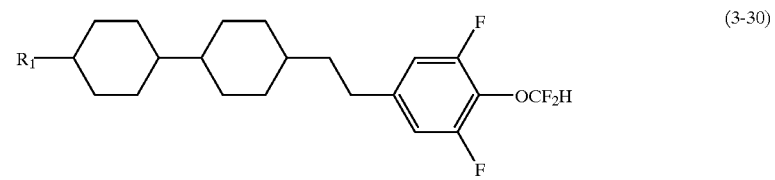
(3-30)
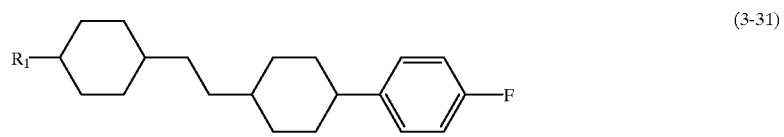
(3-31)
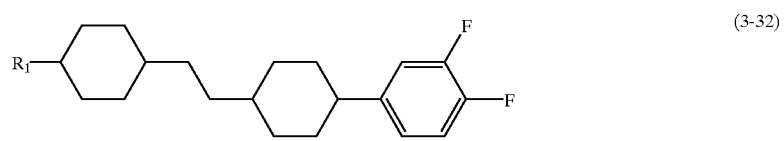
(3-32)
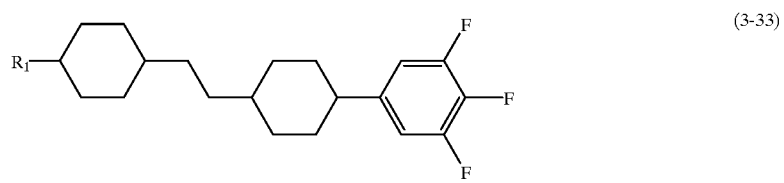
(3-33)
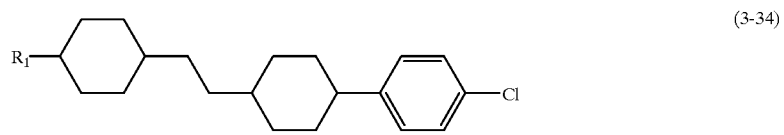
(3-34)
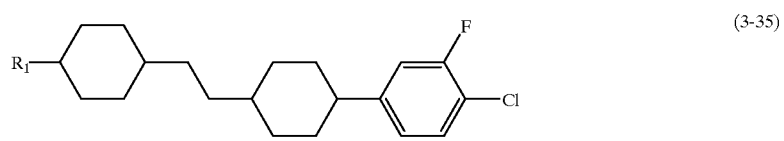
(3-35)

-continued
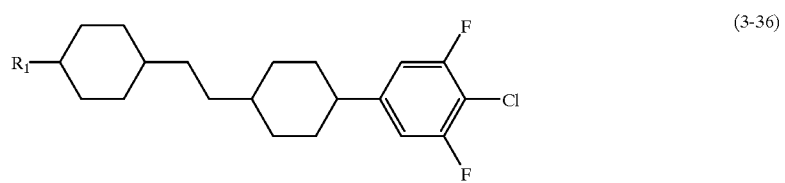
(3-36)
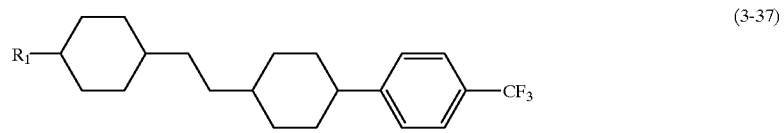
(3-37)
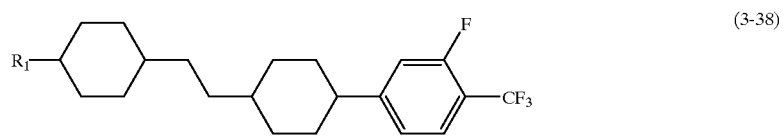
(3-38)
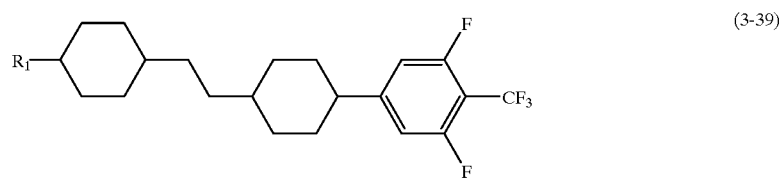
(3-39)
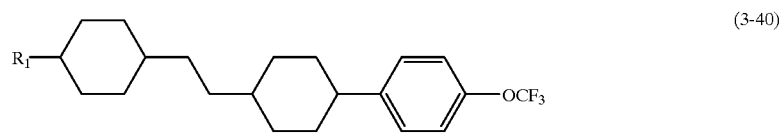
(3-40)
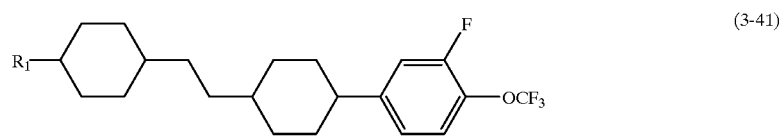
(3-41)
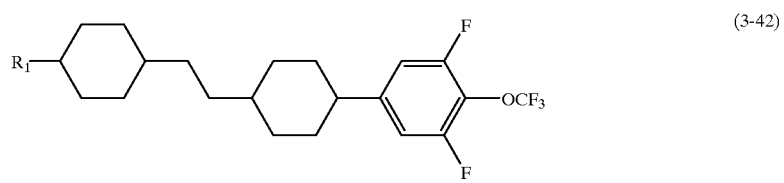
(3-42)
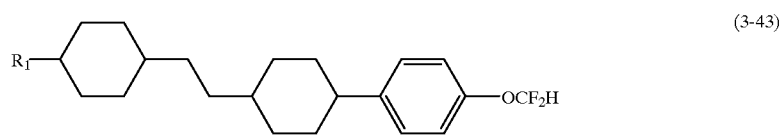
(3-43)
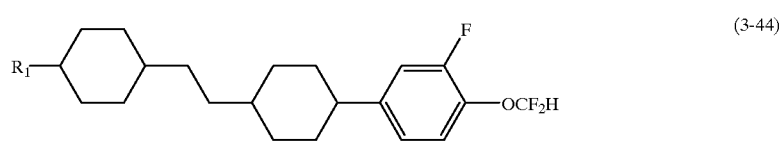
(3-44)

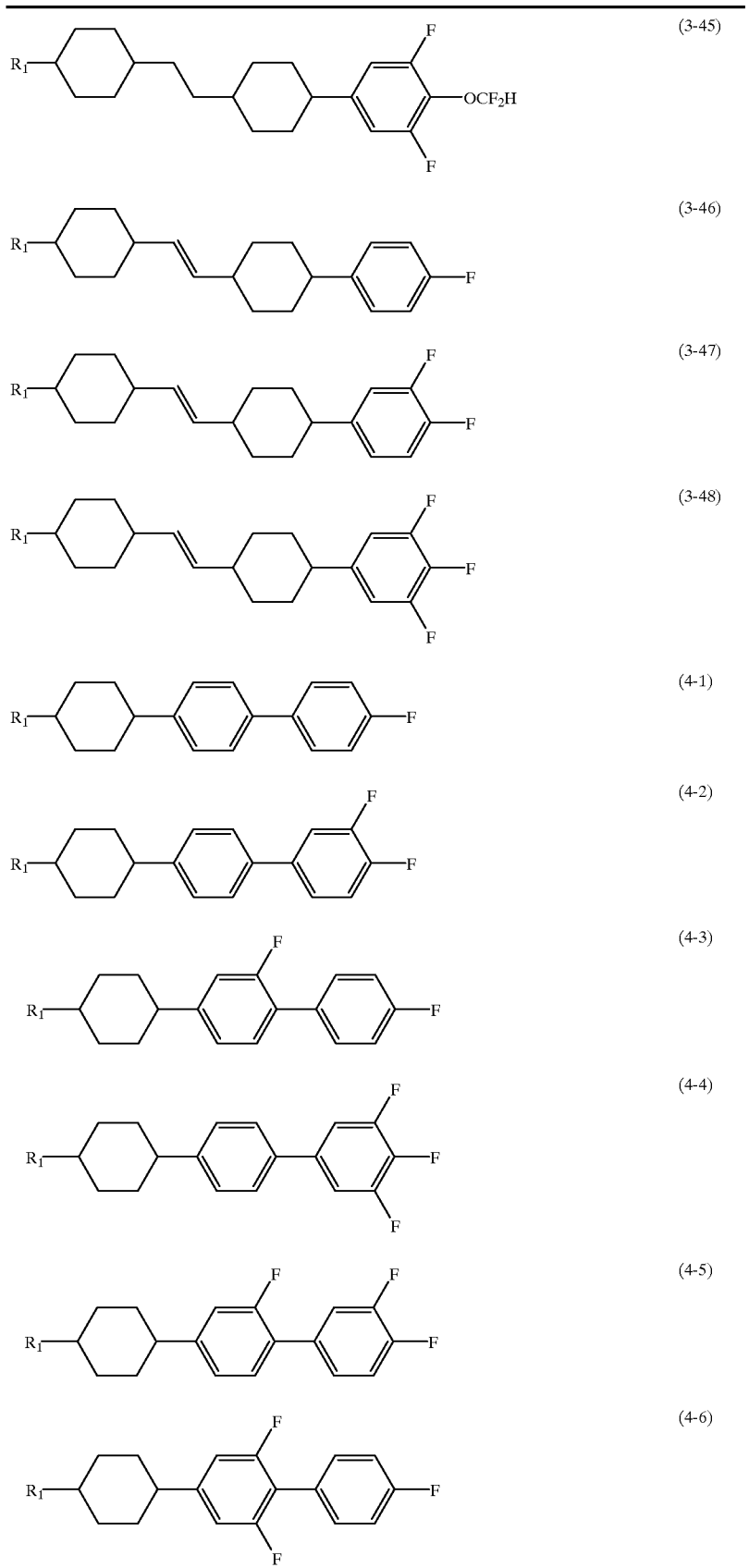

-continued
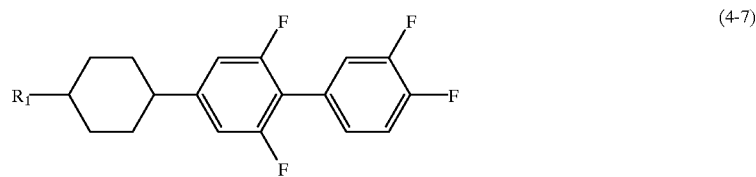 (4-7)
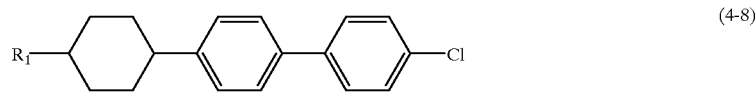 (4-8)
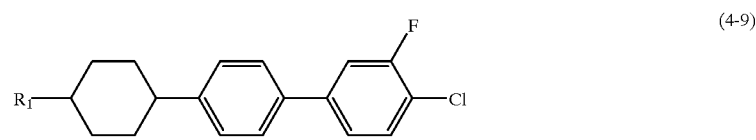 (4-9)
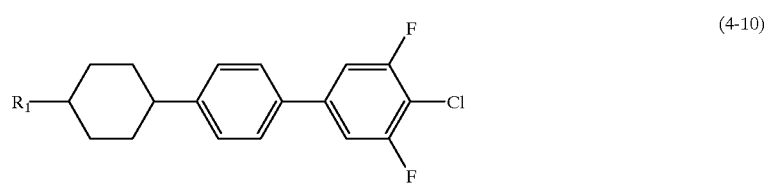 (4-10)
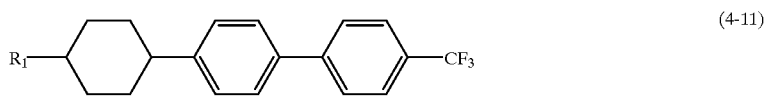 (4-11)
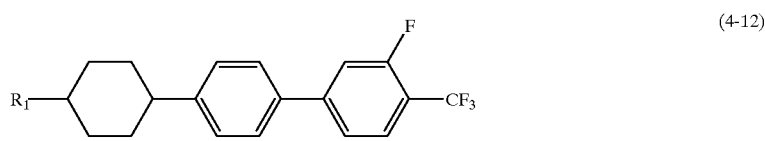 (4-12)
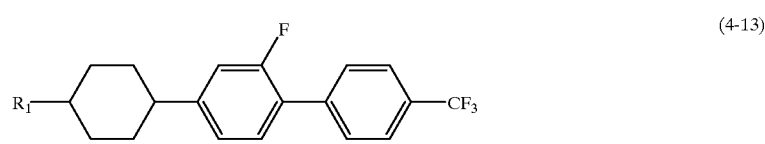 (4-13)
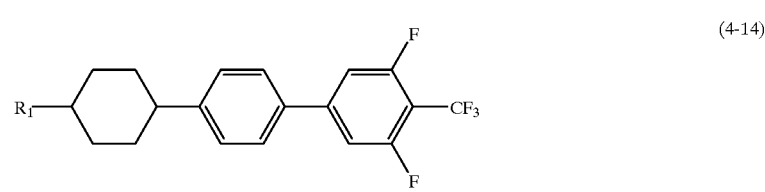 (4-14)
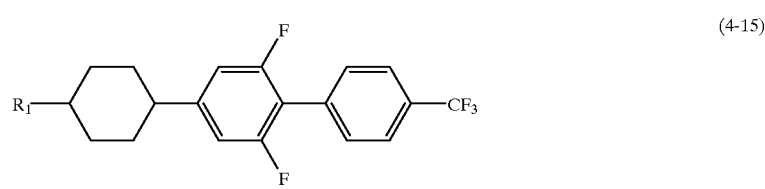 (4-15)
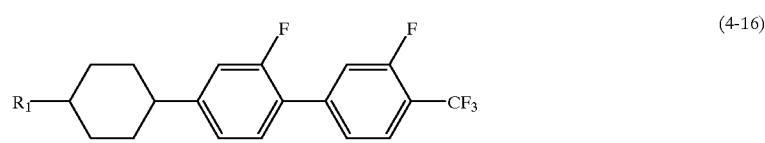 (4-16)

-continued
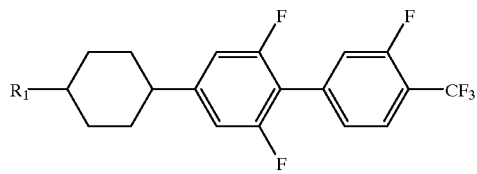
(4-17)
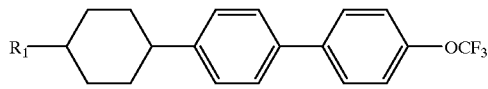
(4-18)
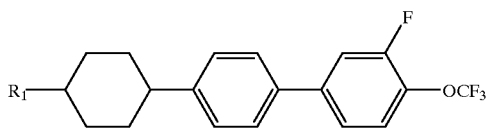
(4-19)
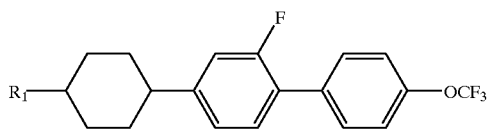
(4-20)
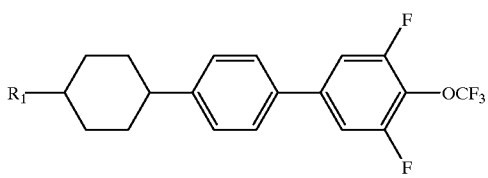
(4-21)
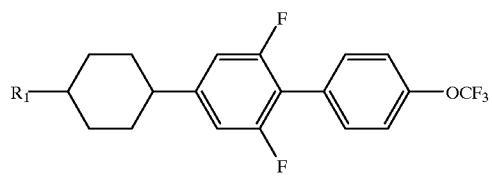
(4-22)
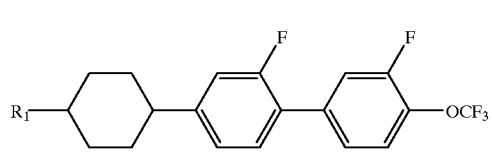
(4-23)
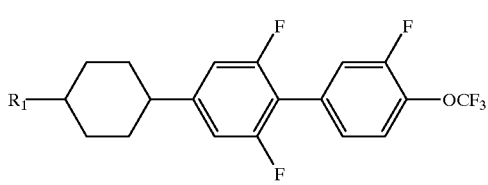
(4-24)
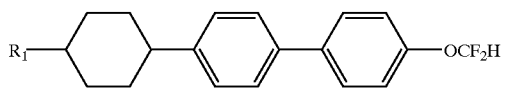
(4-25)
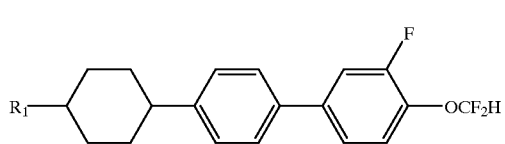
(4-26)

-continued
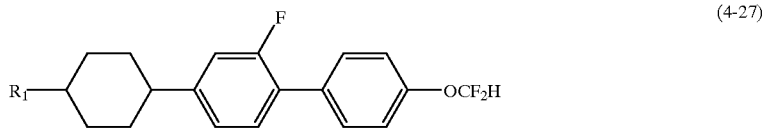
(4-27)
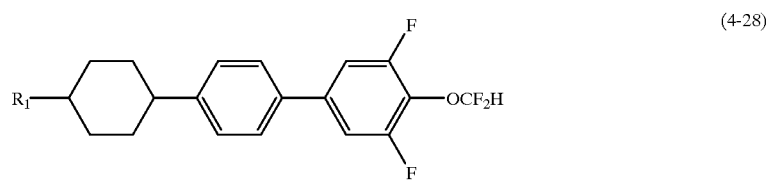
(4-28)
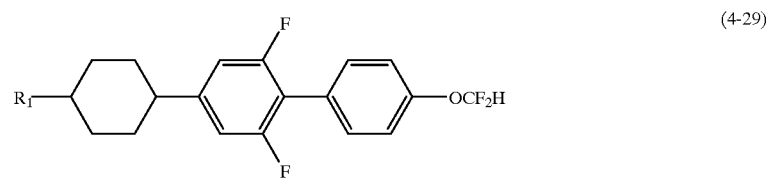
(4-29)
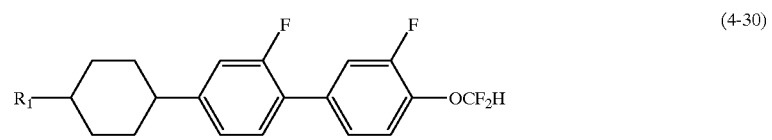
(4-30)
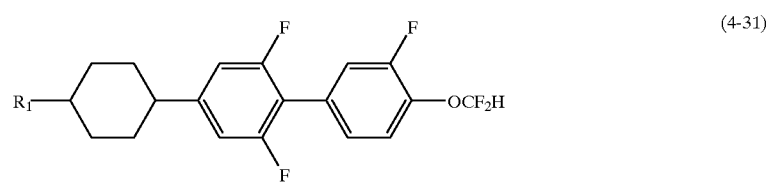
(4-31)
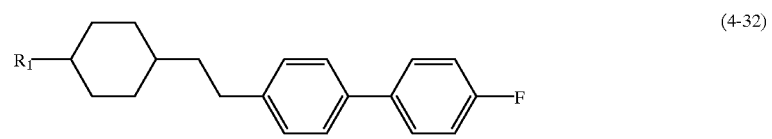
(4-32)
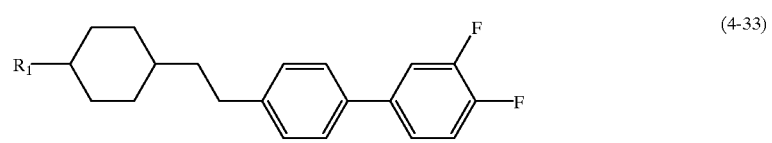
(4-33)
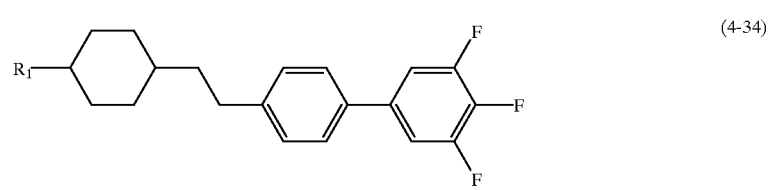
(4-34)
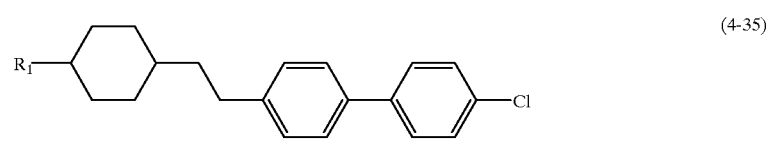
(4-35)

-continued
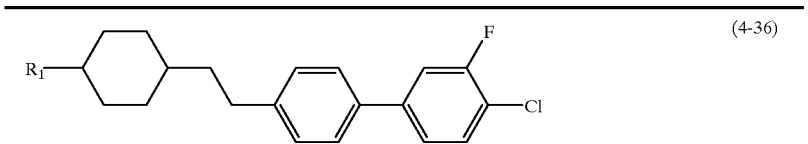
(4-36)
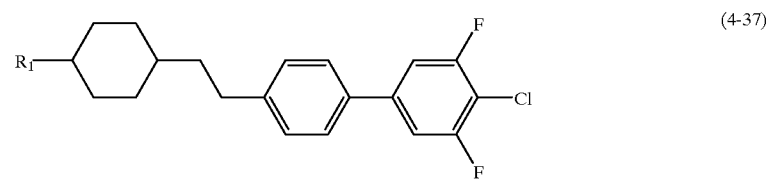
(4-37)
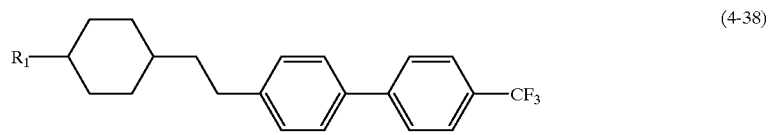
(4-38)
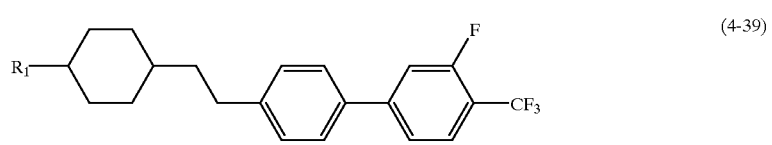
(4-39)
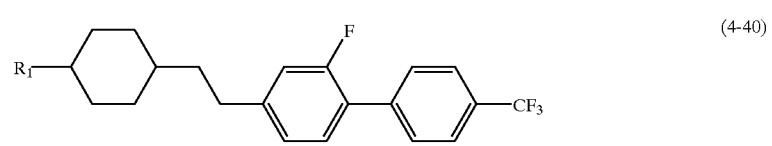
(4-40)
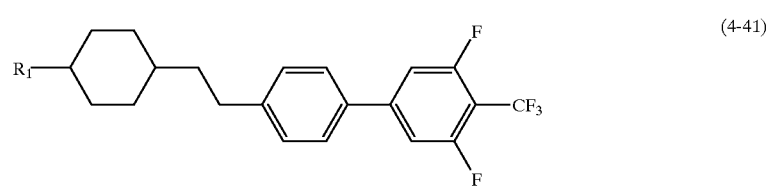
(4-41)
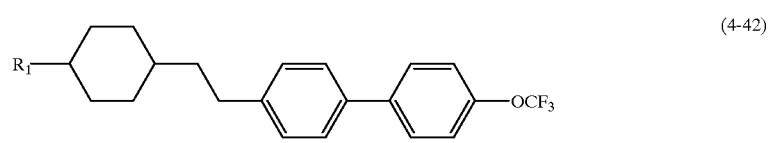
(4-42)
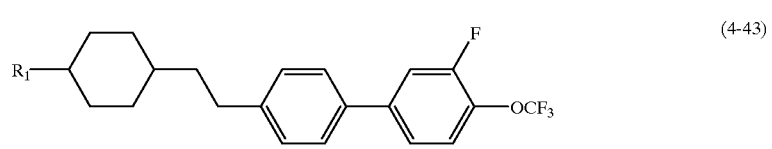
(4-43)
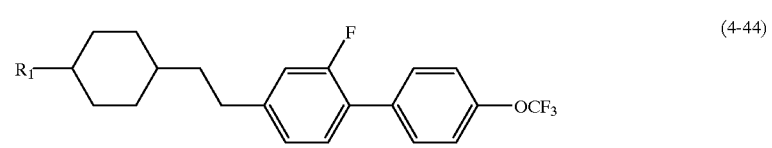
(4-44)
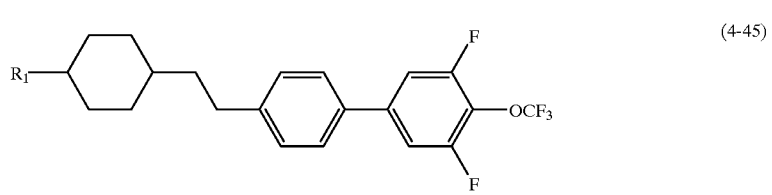
(4-45)

-continued
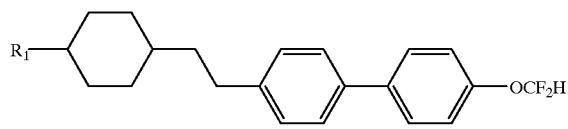 (4-46)
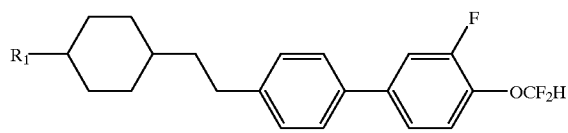 (4-47)
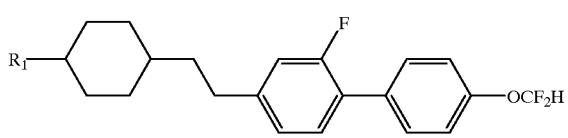 (4-48)
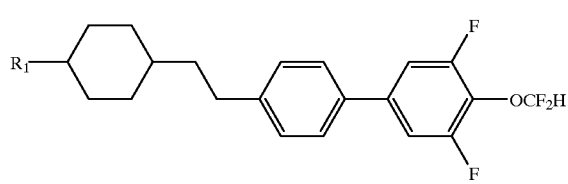 (4-49)
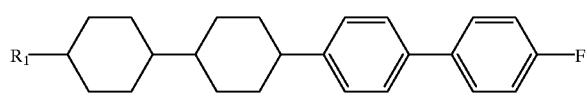 (4-50)
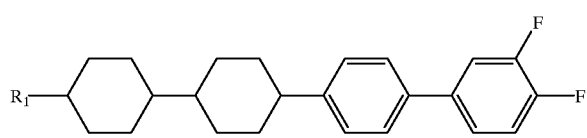 (4-51)
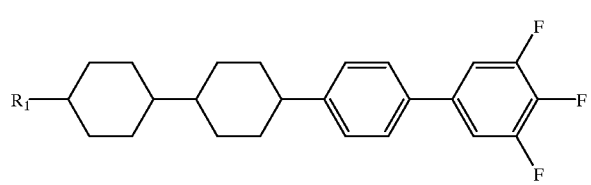 (4-52)
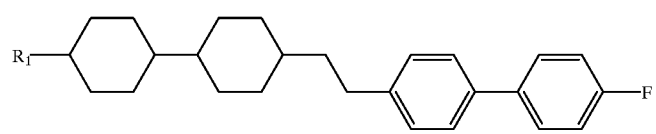 (4-53)
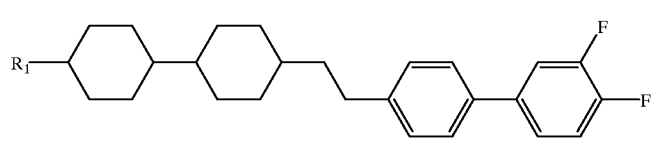 (4-54)
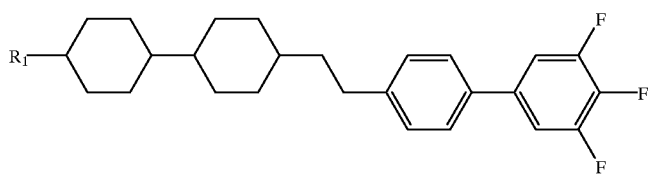 (4-55)

These compounds represented by general formula (2)-(4) have positive dielectric anisotropy value and excellent thermostability and chemical stability.

The usage of the compounds is suitably 1–99% by weight based on the total weight of the liquid crystal composition, preferably 10–97% by weight, and more preferably 40–95% by weight.

Moreover, in the above-mentioned second 2B constituents, as preferred compounds contained in general formulas (5), (6) and (7), (5-1)–(5-24), (6-1)–(6-3) and (7-1)–(7-17) can be exemplified.

(5-1)

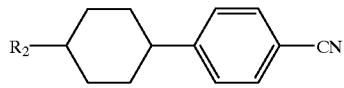

(5-2)

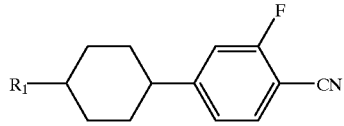

(5-3)

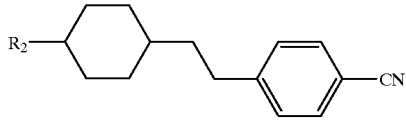

(5-4)

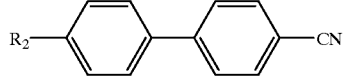

(5-5)

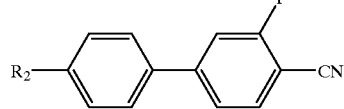

(5-6)

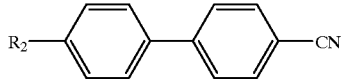

(5-7)

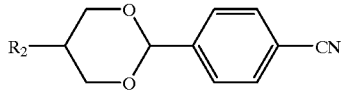

(5-8)

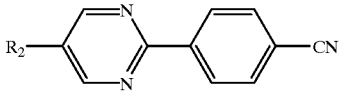

(5-9)

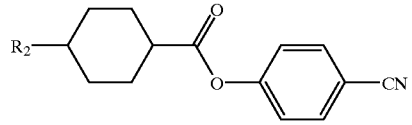

(5-10)

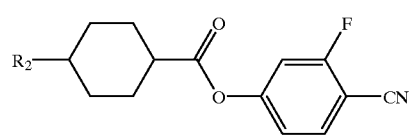

(5-11)

-continued
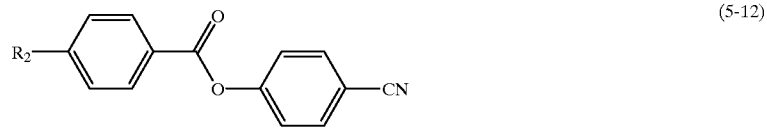 (5-12)
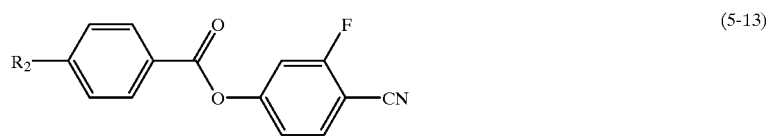 (5-13)
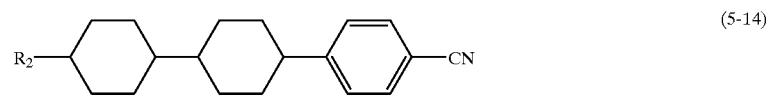 (5-14)
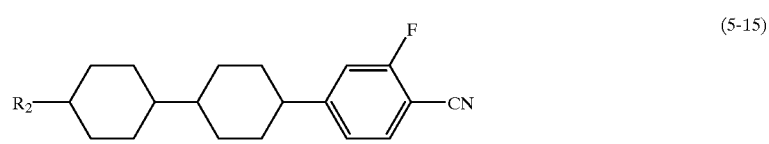 (5-15)
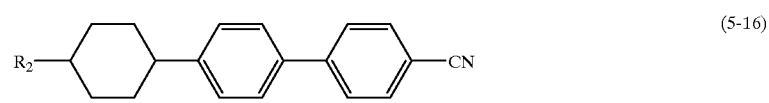 (5-16)
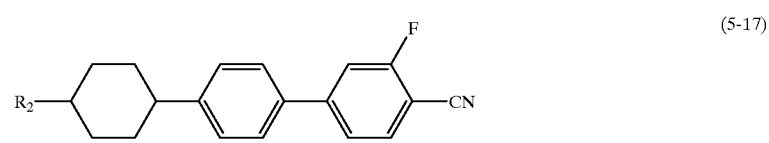 (5-17)
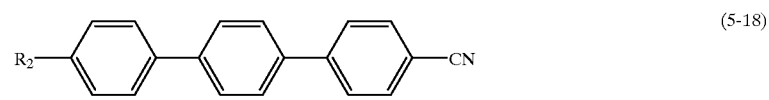 (5-18)
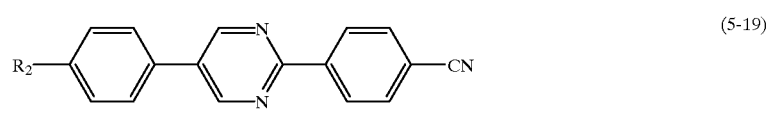 (5-19)
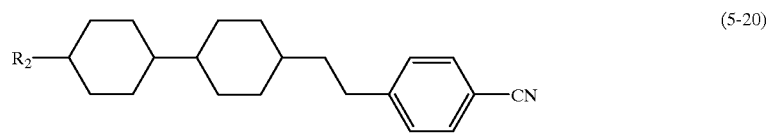 (5-20)
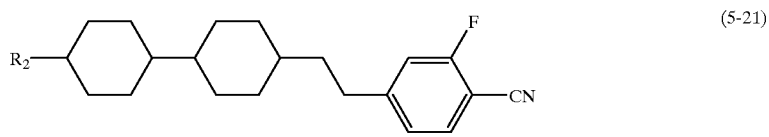 (5-21)
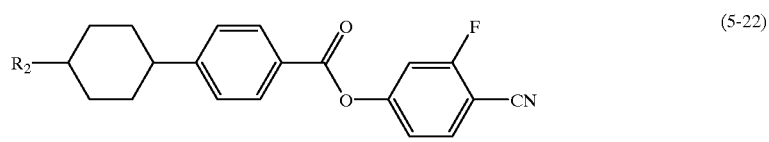 (5-22)

-continued
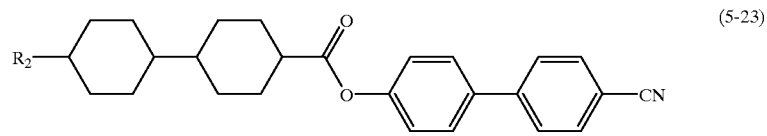 (5-23)
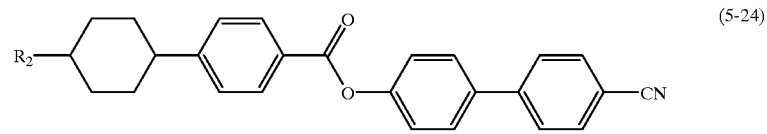 (5-24)
 (6-1)
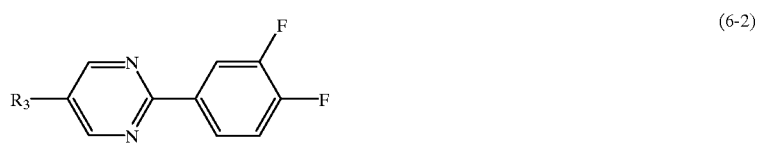 (6-2)
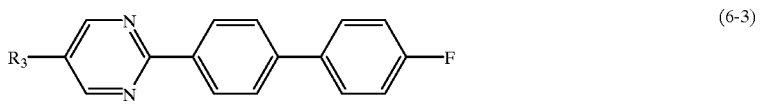 (6-3)
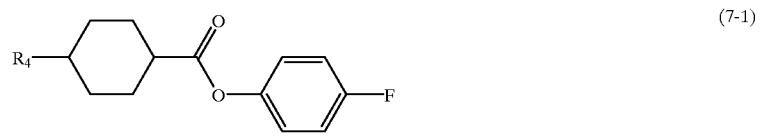 (7-1)
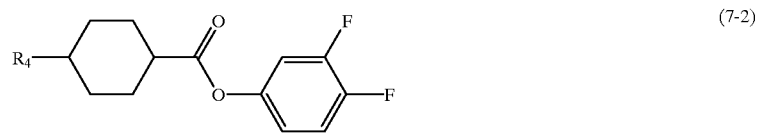 (7-2)
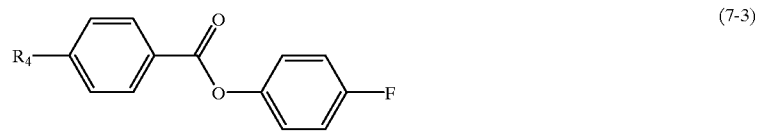 (7-3)
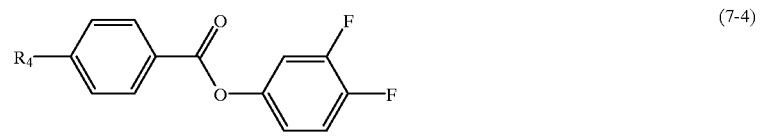 (7-4)
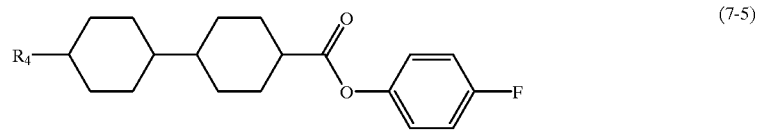 (7-5)
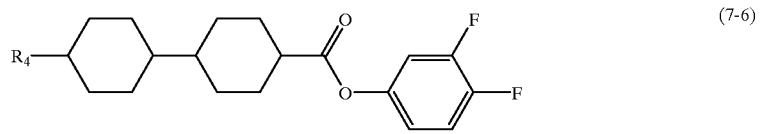 (7-6)

-continued
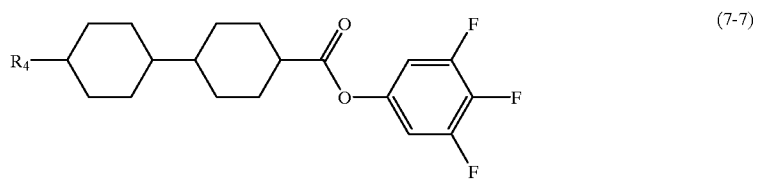 (7-7)
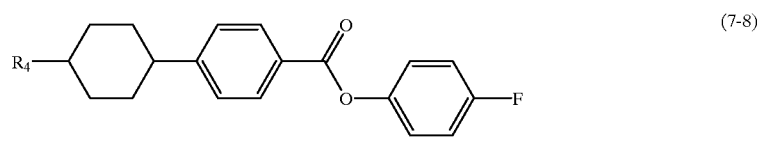 (7-8)
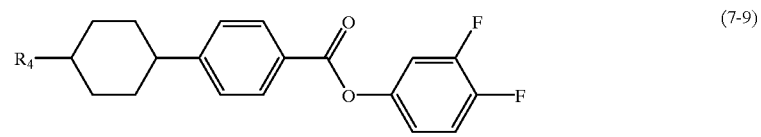 (7-9)
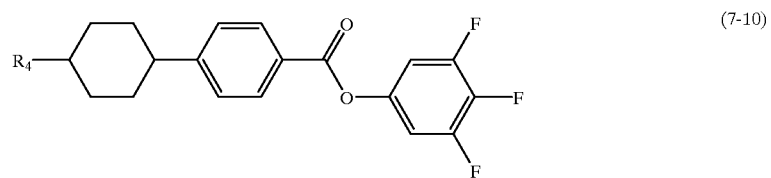 (7-10)
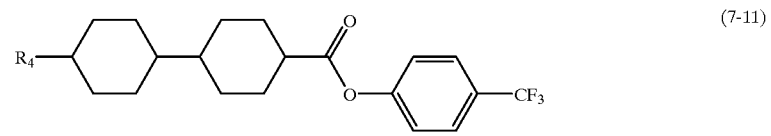 (7-11)
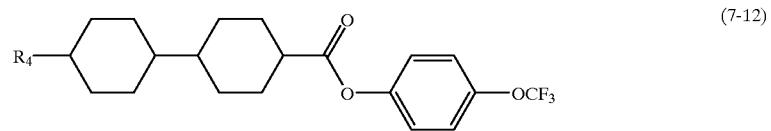 (7-12)
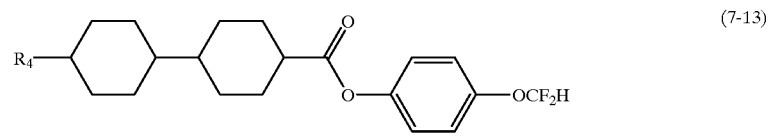 (7-13)
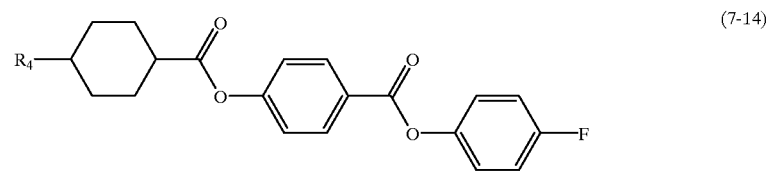 (7-14)
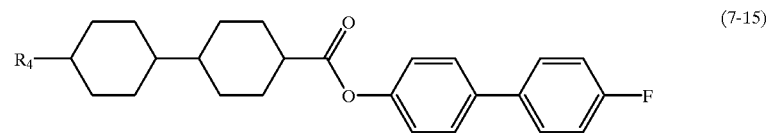 (7-15)
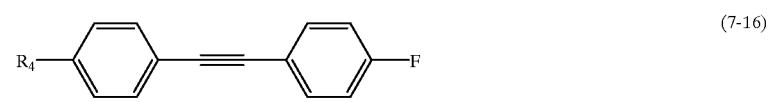 (7-16)

-continued

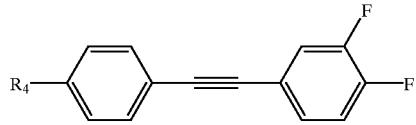
(7-17)

The compounds represented by general formulas (5)-(7) have a positive and high dielectirc anisotropy value and can be particularly used as a constituent of the composition to reduce the threshold voltage. In addition, these compounds are used to adjust the viscosity and the refractive index anisotropy value, to spread the region of temperature of the liquid crystal phase and to improve the steepness properties.

In the second 2B constituent, (8-1)–(8-8) and (9-1)–(9-12) can be exemplified as preferred embodiments of the compounds contained in general formulas (8) and (9), respectively.

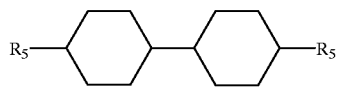
(8-1)

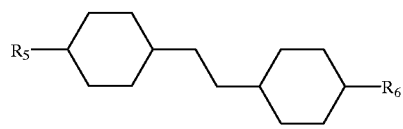
(8-2)

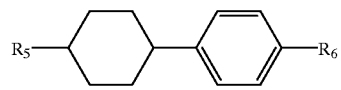
(8-3)

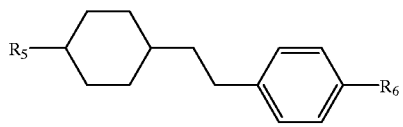
(8-4)

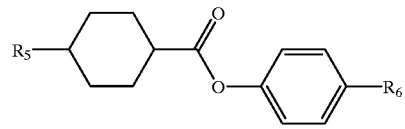
(8-5)

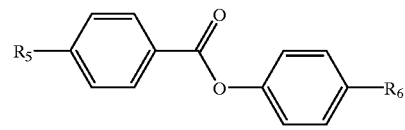
(8-6)

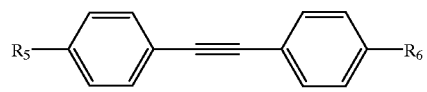
(8-7)

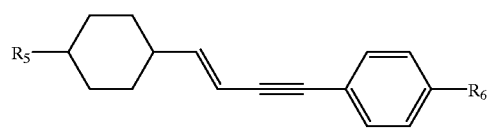
(8-8)

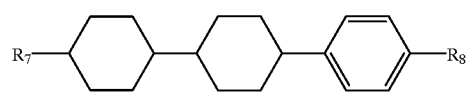
(9-1)

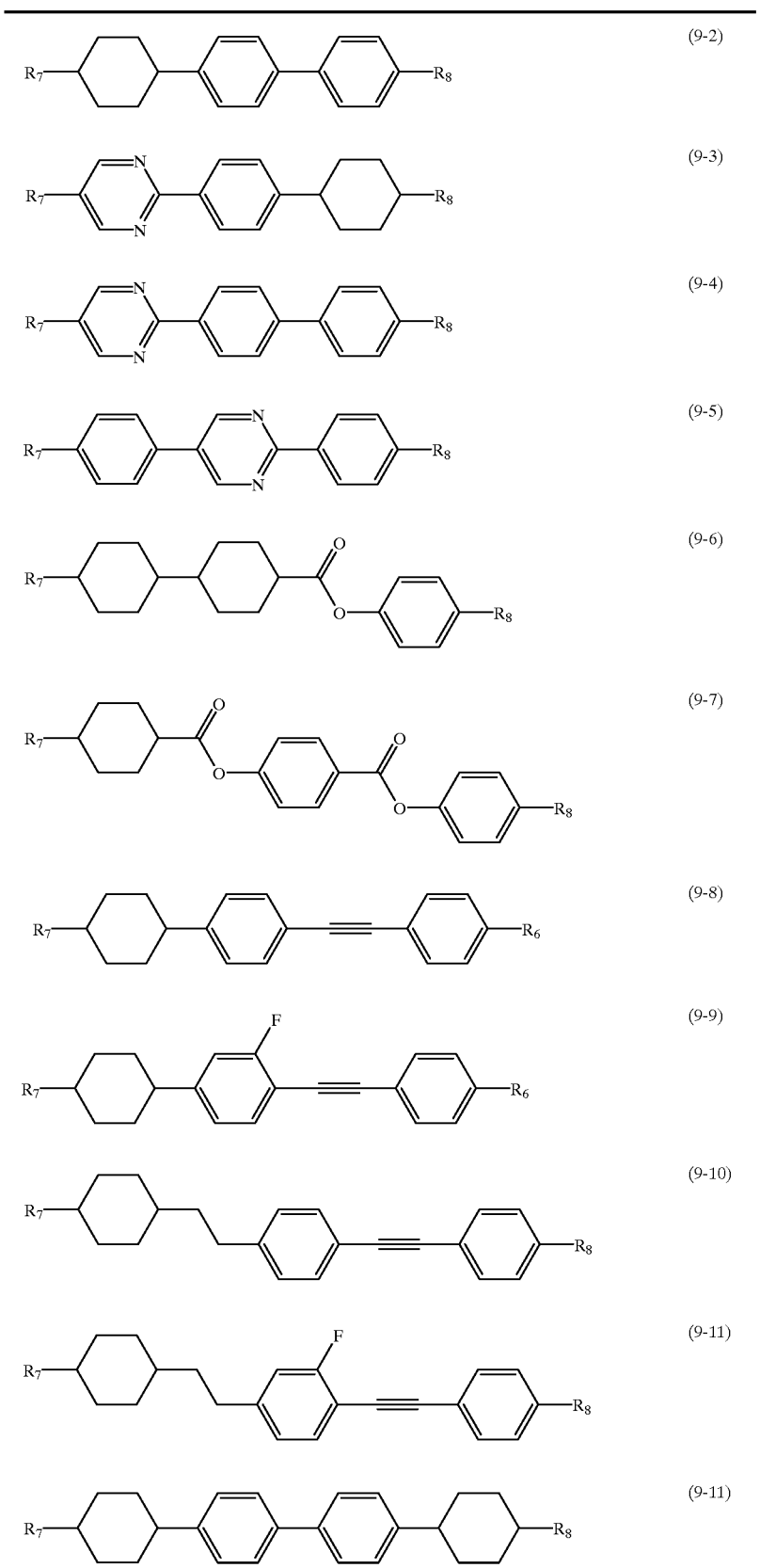

-continued

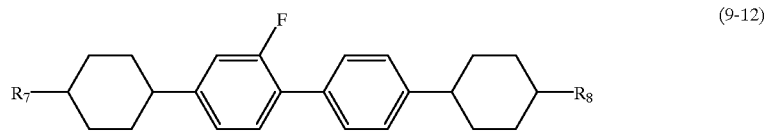

(9-12)

These compounds represented by general formulas (8) and (9) have a negative or week positive dielectric anisotropy value. In these compounds, the compound represented by general formula (8) is used as a constituent of the composition for lowering the viscosity and for regulation of the dielectric anisotropy value, and the compound represented by general formula (9) is used for spreading the region of temperature of the liquid crystal phase and/or for regulation of the dielectric anisotropy value.

The compounds represented by the above general formulas (5)-(9) are compounds necessary to prepare liquid crystal compositions for a display mode of a STN type or a common display mode of a TN type. In case of preparation of common display modes of the STN type or the TN type, suitable usage of the compound is 1–99% by weight based on the total weight of the liquid crystal composition, preferably 10–97% by weight, and more preferably 40–95% by weight.

The liquid crystal composition provided by the present invention contains preferably 0.1–99% by weight of at least one kind of liquid crystalline compounds represented by general formula (1) to develop good characteristics.

The liquid crystal composition can be commonly prepared by methods, for example by a method wherein many kinds of constituents are dissolved in each other at a high temperature. If necessary, suitable additives are added to improve and optimize according to the demand of desired use. Such additives are well-known by persons concerned in the field, and described in detail in literature and the like. Usually, a chiral dopant and the like are added. The agent has properties that the helical structure of liquid crystals is induced to adjust a necessary twisted angle and prevented a reverse twist.

When dichroic dyes such as merocyanine series, styryl series, azo series, azomethine series, azoxy series, quinophthalone series, anthraquinone series and tetrazine series are added, the composition can be used as a liquid crystal composition for a GH mode. The composition of the present invention can be used for NCAP, which is prepared by microcapsulation of a nematic liquid crystal, or the composition can be used for a device of polymer-dispersion type liquid crystal display (PDLCD) which is prepared by working three dimensional crosslinked polymer in liquid crystal, for example, a device of polymer network liquid crystal display (PNLCD), further, for an electrically controlled birefringence (ECB) mode and a DS mode.

The following show examples of liquid crystal compositions containing the compounds of the present invention. The numbers of the compounds are the same as the numbers represented in after-mentioned examples.

Composition example 1

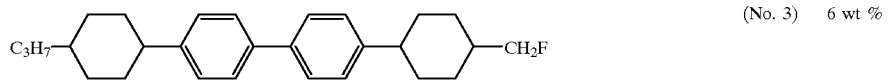  (No. 3)  6 wt %

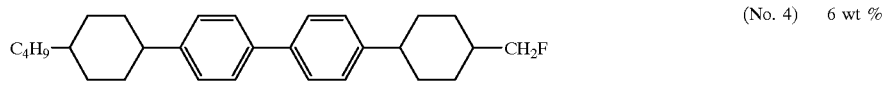  (No. 4)  6 wt %

  (No. 5)  6 wt %

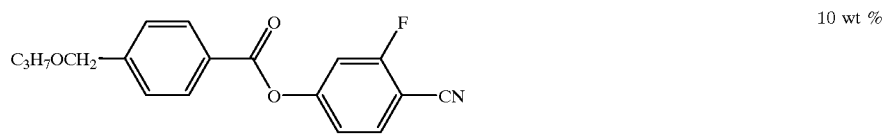  10 wt %

  10 wt %

-continued

| Composition example 1 | |
|---|---|
| C₃H₇–⟨Cy⟩–⟨Ph⟩–OC₂H₅ | 3 wt % |
| C₂H₅–⟨Ph⟩–C≡C–⟨Ph⟩–OCH₃ | 10 wt % |
| C₃H₇–⟨Ph⟩–C≡C–⟨Ph⟩–OCH₃ | 10 wt % |
| C₄H₉–⟨Ph⟩–C≡C–⟨Ph⟩–OCH₃ | 10 wt % |
| C₃H₇–⟨Cy⟩–⟨Cy⟩–⟨Ph⟩–OCH₃ | 3 wt % |
| C₃H₇–⟨Cy⟩–CH₂CH₂–⟨Ph⟩–C≡C–⟨Ph⟩–C₂H₅ | 2 wt % |
| C₃H₇–⟨Cy⟩–CH₂CH₂–⟨Ph⟩–C≡C–⟨Ph⟩–C₃H₇ | 3 wt % |
| C₃H₇–⟨Cy⟩–⟨Ph(F)⟩–C≡C–⟨Ph⟩–C₂H₅ | 4 wt % |
| C₃H₇–⟨Cy⟩–⟨Ph(F)⟩–C≡C–⟨Ph⟩–C₃H₇ | 4 wt % |
| C₃H₇–⟨Cy⟩–⟨Ph(F)⟩–C≡C–⟨Ph⟩–C₄H₉ | 4 wt % |
| C₃H₇–⟨Cy⟩–⟨Ph⟩–⟨Pyrimidine⟩–C₂H₅ | 6 wt % |
| C₃H₇–⟨Cy⟩–⟨Ph⟩–⟨Pyrimidine⟩–C₃H₇ | 3 wt % |

| Composition example 2 | | |
|---|---|---|
| C₃H₇—[Cy]—[Ph]—[Ph]—[Cy]—CH₂F | (No. 3) | 6 wt % |
| C₄H₉—[Cy]—[Ph]—[Ph]—[Cy]—CH₂F | (No. 4) | 6 wt % |
| C₅H₁₁—[Cy]—[Ph]—[Ph]—[Cy]—CH₂F | (No. 5) | 4 wt % |
| CH₂=C₃H₅—[Cy]—[Ph]—CN | | 8 wt % |
| C₂H₄=C₃H₅—[Cy]—[Ph]—CN | | 8 wt % |
| C₃H₇—[Cy]—[Ph]—CN | | 14 wt % |
| CH₃OCH₂—[Cy]—[Ph]—CN | | 8 wt % |
| C₂H₅OCH₂—[Cy]—[Ph]—CN | | 4 wt % |
| C₃H₇—[Cy]—[Cy]—C₄H₉ | | 8 wt % |
| CH₃OCH₂—[Cy]—[Cy]—C₅H₁₁ | | 6 wt % |
| C₂H₅—[Ph]—C≡C—[Ph]—OCH₃ | | 8 wt % |
| C₂H₅—[Cy]—[Cy]—[Ph]—CN | | 5 wt % |
| C₃H₇—[Cy]—[Cy]—[Ph]—CN | | 4 wt % |
| C₃H₇—[Cy]—[Cy]—[Ph]—CH₃ | | 6 wt % |

-continued
| Composition example 2 | |
|---|---|
|  | 5 wt % |
10
| Composition example 3 | | |
|---|---|---|
| 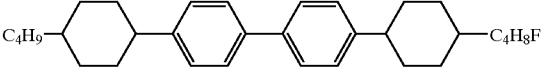 | (No. 1) | 5 wt % |
| 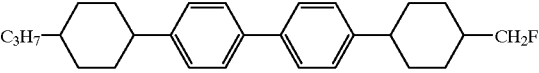 | (No. 3) | 5 wt % |
| 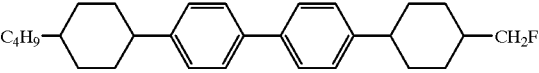 | (No. 4) | 5 wt % |
| 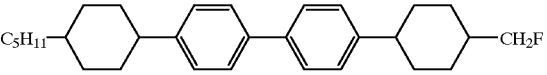 | (No. 5) | 5 wt % |
| 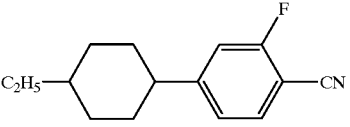 | | 13 wt % |
| 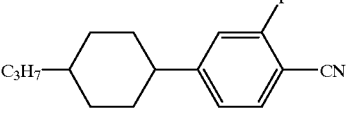 | | 13 wt % |
| 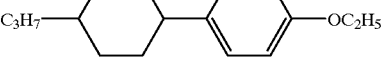 | | 8 wt % |
| 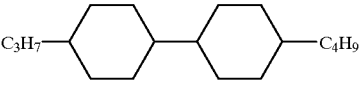 | | 8 wt % |
| 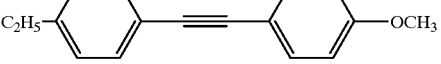 | | 8 wt % |
|  | | 6 wt % |
| 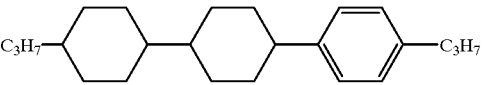 | | 10 wt % |

-continued

| Composition example 3 | |
|---|---|
| C₃H₇–⟨Cy⟩–⟨Cy⟩–⟨Ph⟩–F | 3 wt % |
| C₃H₇–⟨Cy⟩–⟨Ph⟩–⟨Ph⟩–F | 2 wt % |
| C₃H₇–⟨Cy⟩–⟨Cy⟩–⟨Ph⟩–OCH₃ | 3 wt % |
| C₃H₇–⟨Cy⟩–CH₂CH₂–⟨Ph⟩–C≡C–⟨Ph⟩–C₂H₅ | 3 wt % |
| C₃H₇–⟨Cy⟩–CH₂CH₂–⟨Ph⟩–C≡C–⟨Ph⟩–C₃H₇ | 3 wt % |

| Composition example 4 | | |
|---|---|---|
| C₄H₉–⟨Cy⟩–⟨Ph⟩–⟨Ph⟩–⟨Cy⟩–C₄H₈F | (No. 1) | 4 wt % |
| C₃H₇–⟨Cy⟩–⟨Ph⟩–⟨Ph⟩–⟨Cy⟩–CH₂F | (No. 3) | 5 wt % |
| C₄H₉–⟨Cy⟩–⟨Ph⟩–⟨Ph⟩–⟨Cy⟩–CH₂F | (No. 4) | 4 wt % |
| C₃H₇–⟨Cy⟩–⟨Ph(2-F)⟩–⟨Ph⟩–⟨Cy⟩–CH₂F | (No. 38) | 3 wt % |
| C₅H₁₁–⟨Ph⟩–⟨Ph⟩–CN | | 5 wt % |
| F–⟨Ph⟩–⟨Ph⟩–CN | | 2 wt % |
| C₃H₇–⟨Cy⟩–⟨Ph⟩–OC₂H₅ | | 10 wt % |

-continued

| Composition example 4 | |
|---|---|
| C₃H₇—⟨Cy⟩—⟨Ph⟩—OC₄H₉ | 10 wt % |
| C₄H₉—⟨Ph⟩—⟨Pyrimidine⟩—C₃H₇ | 4 wt % |
| C₄H₉—⟨Ph⟩—⟨Pyrimidine⟩—C₄H₉ | 4 wt % |
| C₅H₁₁—⟨Ph⟩—⟨Pyrimidine⟩—C₄H₉ | 4 wt % |
| C₅H₁₁—⟨Ph⟩—⟨Pyrimidine⟩—C₆H₁₃ | 4 wt % |
| C₅H₁₁O—⟨Ph⟩—⟨Pyrimidine⟩—C₆H₁₃ | 4 wt % |
| C₆H₁₃O—⟨Ph⟩—⟨Pyrimidine⟩—C₆H₁₃ | 4 wt % |
| C₇H₁₅O—⟨Ph⟩—⟨Pyrimidine⟩—C₆H₁₃ | 4 wt % |
| C₈H₁₇O—⟨Ph⟩—⟨Pyrimidine⟩—C₆H₁₃ | 4 wt % |
| C₃H₇—⟨Cy⟩—⟨Cy⟩—⟨Ph⟩—CH₃ | 6 wt % |
| C₃H₇—⟨Cy⟩—⟨Cy⟩—⟨Ph⟩—C₃H₇ | 8 wt % |
| C₃H₇—⟨Cy⟩—⟨Cy⟩—⟨Ph⟩—OCH₃ | 3 wt % |
| C₂H₅—⟨Cy⟩—⟨Cy⟩—⟨Ph⟩—OCH₃ | 4 wt % |

-continued
Composition example 4
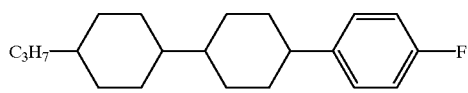 4 wt %
10
Composition example 5
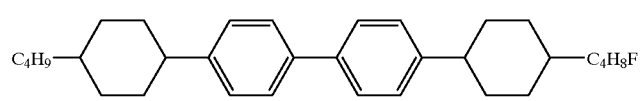 (No. 1) 4 wt %
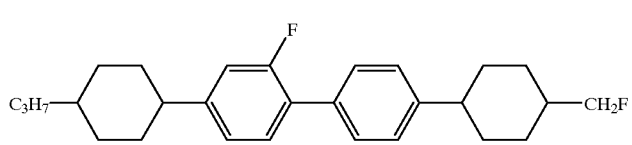 (No. 38) 4 wt %
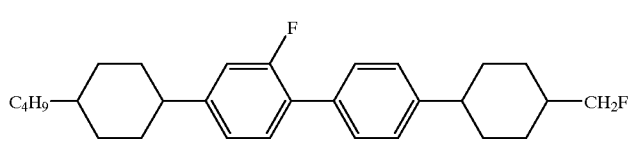 (No. 40) 4 wt %
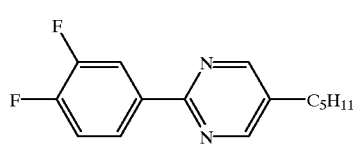 10 wt %
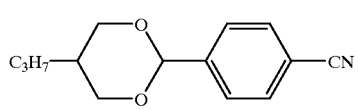 10 wt %
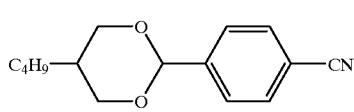 10 wt %
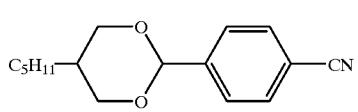 8 wt %
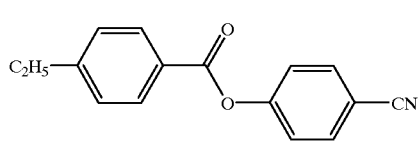 10 wt %
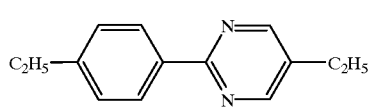 2 wt %

-continued
| Composition example 5 | |
|---|---|
| 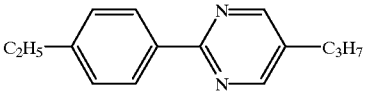 | 2 wt % |
| 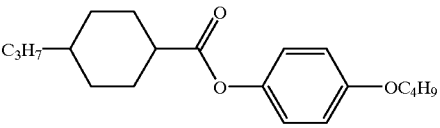 | 3 wt % |
| 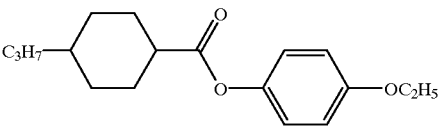 | 3 wt % |
| 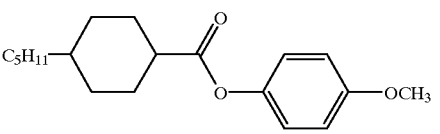 | 3 wt % |
| 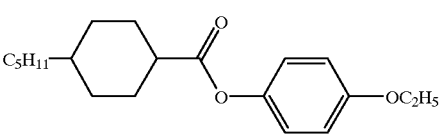 | 3 wt % |
| 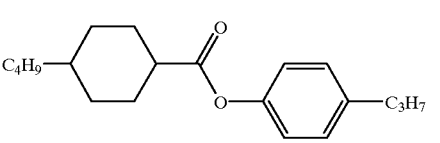 | 2 wt % |
| 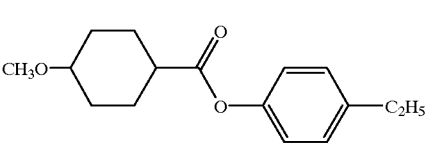 | 2 wt % |
| 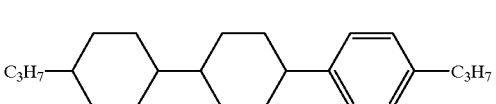 | 10 wt % |
| 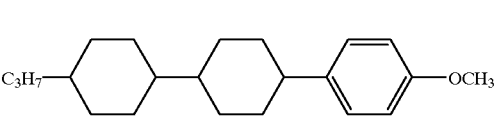 | 4 wt % |
| 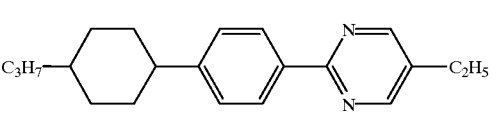 | 2 wt % |
| 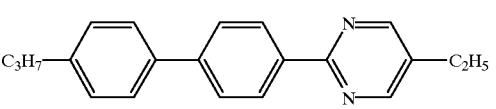 | 2 wt % |

| -continued |||
|---|---|---|
| Composition example 5 |||
| 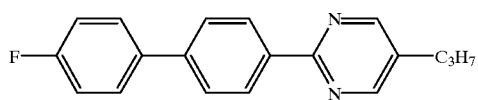 | | 2 wt % |
| Composition example 6 |||
|---|---|---|
| 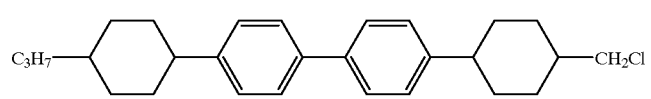 | (No. 27) | 4 wt % |
| 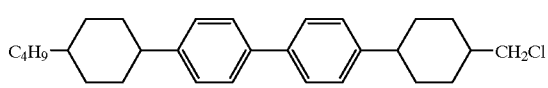 | (No. 28) | 3 wt % |
| 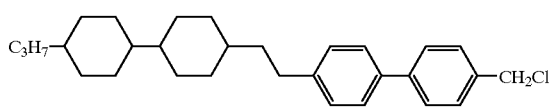 | (No. 158) | 4 wt % |
| 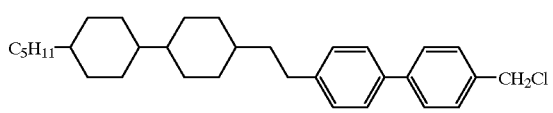 | (No. 159) | 3 wt % |
| 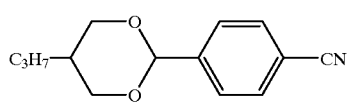 | | 10 wt % |
| 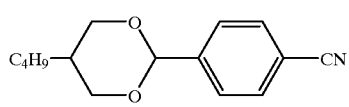 | | 10 wt % |
| 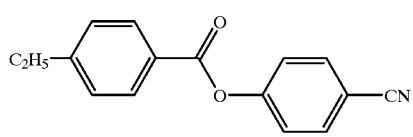 | | 10 wt % |
| 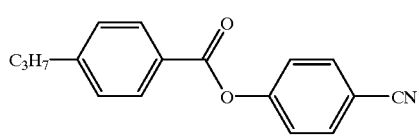 | | 6 wt % |
| 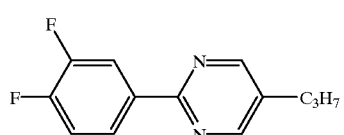 | | 6 wt % |

-continued
Composition example 6
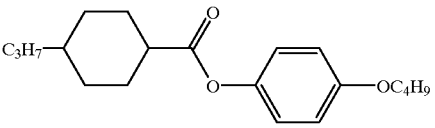 8 wt %
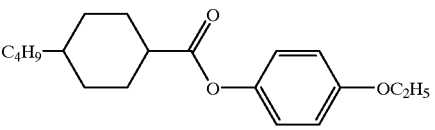 6 wt %
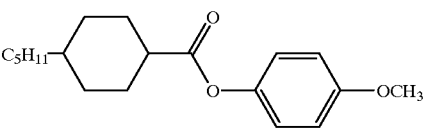 6 wt %
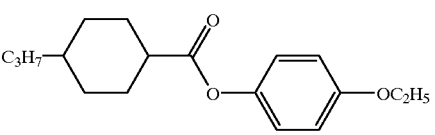 5 wt %
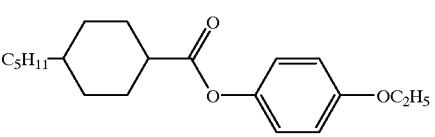 4 wt %
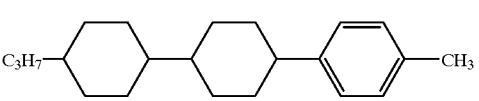 6 wt %
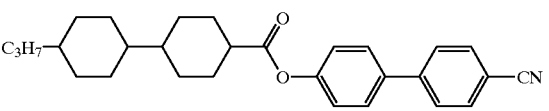 3 wt %
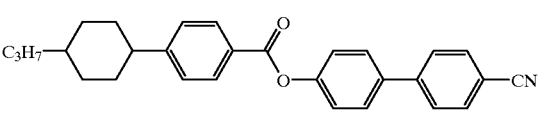 3 wt %
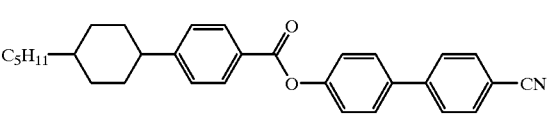 3 wt %
Composition example 7
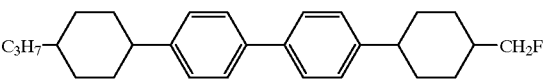 (No. 3)  5 wt %

| -continued | | |
|---|---|---|
| Composition example 7 | | |
| $C_4H_9$—⬡—⬢—⬢—⬡—$CH_2F$ | (No. 4) | 5 wt % |
| $C_3H_7$—⬡—⬢—⬢—⬡—$C_2H_4F$ | (No. 6) | 3 wt % |
| $C_3H_7$—⬡—⬢—⬢—⬡—$C_3H_6F$ | (No. 7) | 3 wt % |
| $C_2H_5$—⬡—⬢(F)—CN | | 15 wt % |
| $C_2H_5$—⬡—⬡—⬢(F)—CN | | 12 wt % |
| $C_3H_7$—⬡—⬡—⬢(F)—CN | | 12 wt % |
| $C_3H_7$—⬡—⬡—C(O)O—⬢—F | | 5 wt % |
| $C_5H_{11}$—⬡—⬡—C(O)O—⬢—F | | 4 wt % |
| $C_2H_5$—⬡—C(O)O—⬢—F | | 2 wt % |
| $C_3H_7$—⬡—C(O)O—⬢—F | | 2 wt % |
| $C_4H_9$—⬡—C(O)O—⬢—F | | 2 wt % |

| Composition example 7 | |
|---|---|
| 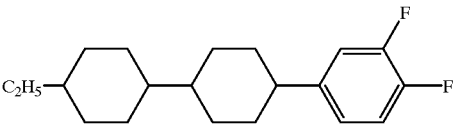 | 10 wt % |
| 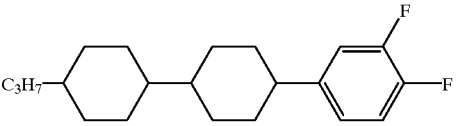 | 10 wt % |
| 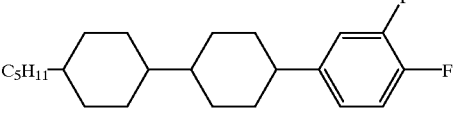 | 10 wt% |
| Composition example 8 | | |
|---|---|---|
| 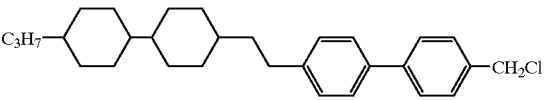 | (No. 120) | 3 wt % |
| 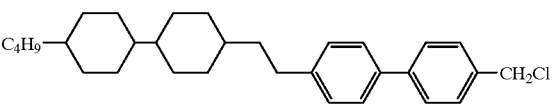 | (No. 121) | 5 wt % |
| 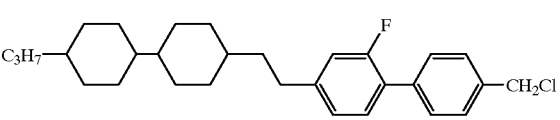 | (No. 142) | 6 wt % |
| 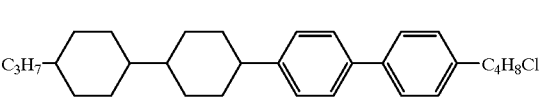 | (No. 72) | 6 wt % |
| 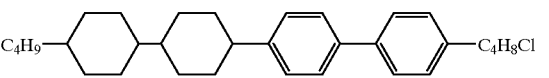 | (No. 75) | 6 wt % |
| 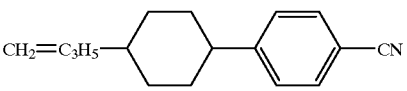 | | 12 wt % |
| 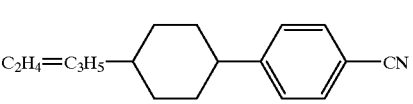 | | 10 wt % |

-continued
| Composition example 8 | |
|---|---|
| 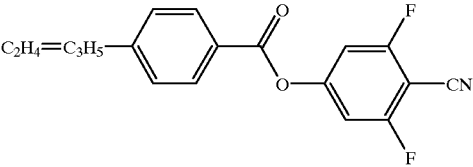 | 10 wt % |
| 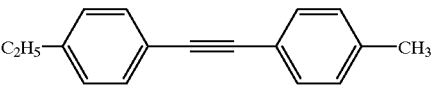 | 6 wt % |
| 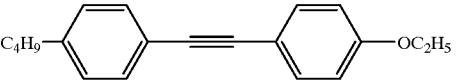 | 6 wt % |
| 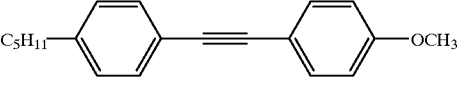 | 6 wt % |
| 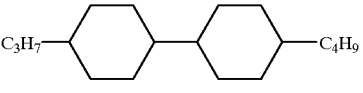 | 4 wt % |
| 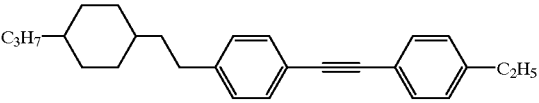 | 3 wt % |
| 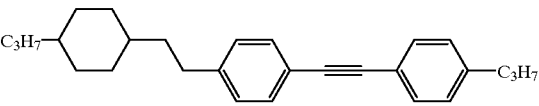 | 2 wt % |
| 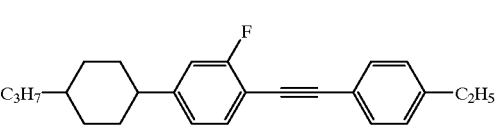 | 4 wt % |
| 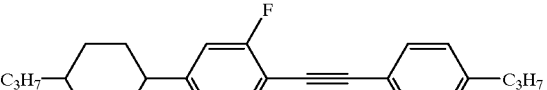 | 4 wt % |
| 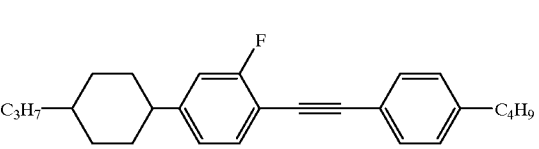 | 3 wt % |
| 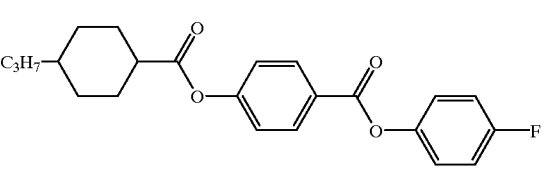 | 2 wt % |

| -continued | | |
|---|---|---|
| Composition example 8 | | |
| 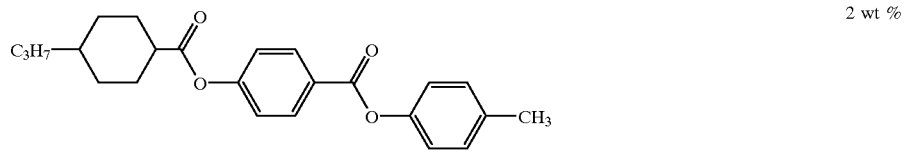 | | 2 wt % |
| Composition example 9 | | |
|---|---|---|
| 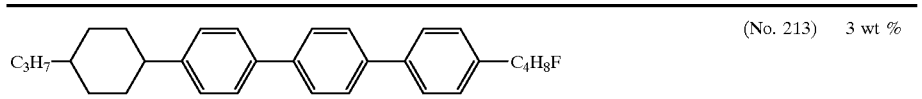 | (No. 213) | 3 wt % |
| 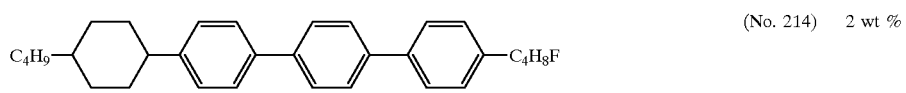 | (No. 214) | 2 wt % |
| 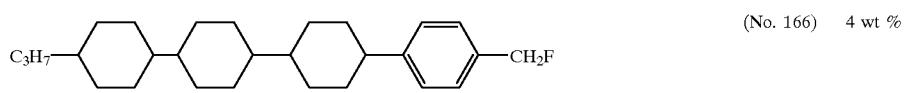 | (No. 166) | 4 wt % |
| 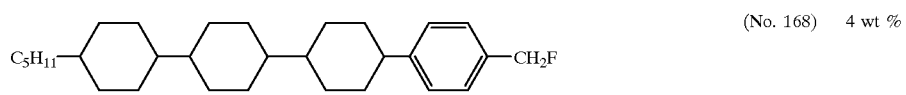 | (No. 168) | 4 wt % |
| 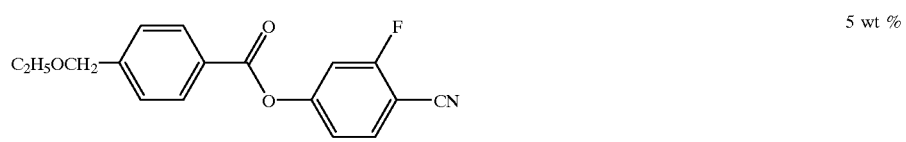 | | 5 wt % |
| 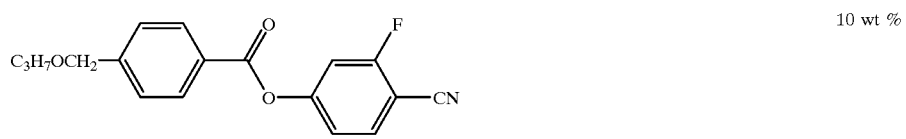 | | 10 wt % |
| 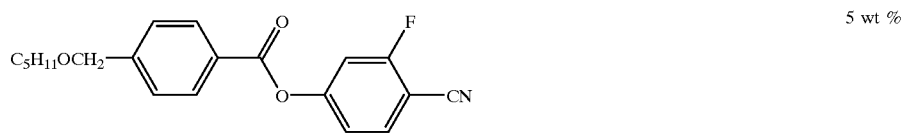 | | 5 wt % |
| 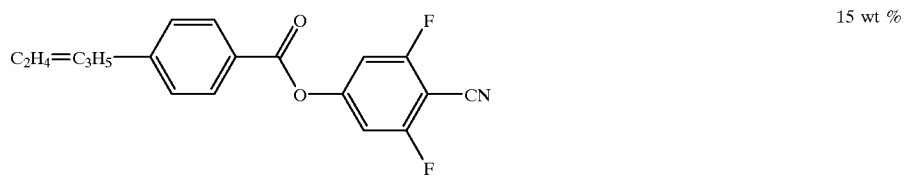 | | 15 wt % |
|  | | 8 wt % |

-continued

| Composition example 9 | |
|---|---|
| C₃H₇–[Cy]–[Cy]–C₄H₉ | 5 wt % |
| C₃H₇–[Cy]–[Cy]–C(=O)O–[Ph]–F | 5 wt % |
| C₅H₁₁–[Cy]–[Cy]–C(=O)O–[Ph]–F | 5 wt % |
| C₃H₇–[Cy]–[Ph]–C(=O)O–[Ph]–F | 6 wt % |
| C₃H₇–[Cy]–[Cy]–[Ph]–F | 2 wt % |
| C₃H₇–[Cy]–[Cy]–[Ph]–CH₃ | 6 wt % |
| C₃H₇–[Cy]–[Cy]–[Ph]–C₃H₇ | 4 wt % |
| C₃H₇–[Cy]–[Cy]–[Ph]–OCH₃ | 4 wt % |
| C₃H₇–[Cy]–CH₂CH₂–[Ph]–C≡C–[Ph]–C₂H₅ | 2 wt % |
| C₃H₇–[Cy]–CH₂CH₂–[Ph]–C≡C–[Ph]–C₃H₇ | 2 wt % |
| C₃H₇–[Cy]–[Ph(F)]–C≡C–[Ph]–C₂H₅ | 3 wt % |

| Composition example 10 | | |
|---|---|---|
| C₃H₇-⌬-⌬-⌬-⌬-C₄H₈F | (No. 174) | 5 wt % |
| C₄H₉-⌬-⌬-⌬-⌬-C₄H₈F | (NO. 176) | 5 wt % |
| C₃H₇-⌬-CH₂CH₂-⌬-⌬-⌬-CH₂F | (No. 89) | 5 wt % |
| C₃H₇-⌬-⌬-CN | | 18 wt % |
| C₃H₇-⌬-⌬(F)-CN | | 4 wt % |
| F-⌬-(pyrimidine)-C₅H₁₁ | | 10 wt % |
| C₃H₇-⌬-⌬-OC₂H₅ | | 4 wt % |
| C₂H₅-⌬-C≡C-⌬-CH₃ | | 4 wt % |
| C₃H₇-⌬-⌬-C₅H₁₁ | | 8 wt % |
| C₃H₇-⌬-⌬-C₄H₉ | | 6 wt % |
| C₃H₇-⌬-⌬-C(=O)OCH₃ | | 2 wt % |
| C₃H₇-⌬-⌬-⌬-CH₃ | | 10 wt % |
| C₃H₇-⌬-⌬-⌬-C₃H₇ | | 10 wt % |

-continued
| Composition example 10 | |
|---|---|
| 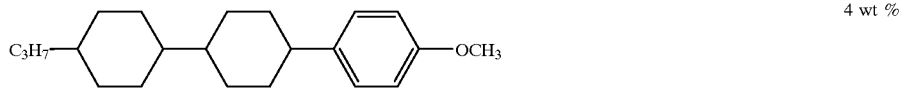 | 4 wt % |
| 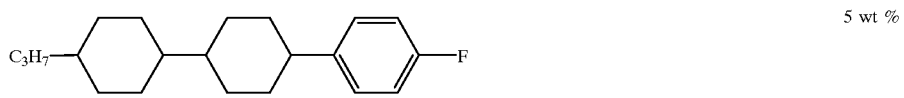 | 5 wt % |
| Composition example 11 | | |
|---|---|---|
| 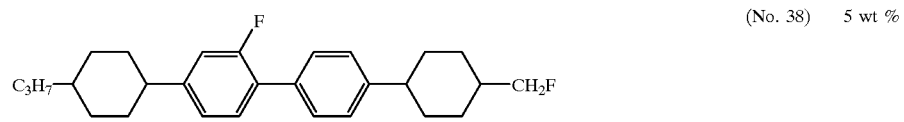 | (No. 38) | 5 wt % |
| 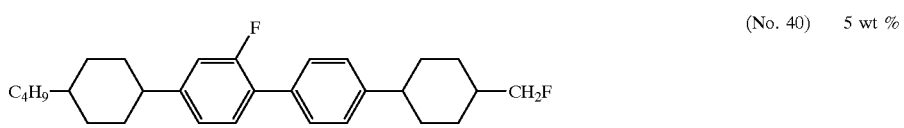 | (No. 40) | 5 wt % |
| 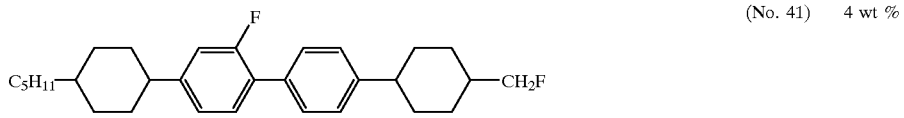 | (No. 41) | 4 wt % |
|  | | 10 wt % |
| 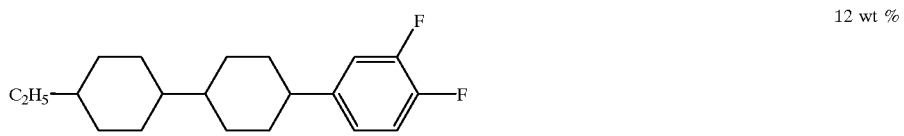 | | 12 wt % |
| 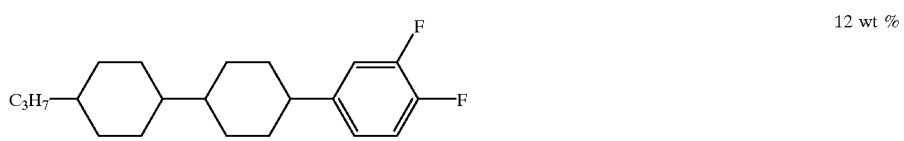 | | 12 wt % |
| 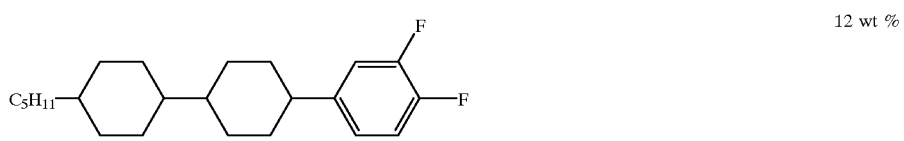 | | 12 wt % |
| 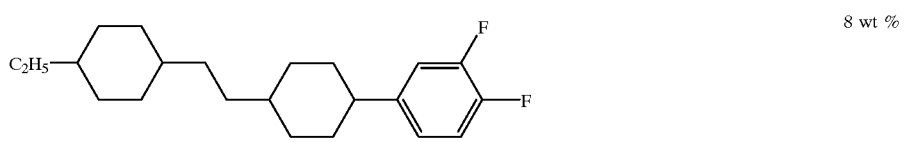 | | 8 wt % |

-continued

| Composition example 11 | |
|---|---|
| C₃H₇–[Cy]–CH₂CH₂–[Cy]–[Ph(3,4-F₂)] | 4 wt % |
| C₅H₁₁–[Cy]–CH₂CH₂–[Cy]–[Ph(3,4-F₂)] | 8 wt % |
| C₂H₅–[Cy]–[Ph]–[Ph(3,4-F₂)] | 5 wt % |
| C₃H₇–[Cy]–[Ph]–[Ph(3,4-F₂)] | 5 wt % |
| C₅H₁₁–[Cy]–[Ph]–[Ph(3,4-F₂)] | 10 wt % |

| Composition example 12 | | |
|---|---|---|
| C₃H₇–[Cy]–[Ph(2-F)]–[Ph]–[Cy]–CH₂F | (No. 38) | 6 wt % |
| C₄H₉–[Cy]–[Ph(2-F)]–[Ph]–[Cy]–CH₂F | (No. 40) | 6 wt % |
| C₅H₁₁–[Cy]–[Ph(2-F)]–[Ph]–[Cy]–CH₂F | (No. 41) | 6 wt % |
| C₇H₁₅–[Cy]–[Ph(3,4,5-F₃)] | | 6 wt % |

-continued
| Composition example 12 | |
|---|---|
| 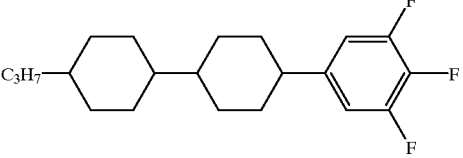 | 6 wt % |
| 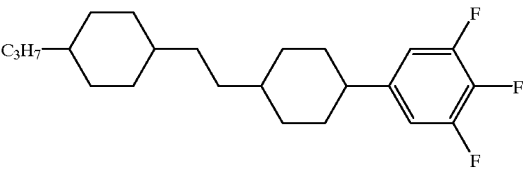 | 4 wt % |
| 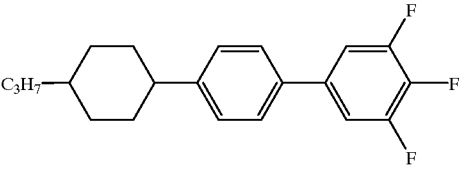 | 13 wt % |
| 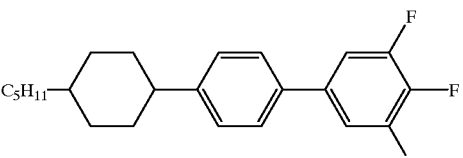 | 13 wt % |
| 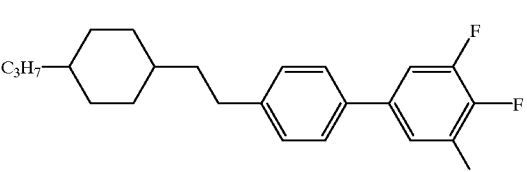 | 5 wt % |
| 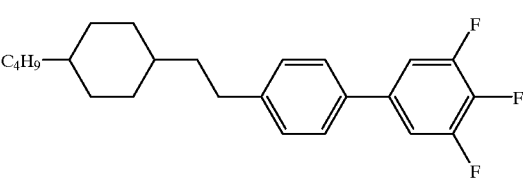 | 5 wt % |
| 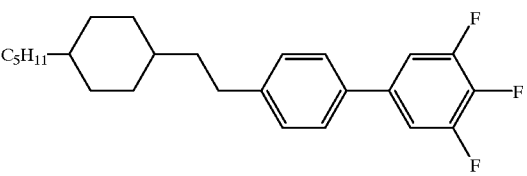 | 5 wt % |
| 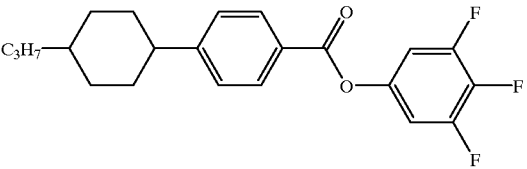 | 3 wt % |

| -continued | | |
|---|---|---|
| Composition example 12 | | |
| 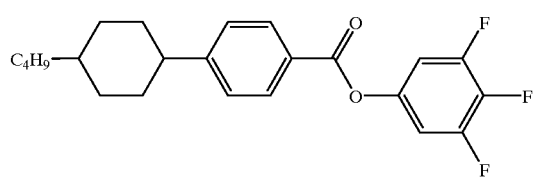 | | 3 wt % |
| 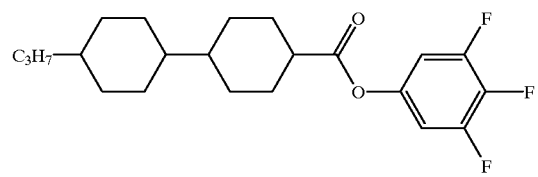 | | 13 wt % |
| 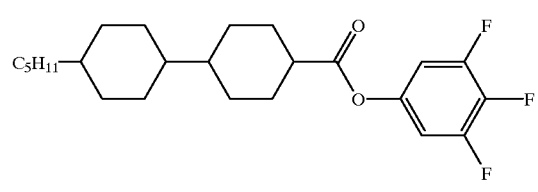 | | 6 wt % |
| Composition example 13 | | |
|---|---|---|
|  | (No. 1) | 5 wt % |
| 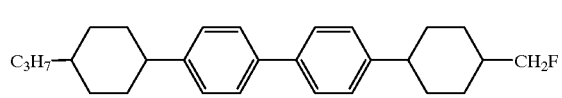 | (No. 3) | 4 wt % |
| 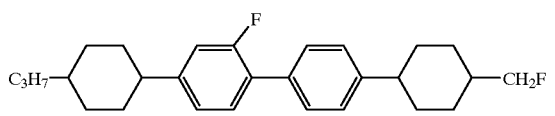 | (No. 38) | 5 wt % |
| 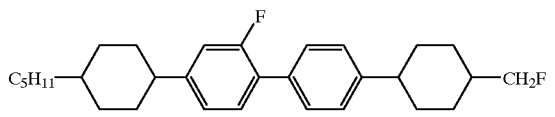 | (No. 41) | 5 wt % |
| 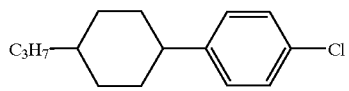 | | 7 wt % |
| 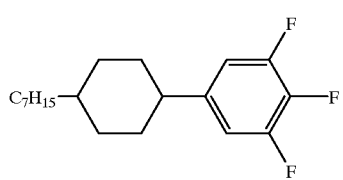 | | 8 wt % |

-continued
| Composition example 13 | |
|---|---|
| 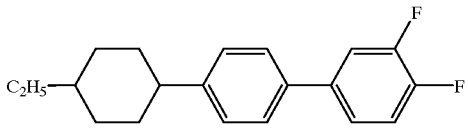 | 6 wt % |
| 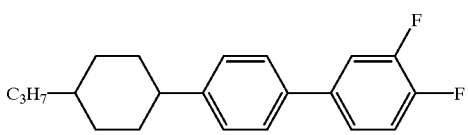 | 6 wt % |
| 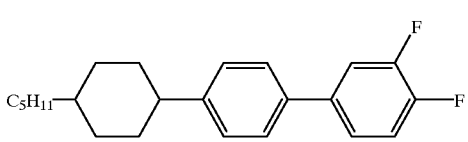 | 12 wt % |
| 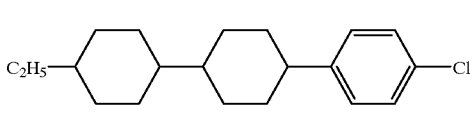 | 5 wt % |
| 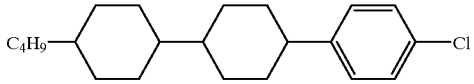 | 8 wt % |
| 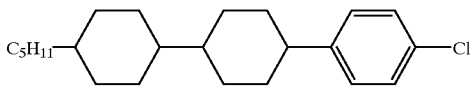 | 5 wt % |
| 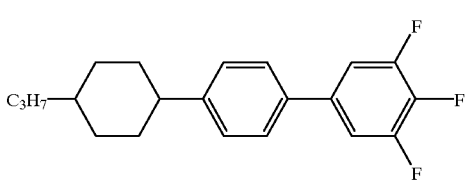 | 8 wt % |
| 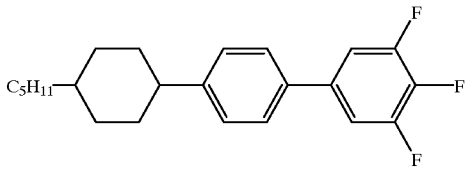 | 10 wt % |
| 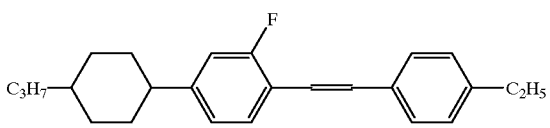 | 3 wt % |
| 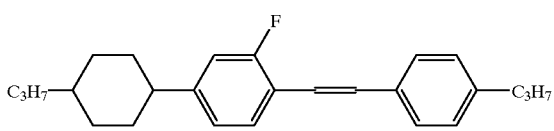 | 3 wt % |

| Composition example 14 | | |
|---|---|---|
| C₃H₇—[Cy]—CH₂CH₂—[Cy]—[Ph]—[Ph]—C₄H₈F | (No. 87) | 5 wt % |
| C₅H₁₁—[Cy]—CH₂CH₂—[Cy]—[Ph]—[Ph]—C₄H₈F | (No 88) | 4 wt % |
| C₃H₇—[Cy]—[Cy]—[Ph]—CH₂CH₂—[Ph]—CH₂F | (No. 93) | 5 wt % |
| C₅H₁₁—[Cy]—[Cy]—[Ph]—CH₂CH₂—[Ph]—CH₂F | (No. 94) | 4 wt % |
| C₃H₇—[Cy]—[Ph]—OC₂H₅ | | 3 wt % |
| C₃H₇—[Cy]—[Cy]—[Ph]—OCH₃ | | 2 wt % |
| C₂H₅—[Cy]—[Cy]—[Ph(3,4-F₂)] | | 10 wt % |
| C₃H₇—[Cy]—[Cy]—[Ph(3,4-F₂)] | | 10 wt % |
| C₅H₁₁—[Cy]—[Cy]—[Ph(3,4-F₂)] | | 10 wt % |
| C₂H₅—[Cy]—[Ph]—[Ph(3,4-F₂)] | | 5 wt % |
| C₃H₇—[Cy]—[Ph]—[Ph(3,4-F₂)] | | 5 wt % |

-continued
Composition example 14
| Structure | wt % |
|---|---|
| C₅H₁₁–Cy–Ph–Ph(3,4-diF) | 10 wt % |
| C₃H₇–Cy–Ph–Ph(3,4,5-triF) | 5 wt % |
| C₅H₁₁–Cy–Ph–Ph(3,4,5-triF) | 3 wt % |
| C₃H₇–Cy–Cy–CH₂CH₂–Ph(3,4,5-triF) | 8 wt % |
| C₅H₁₁–Cy–Cy–CH₂CH₂–Ph(3,4,5-triF) | 6 wt % |
| C₅H₁₁–Cy–CH₂CH₂–Cy–Ph(3,4,5-triF) | 3 wt % |
| C₅H₁₁–Cy–Cy–C(=O)O–Ph–Ph–F | 2 wt % |
Composition example 15
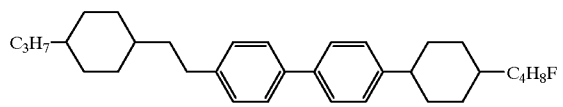 (NO. 20)    5 wt %

-continued
Composition example 15
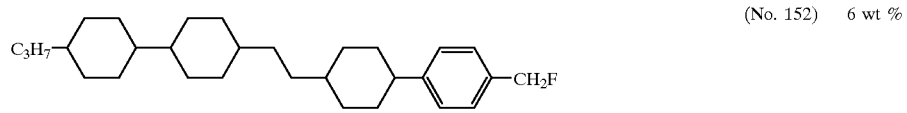 (No. 152) 6 wt %
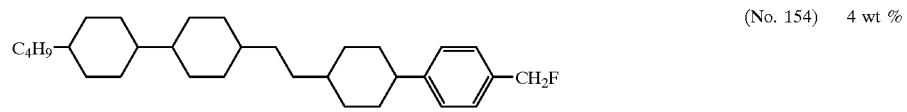 (No. 154) 4 wt %
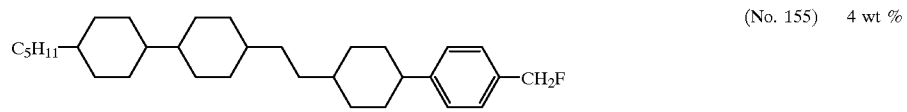 (No. 155) 4 wt %
 8 wt %
 6 wt %
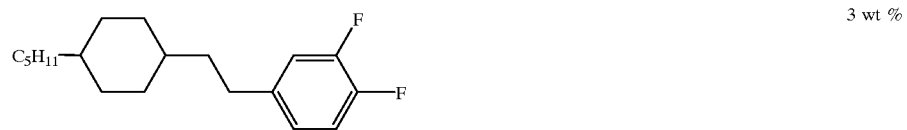 3 wt %
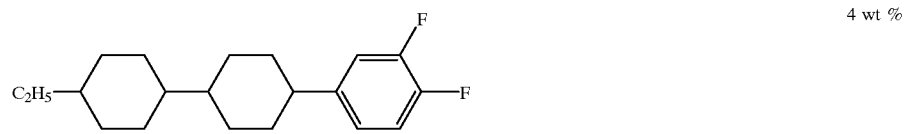 4 wt %
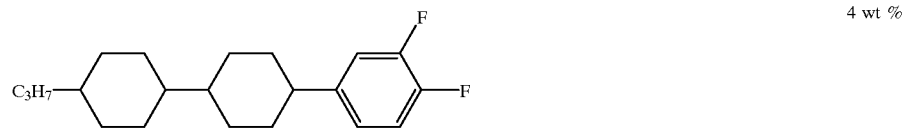 4 wt %
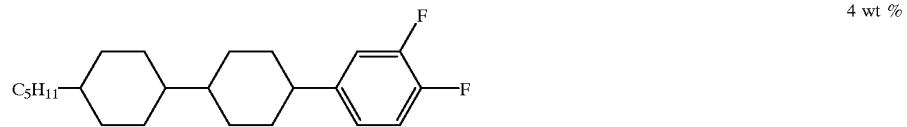 4 wt %
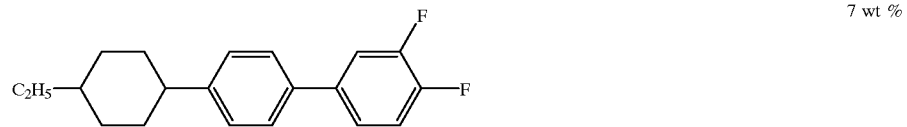 7 wt %

-continued
| Composition example 15 | |
|---|---|
| 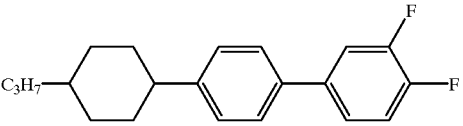 | 7 wt % |
| 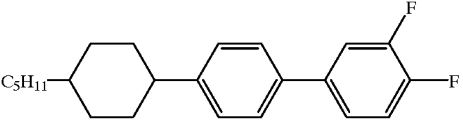 | 14 wt % |
| 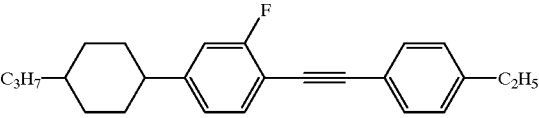 | 5 wt % |
| 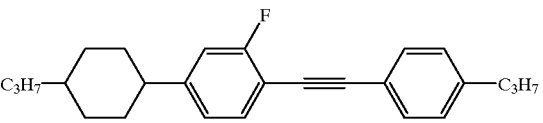 | 4 wt % |
| 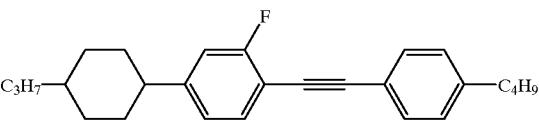 | 4 wt % |
| 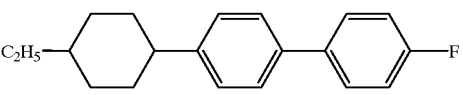 | 4 wt % |
| 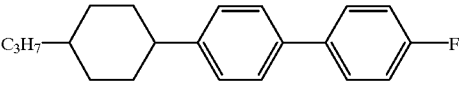 | 3 wt % |
| 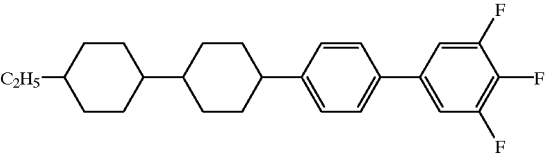 | 2 wt % |
| 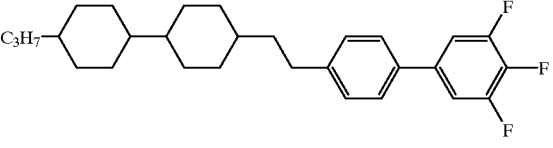 | 2 wt % |

| Composition example 16 | | |
|---|---|---|
| C4H9—⬡—⬢—⬢—⬡—C4H8F | (No. 1) | 3 wt % |
| C3H7—⬡—⬢—⬢—⬡—CH2F | (No. 3) | 4 wt % |
| C4H9—⬡—⬢—⬢—⬡—CH2F | (No. 4) | 4 wt % |
| C5H11—⬡—⬢—⬢—⬡—CH2F | (No. 5) | 2 wt % |
| C4H9—⬡—C(=O)O—⬢(3,4-F2) | | 10 wt % |
| C5H11—⬡—C(=O)O—⬢(3,4-F2) | | 10 wt % |
| C2H5—⬡—C(=O)O—⬢(3-F, 4-CN) | | 10 wt % |
| C3H7—⬡—C(=O)O—⬢(3-F, 4-CN) | | 10 wt % |
| C5H11—⬢—C(=O)O—⬢(3-F, 4-CN) | | 6 wt % |
| CH3OC3H6—⬡—⬢(3-F, 4-CN) | | 6 wt % |
| C3H7—⬡—⬡—C(=O)O—⬢(3,4-F2) | | 3 wt % |

Composition example 16

| Structure | Amount |
|---|---|
| C₅H₁₁–[Cy]–[Cy]–C(=O)O–[Ph(3-F,4-F)] | 3 wt % |
| C₂H₅–[Cy]–[Ph]–C(=O)O–[Ph(3-F,4-CN)] | 5 wt % |
| C₃H₇–[Cy]–[Ph]–C(=O)O–[Ph(3-F,4-CN)] | 5 wt % |
| C₅H₁₁–[Cy]–[Cy]–C(=O)O–[Ph(3-F,4-CN)] | 5 wt % |
| C₃H₇–[Cy]–[Ph]–C≡C–[Ph]–C₂H₅ | 6 wt % |
| CH₂=C₃H₅–[Cy]–[Cy]–C₃H₇ | 4 wt % |
| CH₂=CH–[Cy]–[Cy]–C₄H₉ | 4 wt % |

Composition example 17

| Structure | No. | Amount |
|---|---|---|
| C₃H₇–[Ph]–[Ph]–[Ph]–[Cy]–C₄H₉F | (No. 208) | 3 wt % |
| C₃H₇–[Cy]–[Cy]–[Cy]–[Ph]–C₄H₈F | (No. 167) | 3 wt % |
| C₃H₇–[Cy]–[Cy]–[Cy]–CH₂CH₂–[Ph]–CH₂F | (No. 182) | 8 wt % |

-continued

| Composition example 17 | | |
|---|---|---|
| C₄H₉–[Cy]–[Cy]–[Cy]–CH₂CH₂–[Ph]–CH₂F | (No. 185) | 8 wt % |
| C₅H₁₁–[Cy]–[Cy]–[Cy]–CH₂CH₂–[Ph]–CH₂F | (NO. 186) | 6 wt % |
| CH₂=CH–[Cy]–[Ph]–CN | | 10 wt % |
| C₂H₄=CH–[Cy]–[Ph]–CN | | 5 wt % |
| C₄H₉–[Ph]–[Ph]–C₂H₅ | | 3 wt % |
| C₃H₇–[Ph]–[Ph]–CN | | 5 wt % |
| C₅H₁₁–[Ph]–[Ph]–CN | | 5 wt % |
| C₃H₇–[Cy]–CH₂CH₂–[Ph]–OC₂H₅ | | 3 wt % |
| C₅H₁₁–[Cy]–CH₂CH₂–[Ph]–OC₃H₇ | | 6 wt % |
| C₃H₇–[Ph]–COO–[Ph]–CN | | 5 wt % |
| C₅H₁₁–[Cy]–COO–[Ph]–OCH₃ | | 6 wt % |
| C₅H₁₁–[Cy]–COO–[Ph]–OC₃H₇ | | 6 wt % |

-continued

| Composition example 17 | |
|---|---|
| C₅H₁₁—⌬—⌬—⌬—CN | 5 wt % |
| C₄H₉—⌬—[pyrimidine]—⌬—C₄H₉ | 2 wt % |
| C₄H₉—⌬—[pyrimidine]—⌬—C₅H₁₁ | 2 wt % |
| C₅H₁₁—[Cy]—⌬—CH₂CH₂—⌬—C₄H₉ | 3 wt % |
| C₅H₁₁—[Cy]—⌬—⌬—CH₂CH₂—⌬—C₃H₇ | 2 wt % |
| C₂H₄=CH—[Cy]—[Cy]—CH₂OCH₃ | 2 wt % |
| C₂H₄=C₃H₅—[Cy]—⌬—⌬—C₃H₇ | 2 wt % |

40

| Composition example 18 | | |
|---|---|---|
| C₃H₇—[Cy]—[Cy]—⌬(F)—⌬—C₄H₈F | (No. 99) | 4 wt % |
| C₄H₉—[Cy]—[Cy]—⌬(F)—⌬—C₄H₈F | (No. 100) | 4 wt % |
| C₃H₇—[Cy]—[Cy]—CH₂CH₂—⌬—⌬—CH₂F | (No. 109) | 3 wt % |

-continued

Composition example 18

| Structure | No. | wt% |
|---|---|---|
| C₄H₉-Cy-Cy-CH₂CH₂-Ph-Ph-CH₂F | (No. 112) | 4 wt % |
| C₃H₇-Ph-Ph-CN | | 11 wt % |
| C₄H₉-Ph-Ph-CN | | 5 wt % |
| C₂H₅-Ph-COO-Ph-CN | | 8 wt % |
| C₄H₉-Ph-COO-Ph-CN | | 12 wt % |
| C₅H₁₁-Ph-COO-Ph-CN | | 5 wt % |
| C₅H₁₁-Ph-COO-Ph(3-F)-CN | | 3 wt % |
| C₃H₇-Ph-COO-Ph(3-F)-CN | | 3 wt % |
| C₄H₉-Ph-COO-Ph(3-F)-CN | | 5 wt % |
| C₃H₇-Cy-COO-Ph-OC₂H₅ | | 5 wt % |
| C₄H₉-Cy-COO-Ph-OC₂H₅ | | 5 wt % |

| -continued |
|---|
| Composition example 18 |
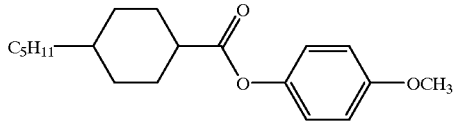 5 wt %
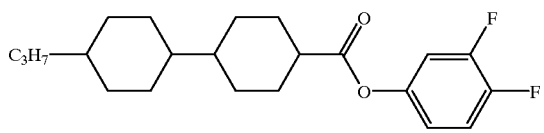 4 wt %
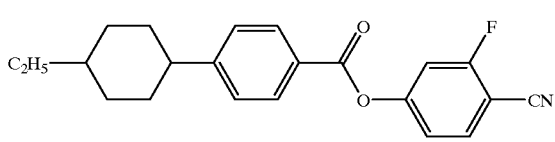 5 wt %
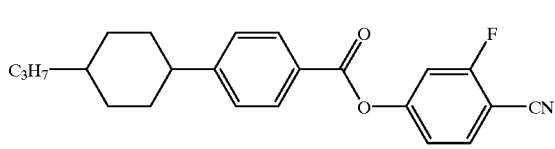 6 wt %
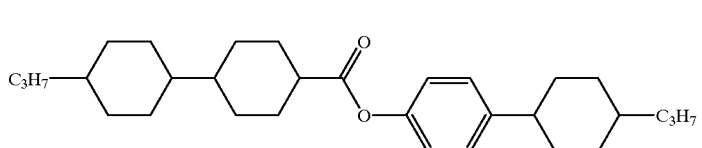 3 wt %
| Composition example 19 |
|---|
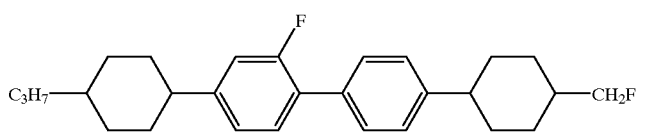 (No. 38) 5 wt %
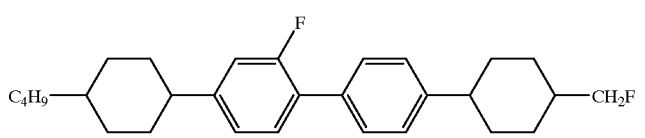 (No. 40) 5 wt %
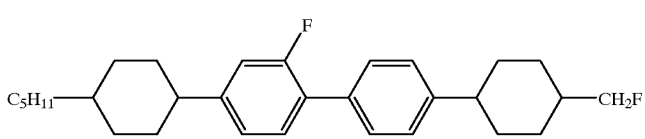 (No. 41) 5 wt %
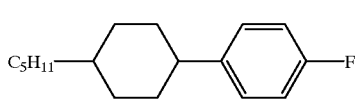 12 wt %

-continued

| Composition example 19 | |
|---|---|
| C₆H₁₃–[Cy]–[Ph]–F | 12 wt % |
| C₇H₁₅–[Cy]–[Ph]–F | 12 wt % |
| C₂H₅–[Cy]–[Cy]–[Ph]–OCF₃ | 6 wt % |
| C₃H₇–[Cy]–[Cy]–[Ph]–OCF₃ | 6 wt % |
| C₅H₁₁–[Cy]–[Cy]–[Ph]–OCF₃ | 6 wt % |
| C₃H₇–[Cy]–[Cy]–CH₂CH₂–[Ph]–OCF₃ | 5 wt % |
| C₅H₁₁–[Cy]–[Cy]–CH₂CH₂–[Ph]–OCF₃ | 6 wt % |
| C₃H₇–[Cy]–[Ph]–[Ph(3,4-F₂)] | 10 wt % |
| C₅H₁₁–[Cy]–[Ph]–[Ph(3,4-F₂)] | 10 wt % |

| Composition example 20 | | |
|---|---|---|
| C₃H₇–[Cy]–[Cy]–[Cy]–CH₂CH₂–[Ph]–C₂H₄F | (No. 183) | 4 wt % |

-continued
| Composition example 20 | | |
|---|---|---|
| 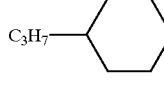 | (No. 184) | 4 wt % |
| 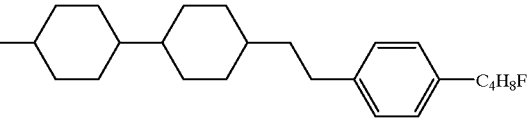 | (No. 124) | 4 wt % |
| 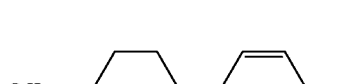 | | 8 wt % |
| 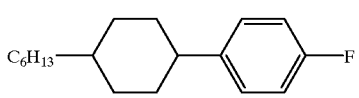 | | 7 wt % |
| 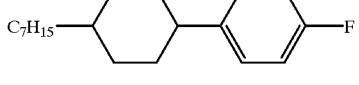 | | 8 wt % |
| 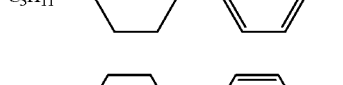 | | 3 wt % |
|  | | 3 wt % |
| 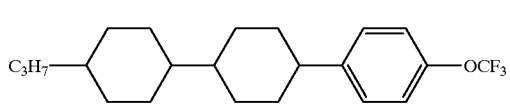 | | 3 wt % |
| 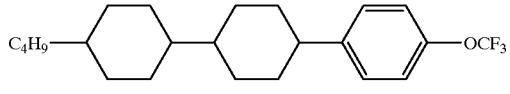 | | 3 wt % |
| 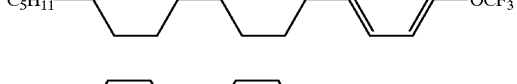 | | 3 wt % |
| 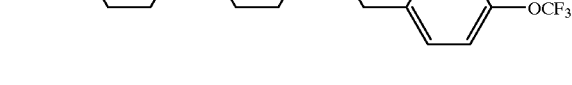 | | 3 wt % |
| 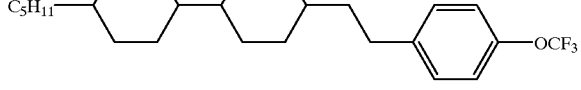 | | 2 wt % |

-continued
Composition example 20
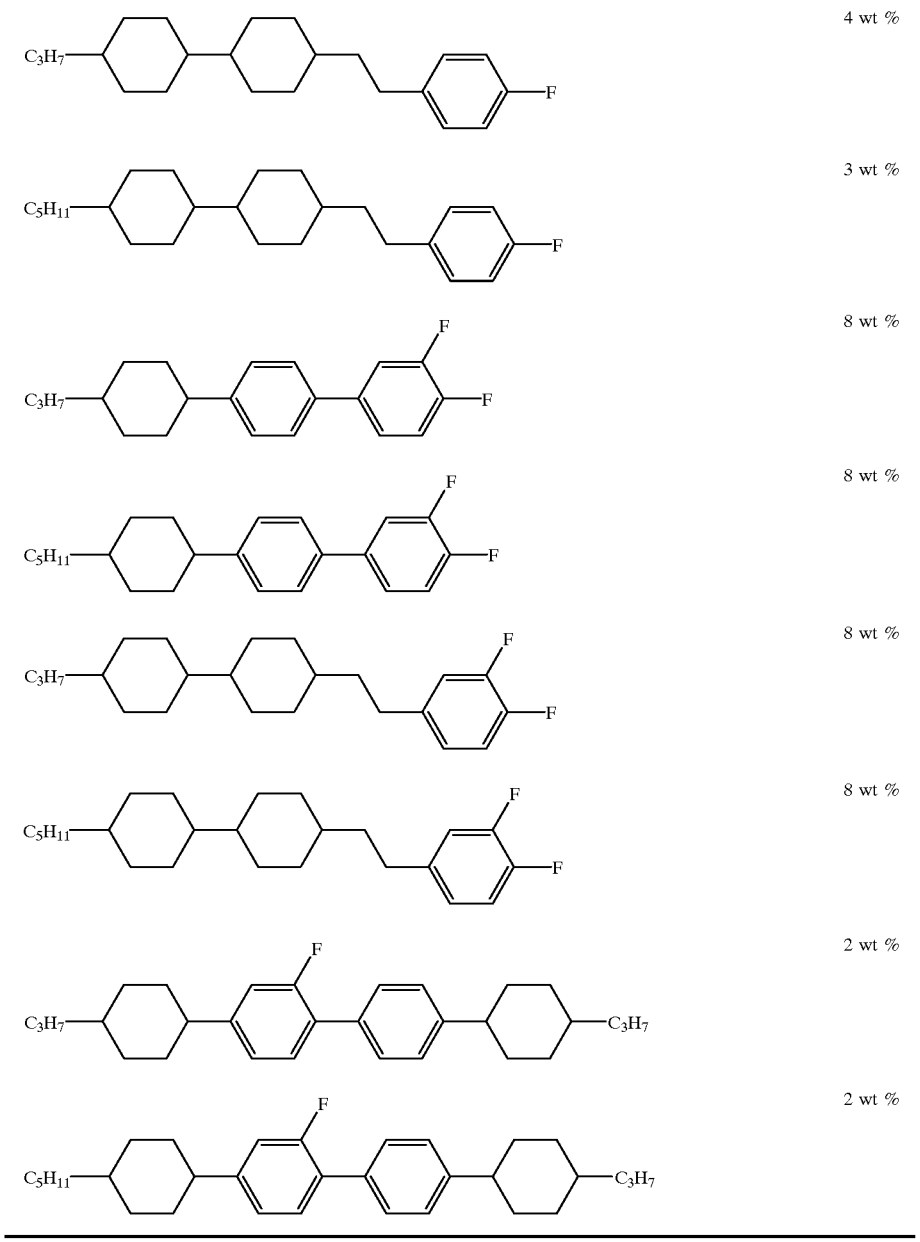
Composition example 21
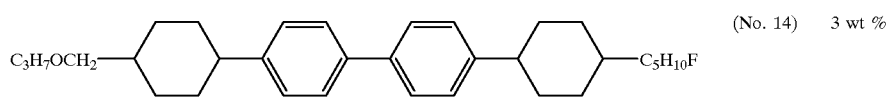
(No. 14)  3 wt %

-continued

Composition example 21

| Structure | No. | wt % |
|---|---|---|
| CH₂=CH–(Cy)–(Ph)–(Ph)–(Cy)–C₅H₁₀F | (No. 15) | 3 wt % |
| CH₂=C₃H₅–(Cy)–(Ph)–(Ph)–(Cy)–C₂H₄F | (No. 17) | 3 wt % |
| CH₂=CH–(Cy)–(Ph-F)–(Ph)–(Cy)–C₄H₈F | (No. 43) | 3 wt % |
| CH₂=CH–(Cy)–(Ph)–CN | | 10 wt % |
| C₂H₄=CH–(Cy)–(Ph)–CN | | 5 wt % |
| C₄H₉–(Ph)–(Ph)–C₂H₅ | | 3 wt % |
| C₃H₇–(Ph)–(Ph)–CN | | 5 wt % |
| C₅H₁₁–(Ph)–(Ph)–CN | | 5 wt % |
| C₃H₇–(Cy)–CH₂CH₂–(Ph)–OC₂H₅ | | 3 wt % |
| C₅H₁₁–(Cy)–CH₂CH₂–(Ph)–OC₃H₇ | | 6 wt % |
| C₃H₇–(Ph)–C(=O)O–(Ph)–CN | | 5 wt % |
| C₅H₁₁–(Cy)–C(=O)O–(Ph)–OCH₃ | | 6 wt % |

| Composition example 21 | |
|---|---|
| C₅H₁₁–⟨Cy⟩–C(O)O–⟨Ph⟩–OC₃H₇ | 6 wt % |
| C₅H₁₁–⟨Ph⟩–⟨Ph⟩–⟨Ph⟩–CN | 5 wt % |
| C₄H₉–⟨Ph⟩–⟨Pyrimidine⟩–⟨Ph⟩–C₄H₉ | 2 wt % |
| C₄H₉–⟨Ph⟩–⟨Pyrimidine⟩–⟨Ph⟩–C₅H₁₁ | 2 wt % |
| C₅H₁₁–⟨Cy⟩–⟨Ph⟩–CH₂CH₂–⟨Ph⟩–C₄H₉ | 3 wt % |
| C₅H₁₁–⟨Cy⟩–⟨Ph⟩–⟨Ph⟩–CH₂CH₂–⟨Ph⟩–C₃H₇ | 2 wt % |
| C₂H₄=CH–⟨Cy⟩–⟨Cy⟩–CH₂OCH₃ | 2 wt % |
| C₂H₄=C₃H₅–⟨Cy⟩–⟨Ph⟩–⟨Ph⟩–C₃H₇ | 2 wt % |

| Composition example 22 | | |
|---|---|---|
| C₃H₇–⟨Ph⟩–⟨Ph⟩–⟨Cy⟩–⟨Cy⟩–C₂H₄F | (No. 82) | 5 wt % |
| C₅H₁₁–⟨Cy⟩–⟨Cy⟩–⟨Cy⟩–⟨Cy⟩–C₅H₁₀F | (No. 34) | 4 wt % |

-continued
| Composition example 22 | | |
|---|---|---|
| 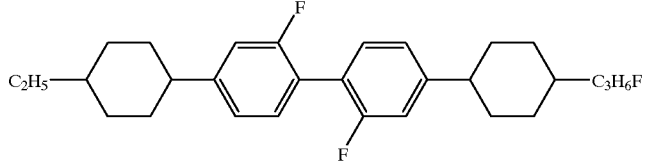 | (No. 62) | 5 wt % |
| 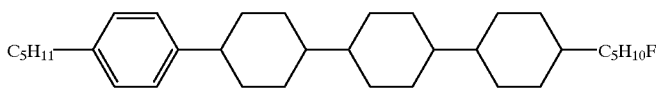 | (No. 205) | 4 wt % |
| 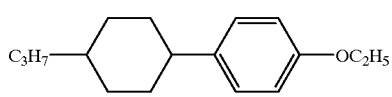 | | 3 wt % |
|  | | 2 wt % |
| 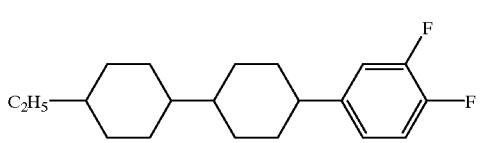 | | 10 wt % |
| 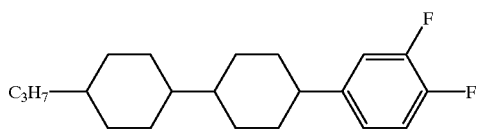 | | 10 wt % |
| 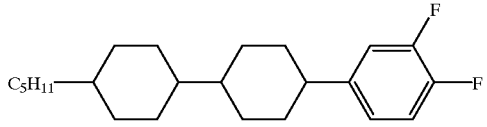 | | 10 wt % |
| 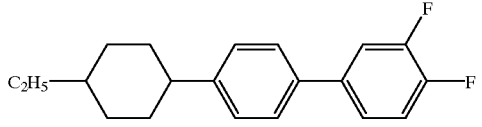 | | 5 wt % |
| 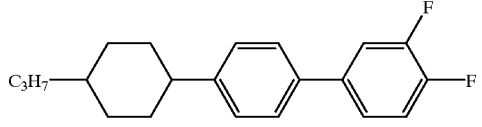 | | 5 wt % |
| 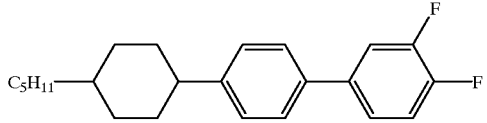 | | 10 wt % |

-continued

Composition example 22

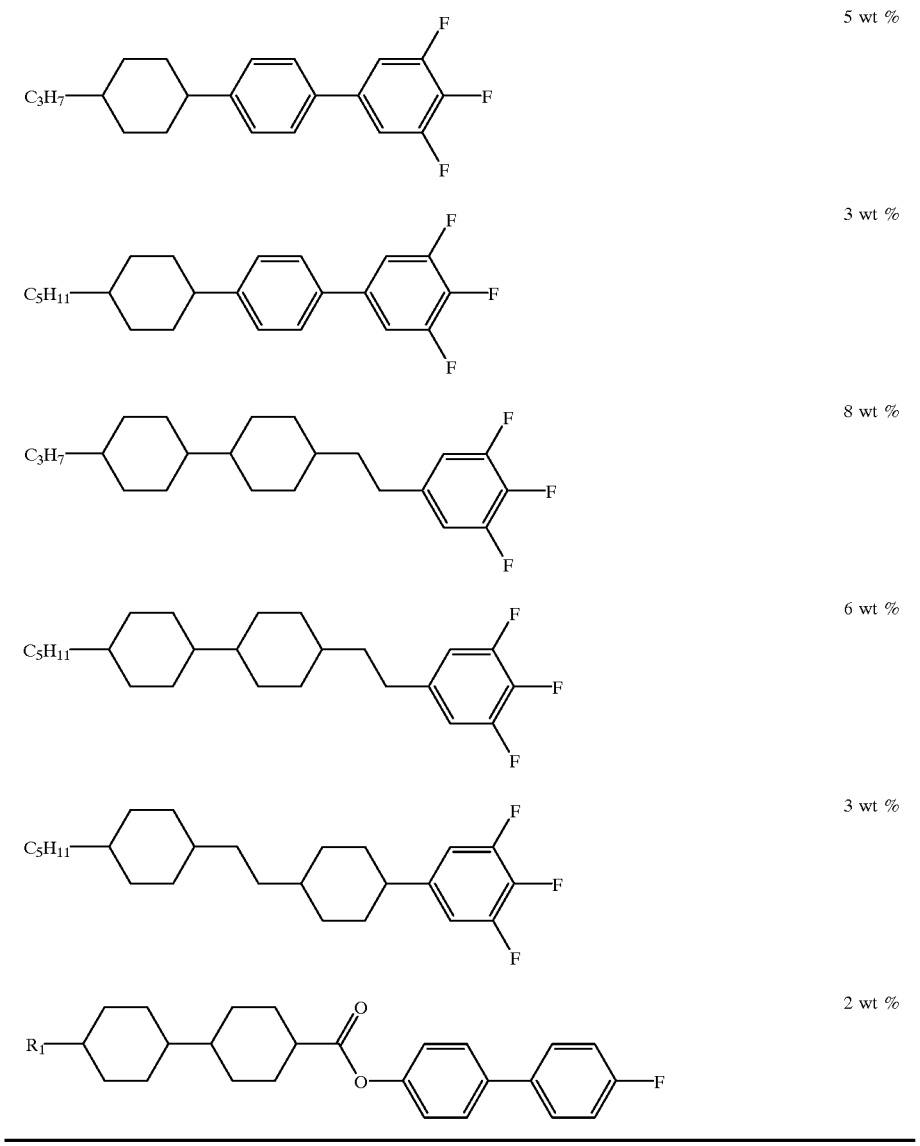

5 wt %

3 wt %

8 wt %

6 wt %

3 wt %

2 wt %

Examples of compositions are further shown in the followings, Table 1 shows compound symbols given as those in the columns "symbols", which are refered to their left columns, i.e. left end groups, bonding groups, ring structures, and right end groups.

TABLE 1

| | Symbols |
|---|---|
| 1) Left end groups | |
| $C_nH_{2n+1}-$ | n- |
| $C_nH_{2n+1}O-$ | nO- |
| $C_nH_{2n+1}OC_mH_{2m}-$ | nOm- |
| $CH_2=CH-$ | V- |
| $CH_2=CHC_nH_{2n}-$ | Vn- |
| $C_nH_{2n+1}CH=CHC_mH_{2m}-$ | nVm- |
| $C_nH_{2n+1}CH=CHC_mH_{2m}CH=CHC_kH_{2k}-$ | nVmVk- |

TABLE 1-continued

| | Symbols |
|---|---|
| 2) Ring Structure | |
| (phenyl) | B |
| (fluorophenyl) | B(F) |

TABLE 1-continued

| Structure | Symbols |
|---|---|
| (fluorobenzene, F at top) | B(2F) |
| (difluorobenzene, 2F's) | B(F,F) |
| (cyclohexane) | H |
| (pyridine/pyrazine N,N) | Py |
| (dioxane) | D |
| (cyclohexene) | Ch |

3) Bonding groups

| | |
|---|---|
| —C$_2$H$_4$— | 2 |
| —C$_4$H$_8$— | 4 |
| —COO— | E |
| —C≡C— | T |
| —CH=CH— | V |
| —CF$_2$O— | CF2O |
| —OCF$_2$— | OCF2 |

4) Right end groups

| | |
|---|---|
| —F | —F |
| —Cl | —CL |
| —CN | —C |
| —CF$_3$ | —CF$_3$ |
| —OCF$_3$ | —OCF$_3$ |
| —OCF$_2$H | —OCF2H |
| —C$_n$H$_{2n+1}$ | -n |
| —OC$_n$H$_{2n+1}$ | -On |
| —COOCH$_3$ | -EMe |
| —C$_n$H$_{2n}$CH=CH$_2$ | -nV |
| —C$_n$H$_{2m}$CH=CHC$_n$H$_{2n+1}$ | -mVn |
| —C$_m$H$_{2m}$CH=CHC$_n$H$_{2n}$F | -mVnF |
| —CH=CF$_2$ | -VFF |
| —C$_n$H$_{2n}$F | -nF |

Composition example 23

| | |
|---|---|
| 4-HBBH-4F | (No. 1) 5.0 wt % |
| 1V2-BEB(F,F)-C | 5.0 wt % |
| 3-HB-C | 25.0 wt % |
| 1-BTB-3 | 5.0 wt % |
| 2-BTB-1 | 10.0 wt % |
| 3-HH-4 | 11.0 wt % |
| 3-HHB-1 | 11.0 wt % |
| 3-HHB-3 | 5.0 wt % |
| 3-H2BTB-2 | 3.0 wt % |
| 3-H2BTB-3 | 4.0 wt % |
| 3-H2BTB-4 | 4.0 wt % |
| 3-HB(F)TB-2 | 6.0 wt % |
| 3-HB(F)TB-3 | 6.0 wt % |

Composition example 24

| | |
|---|---|
| 4-HBBH-4F | (No. 1) 5.0 wt % |
| V2-HB-C | 12.0 wt % |
| 1V2-HB-C | 12.0 wt % |
| 3-HB-C | 24.0 wt % |
| 3-HB(F)-C | 5.0 wt % |
| 2-BTB-1 | 2.0 wt % |
| 3-HH-4 | 8.0 wt % |
| 3-HH-VFF | 6.0 wt % |
| 2-HHB-C | 3.0 wt % |
| 3-HHB-C | 6.0 wt % |
| 3-HB(F)TB-2 | 8.0 wt % |
| 3-H2BTB-2 | 3.0 wt % |
| 3-H2BTB-3 | 3.0 wt % |
| 3-H2BTB-4 | 3.0 wt % |

Composition example 25

| | |
|---|---|
| 4-HBBH-4F | (No. 1) 3.0 wt % |
| 5-HBBH-1F | (No. 5) 3.0 wt % |
| 2O1-BEB(F)-C | 5.0 wt % |
| 3O1-BEB(F)-C | 15.0 wt % |
| 4O1-BEB(F)-C | 13.0 wt % |
| 5O1-BEB(F)-C | 13.0 wt % |
| 2-HHB(F)-C | 15.0 wt % |
| 3-HHB(F)-C | 15.0 wt % |
| 3-HB(F)TB-2 | 3.0 wt % |
| 3-HB(F)TB-3 | 2.0 wt % |
| 3-HB(F)TB-4 | 3.0 wt % |
| 3-HHB-1 | 8.0 wt % |
| 3-HHB-O1 | 2.0 wt % |

Composition example 26

| | |
|---|---|
| 3-HBBH-3F | (No. 7) 4.0 wt % |
| 4-HBBH-4F | (No. 1) 5.0 wt % |
| 5-PyB-F | 4.0 wt % |
| 3-PyB(F)-F | 4.0 wt % |
| 2-BB-C | 5.0 wt % |
| 4-BB-C | 4.0 wt % |
| 5-BB-C | 5.0 wt % |
| 2-PyB-2 | 2.0 wt % |
| 3-PyB-2 | 2.0 wt % |
| 4-PyB-2 | 2.0 wt % |
| 6-PyB-O5 | 3.0 wt % |
| 6-PyB-O6 | 3.0 wt % |
| 6-PyB-O7 | 3.0 wt % |
| 6-PyB-O8 | 3.0 wt % |
| 3-PyBB-F | 6.0 wt % |
| 4-PyBB-F | 6.0 wt % |
| 5-PyBB-F | 6.0 wt % |
| 3-HHB-1 | 6.0 wt % |
| 3-HHB-3 | 4.0 wt % |
| 2-H2BTB-2 | 4.0 wt % |

Composition example 26

| | |
|---|---|
| 2-H2BTB-3 | 4.0 wt % |
| 2-H2BTB-4 | 5.0 wt % |
| 3-H2BTB-3 | 5.0 wt % |
| 3-H2BTB-4 | 5.0 wt % |

Composition example 27

| | | |
|---|---|---|
| 3-HBBH-5F | (No. 10) | 3.0 wt % |
| 3-DB-C | | 10.0 wt % |
| 4-DB-C | | 10.0 wt % |
| 2-BEB-C | | 12.0 wt % |
| 3-BEB-C | | 4.0 wt % |
| 3-PyB(F)-F | | 6.0 wt % |
| 3-HEB-O4 | | 8.0 wt % |
| 4-HEB-O2 | | 6.0 wt % |
| 5-HEB-O1 | | 6.0 wt % |
| 3-HEB-O2 | | 5.0 wt % |
| 5-HEB-O2 | | 4.0 wt % |
| 5-HEB-5 | | 5.0 wt % |
| 4-HEB-5 | | 5.0 wt % |
| 1O-BEB-2 | | 4.0 wt % |
| 3-HHB-1 | | 3.0 wt % |
| 3-HHEBB-C | | 3.0 wt % |
| 3-HBEBB-C | | 3.0 wt % |
| 5-HBEBB-C | | 3.0 wt % |

Composition example 28

| | | |
|---|---|---|
| 3O1-HBBH-2F | (No. 14) | 4.0 wt % |
| 3-HB-C | | 18.0 wt % |
| 5-HB-C | | 3.0 wt % |
| 1O1-HB-C | | 10.0 wt % |
| 3-HB(F)-C | | 10.0 wt % |
| 2-PyB-2 | | 2.0 wt % |
| 3-PyB-2 | | 2.0 wt % |
| 4-PyB-2 | | 2.0 wt % |
| 1O1-HH-3 | | 7.0 wt % |
| 2-BTB-O1 | | 7.0 wt % |
| 3-HHB-1 | | 7.0 wt % |
| 3-HHB-F | | 4.0 wt % |
| 3-HHB-O1 | | 4.0 wt % |
| 3-HHB-3 | | 4.0 wt % |
| 3-H2BTB-2 | | 3.0 wt % |
| 3-H2BTB-3 | | 3.0 wt % |
| 2-PyBH-3 | | 4.0 wt % |
| 3-PyBH-3 | | 3.0 wt % |
| 3-PyBB-2 | | 3.0 wt % |

Composition example 29

| | | |
|---|---|---|
| 4-HBBH-4F | (No. 1) | 4.0 wt % |
| 3-HBB(2F)H-5F | (No. 46) | 3.0 wt % |
| 2O1-BEB(F)-C | | 5.0 wt % |
| 3O1-BEB(F)-C | | 12.0 wt % |
| 5O1-BEB(F)-C | | 4.0 wt % |
| 1V2-BEB(F,F)-C | | 10.0 wt % |
| 3-HH-EMe | | 10.0 wt % |
| 3-HB-O2 | | 18.0 wt % |
| 3-HHEB-F | | 3.0 wt % |
| 5-HHEB-F | | 3.0 wt % |
| 3-HBEB-F | | 4.0 wt % |
| 2O1-HBEB(F)-C | | 2.0 wt % |
| 3-HB(F)EB(F)-C | | 2.0 wt % |
| 3-HBEB(F,F)-C | | 2.0 wt % |

Composition example 29

| | |
|---|---|
| 3-HHB-F | 4.0 wt % |
| 3-HHB-O1 | 4.0 wt % |
| 3-HHB-3 | 6.0 wt % |
| 3-HEBEB-F | 2.0 wt % |
| 3-HEBEB-1 | 2.0 wt % |

Composition example 30

| | | |
|---|---|---|
| 3-HBB(2F)H-3F | (No. 45) | 3.0 wt % |
| 2O1-BEB(F)-C | | 5.0 wt % |
| 3O1-BEB(F)-C | | 12.0 wt % |
| 5O1-BEB(F)-C | | 4.0 wt % |
| 1V2-BEB(F,F)-C | | 16.0 wt % |
| 3-HB-O2 | | 10.0 wt % |
| 3-HH-4 | | 3.0 wt % |
| 3-HHB-F | | 3.0 wt % |
| 3-HHB-1 | | 8.0 wt % |
| 3-HHB-O1 | | 4.0 wt % |
| 3-HBEB-F | | 4.0 wt % |
| 3-HHEB-F | | 7.0 wt % |
| 5-HHEB-F | | 7.0 wt % |
| 3-H2BTB-2 | | 4.0 wt % |
| 3-H2BTB-3 | | 4.0 wt % |
| 3-H2BTB-4 | | 4.0 wt % |
| 3-HB(F)TB-2 | | 2.0 wt % |

Composition example 31

| | | |
|---|---|---|
| 3-HBBH-5F | (No. 10) | 3.0 wt % |
| 3-HBBH-3F | (No. 7) | 3.0 wt % |
| 2-BEB-C | | 12.0 wt % |
| 3-BEB-C | | 4.0 wt % |
| 4-BEB-C | | 6.0 wt % |
| 3-HB-C | | 28.0 wt % |
| 3-HEB-O4 | | 12.0 wt % |
| 4-HEB-O2 | | 8.0 wt % |
| 5-HEB-O1 | | 8.0 wt % |
| 3-HEB-O2 | | 6.0 wt % |
| 5-HEB-O2 | | 5.0 wt % |
| 3-HHB-1 | | 3.0 wt % |
| 3-HHB-O1 | | 2.0 wt % |

Composition example 32

| | | |
|---|---|---|
| 4-HBBH-4F | (No. 1) | 4.0 wt % |
| 3-HBBH-3F | (No. 7) | 4.0 wt % |
| 2-BEB-C | | 10.0 wt % |
| 5-BB-C | | 12.0 wt % |
| 7-BB-C | | 7.0 wt % |
| 1-BTB-3 | | 7.0 wt % |
| 2-BTB-1 | | 10.0 wt % |
| 1O-BEB-2 | | 10.0 wt % |
| 1O-BEB-5 | | 12.0 wt % |
| 2-HHB-1 | | 4.0 wt % |
| 3-HHB-F | | 4.0 wt % |
| 3-HHB-1 | | 7.0 wt % |
| 3-HHB-O1 | | 4.0 wt % |
| 3-HHB-3 | | 5.0 wt % |

Composition example 33

| | | |
|---|---|---|
| 4-HBBH-4F | (No. 1) | 5.0 wt % |
| 2-HHB(F)-F | | 15.0 wt % |
| 3-HHB(F)-F | | 15.0 wt % |
| 5-HHB(F)-F | | 15.0 wt % |
| 2-H2HB(F)-F | | 10.0 wt % |
| 3-H2HB(F)-F | | 5.0 wt % |
| 5-H2HB(F)-F | | 10.0 wt % |
| 2-HBB(F)-F | | 6.0 wt % |
| 3-HBB(F)-F | | 6.0 wt % |
| 5-HBB(F)-F | | 13.0 wt % |

Composition example 34

| | | |
|---|---|---|
| 4-HBBH-4F | (No. 1) | 5.0 wt % |
| 3-HBB(2F)H-3F | (No. 45) | 3.0 wt % |
| 7-HB(F)-F | | 5.0 wt % |
| 5-H2B(F)-F | | 5.0 wt % |
| 3-HH-4 | | 5.0 wt % |
| 3-HB-O2 | | 10.0 wt % |
| 2-HHB(F)-F | | 10.0 wt % |
| 3-HHB(F)-F | | 10.0 wt % |
| 5-HHB(F)-F | | 10.0 wt % |
| 3-H2HB(F)-F | | 5.0 wt % |
| 2-HBB(F)-F | | 3.0 wt % |
| 3-HBB(F)-F | | 3.0 wt % |
| 5-HBB(F)-F | | 6.0 wt % |
| 2-H2BB(F)-F | | 5.0 wt % |
| 3-H2BB(F)-F | | 6.0 wt % |
| 3-HHB-1 | | 4.0 wt % |
| 3-HHB-O1 | | 3.0 wt % |
| 3-HHB-3 | | 2.0 wt % |

Composition example 35

| | | |
|---|---|---|
| 5-HBBH-1F | (No. 5) | 3.0 wt % |
| 3-HBBH-5F | (No. 10) | 3.0 wt % |
| 7-HB(F,F)-F | | 3.0 wt % |
| 3-HB-O2 | | 7.0 wt % |
| 2-HHB(F)-F | | 8.0 wt % |
| 3-HHB(F)-F | | 8.0 wt % |
| 5-HHB(F)-F | | 8.0 wt % |
| 2-HBB(F)-F | | 9.0 wt % |
| 3-HBB(F)-F | | 9.0 wt % |
| 5-HBB(F)-F | | 16.0 wt % |
| 2-HBB-F | | 4.0 wt % |
| 3-HBB-F | | 4.0 wt % |
| 5-HBB-F | | 3.0 wt % |
| 3-HBB(F,F)-F | | 5.0 wt % |
| 5-HBB(F,F)-F | | 10.0 wt % |

Composition example 36

| | | |
|---|---|---|
| 3-HBB(2F)H-3F | (No. 45) | 3.0 wt % |
| 3-HBB(2F)H-5F | (No. 46) | 3.0 wt % |
| 7-HB(F,F)-F | | 4.0 wt % |
| 3-H2HB(F,F)-F | | 12.0 wt % |
| 4-H2HB(F,F)-F | | 10.0 wt % |
| 5-H2HB(F,F)-F | | 10.0 wt % |
| 3-HHB(F,F)-F | | 10.0 wt % |
| 4-HHB(F,F)-F | | 5.0 wt % |
| 3-HH2B(F,F)-F | | 12.0 wt % |
| 5-HH2B(F,F)-F | | 7.0 wt % |
| 3-HBB(F,F)-F | | 12.0 wt % |
| 5-HBB(F,F)-F | | 12.0 wt % |

Composition example 37

| | | |
|---|---|---|
| 3-HBBH-3F | (No. 7) | 4.0 wt % |
| 3-HB-CL | | 10.0 wt % |
| 5-HB-CL | | 4.0 wt % |
| 7-HB-CL | | 4.0 wt % |
| 1O1-HH-5 | | 5.0 wt % |
| 2-HBB(F)-F | | 8.0 wt % |
| 3-HBB(F)-F | | 8.0 wt % |
| 5-HBB(F)-F | | 14.0 wt % |
| 4-HHB-CL | | 8.0 wt % |
| 5-HHB-CL | | 8.0 wt % |
| 3-H2HB(F)-CL | | 4.0 wt % |
| 3-HBB(F,F)-F | | 10.0 wt % |
| 5-H2BB(F,F)-F | | 9.0 wt % |
| 3-HB(F)VB-2 | | 2.0 wt % |
| 3-HB(F)VB-3 | | 2.0 wt % |

Composition example 38

| | | |
|---|---|---|
| 4-HBBH-4F | (No. 1) | 2.0 wt % |
| 3O1-HBBH-2F | (No. 14) | 4.0 wt % |
| 3-HHB(F,F)-F | | 9.0 wt % |
| 3-H2HB(F,F)-F | | 8.0 wt % |
| 4-H2HB(F,F)-F | | 8.0 wt % |
| 5-H2HB(F,F)-F | | 8.0 wt % |
| 3-HBB(F,F)-F | | 21.0 wt % |
| 5-HBB(F,F)-F | | 20.0 wt % |
| 3-H2BB(F,F)-F | | 10.0 wt % |
| 5-HHBB(F,F)-F | | 2.0 wt % |
| 3-HH2BB(F,F)-F | | 2.0. wt % |
| 5-HHEBB-F | | 2.0 wt % |
| 1O1-HBBH-4 | | 2.0 wt % |
| 1O1-HBBH-5 | | 2.0 wt % |

Composition example 39

| | | |
|---|---|---|
| 4-HBBH-4F | (No. 1) | 2.0 wt % |
| 3-HBB(2F)H-5F | (No. 46) | 2.0 wt % |
| 5-HB-F | | 12.0 wt % |
| 6-HB-F | | 9.0 wt % |
| 7-HB-F | | 7.0 wt % |
| 2-HHB-OCF3 | | 7.0 wt % |
| 3-HHB-OCF3 | | 9.0 wt % |
| 4-HHB-OCF3 | | 7.0 wt % |
| 5-HHB-OCF3 | | 5.0 wt % |
| 3-HH2B-OCF3 | | 4.0 wt % |
| 5-HH2B-OCF3 | | 4.0 wt % |
| 3-HHB(F,F)-OCF3 | | 5.0 wt % |
| 3-HBB(F)-F | | 10.0 wt % |
| 5-HBB(F)-F | | 10.0 wt % |
| 3-HH2B(F)-F | | 3.0 wt % |
| 3-HB(F)BH-3 | | 2.0 wt % |
| 5-HBBH-3 | | 2.0 wt % |

| Composition example 40 | | |
|---|---|---|
| 4-HBBH-4F | (No. 1) | 3.0 wt % |
| 3-HBB(2F)H-3F | (No. 45) | 4.0 wt % |
| 5-H4HB(F,F)-F | | 7.0 wt % |
| 5-H4HB-OCF3 | | 8.0 wt % |
| 3-H4HB(F,F)-CF3 | | 8.0 wt % |
| 5-H4HB(F,F)-CF3 | | 10.0 wt % |
| 3-HB-CL | | 6.0 wt % |
| 5-HB-CL | | 4.0 wt % |
| 2-H2BB(F)-F | | 5.0 wt % |
| 3-H2BB(F)-F | | 10.0 wt % |
| 5-HVHB(F,F)-F | | 5.0 wt % |
| 3-HHB-OCF3 | | 5.0 wt % |
| 3-H2HB-OCF3 | | 5.0 wt % |
| V-HHB(F)-F | | 5.0 wt % |
| 3-HChB(F)-F | | 5.0 wt % |
| 5-HHEB-OCF3 | | 2.0 wt % |
| 3-HBEB(F,F)-F | | 5.0 wt % |
| 5-HH-V2F | | 3.0 wt % |

| Composition example 41 | | |
|---|---|---|
| 4-HBBH-4F | (No. 1) | 5.0 wt % |
| 2-HHB(F)-F | | 2.0 wt % |
| 3-HHB(F)-F | | 2.0 wt % |
| 5-HHB(F)-F | | 2.0 wt % |
| 2-HBB(F)-F | | 6.0 wt % |
| 3-HBB(F)-F | | 6.0 wt % |
| 5-HBB(F)-F | | 10.0 wt % |
| 2-H2BB(F)-F | | 9.0 wt % |
| 3-H2BB(F)-F | | 9.0 wt % |
| 3-HBB(F,F)-F | | 25.0 wt % |
| 5-HBB(F,F)-F | | 19.0 wt % |
| 1O1-HBBH-4 | | 3.0 wt % |
| 1O1-HBBH-5 | | 2.0 wt % |

BEST MODE FOR CARRYING OUT THE INVENTION

Figure 1:
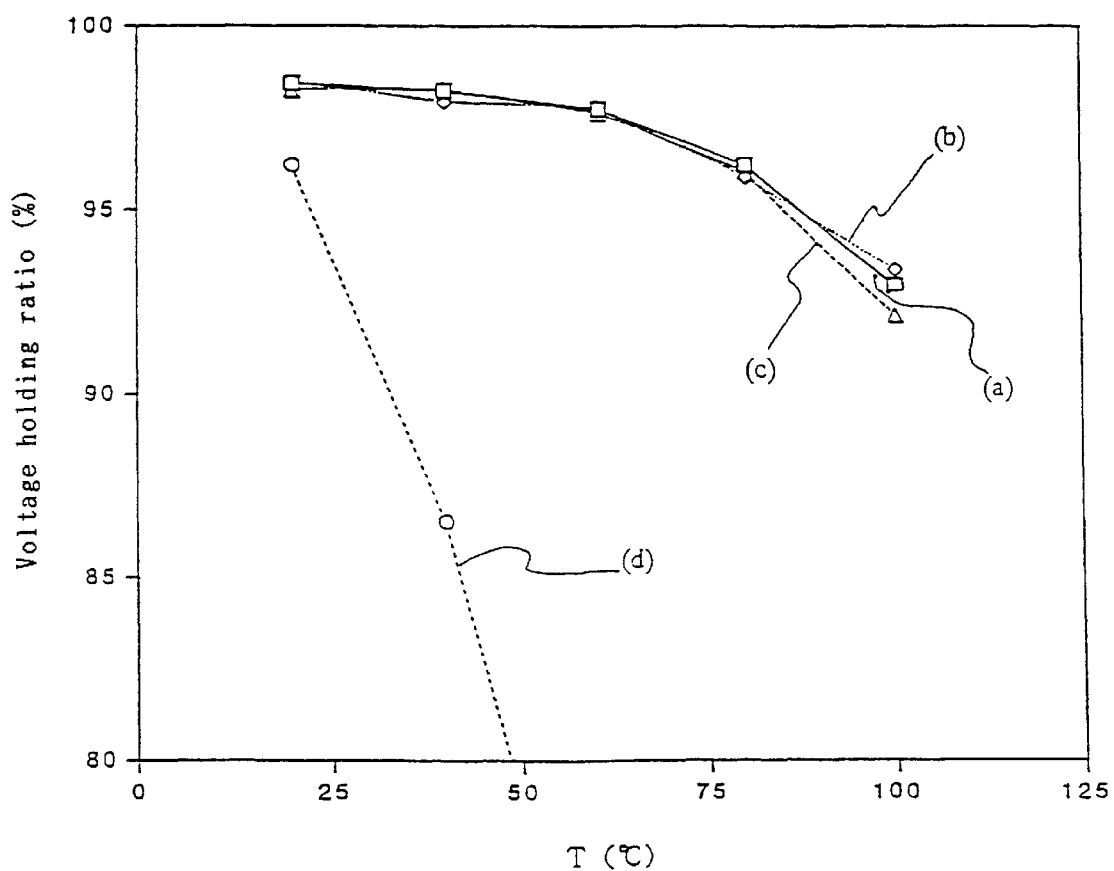
FIG. 1 shows a graph illustrating the effect of liquid crystal composition examples of the present invention in relation to a voltage holding ratio (%) and T (° C.). (a) shows a mother liquid crystal composition, (b) shows an example of a liquid crystal composition of the present invention, (c) shows a comparative example of a liquid crystal composition and (d) shows another comparative example of a liquid crystal composition.

The following examples illustrate the present invention more specifically. In each example, C shows a crystal, SA shows a smectic A phase, SB shows a smectic B phase, Sx shows a smectic phase in which the phase structure is not analyzed, N shows a nematic phase and I shows an isotropic phase, and the unit of phase transition temperature is 20 C.

EXAMPLE 1

Preparation of 4-(trans-4-(4-fluorobutyl)cyclohexyl)-4'-(trans-4-butylcyclohexyl)biphenyl (in general formula (1), wherein R is $C_4H_9$, m is 4, X is F, both $A_1$ and $A_4$ are trans-1,4-cyclohexylene groups, both $A_2$ and $A_3$ are 1,4-phenylene groups, all of $Z_1$, $Z_2$, and $Z_3$ are covalent bonds) (Compound No. 1)

4-(Trans-4-(4-Hydroxybutyl)cyclohexyl)-4'-(trans-4-butylcyclohexyl)biphenyl 6.3 g (0.014 mol) and dichloromethane 50 ml were mixed. To the mixture, a solution of DAST 3.4 g (0.021 mol) in dichloromethane 7 ml were added dropwise to maintain the temperature at −50° C., and the mixture was stirred for 30 minutes at the same temperature. Then, the temperature was increased slowly and the mixture was stirred for 6 hours at room temperature.

The reaction mixture was poured into ice water 100 ml and extracted with dichloromethane 100 ml. The obtained organic phase was washed with water three times and dried over anhydrous magnesium sulfate. The solvent was distilled out under reduced pressure, the residue was chromatographed over silica gel (elute: toluene/heptane) to obtain 5.0 g of crude 4-(trans-4-(4-fluorobutyl)cyclohexyl)- 4'-(trans-4-butylcyclohexyl)biphenyl. The resulting compound was recrystallized from ethyl acetate, and 20 g of the title compound (yield: 42.9%) was obtained.

C 64 Sx 235 N 298 I

Moreover, the structure was supported by each spectrum data.

Mass spectrometric analysis: 448 ($M^+$)

$^1$H-NMR ($CDCl_3$, TMS internal standard)

δ (ppm)

0.81–2.61 (m, 35H)

4.45 (dt, 2H)

7.37 (dd, 8H)

The following compounds are prepared according to the above method of Example 1 (No.2–No.34).

No.

2 4-(trans-4-fluoromethylcyclohexyl)-4'-(trans-4-ethylcyclohexyl)biphenyl 3 4-(trans-4-fluoromethylcyclohexyl)-4'-(trans-4-propylcyclohexyl)biphenyl 4 4-(trans-4-fluoromethylcyclohexyl)-4'-(trans-4-butylcyclohexyl)biphenyl 5 4-(trans-4-fluoromethylcyclohexyl)-4'-(trans-4-pentylcyclohexyl)biphenyl C-Sx 103

N-I 292

6 4-(trans-4-(2-fluoroethyl)cyclohexyl)-4'-(trans-4-propylcyclohexyl)biphenyl 7 4-(trans-4-(3-fluoropropyl)cyclohexyl)-4'-(trans-4-propylcyclohexyl)biphenyl 8 4-(trans-4-(3-fluoropropyl)cyclohexyl)-4'-(trans-4-pentylcyclohexyl)biphenyl C 61 Sx 236 N 314 I 9 4-(trans-4-(3-fluoropropyl)cyclohexyl)-4'-(trans-4-nonylcyclohexyl)biphenyl 10 4- (trans-4-(5-fluoropentyl)cyclohexyl)-4'-(trans-4-propylcyclohexyl)biphenyl C-Sx 52

N-I 303

11 4-(trans-4-(8-fluorooctyl)cyclohexyl)-4'-(trans-4-ethylcyclohexyl)biphenyl 12 4-(trans-4-(8-fluorooctyl)cyclohexyl)- 4'-(trans-4-heptylcyclohexyl)biphenyl 13 4-(trans-4-(4-fluorobutyl)cyclohexyl)-4'-(trans-4-ethoxycyclohexyl)biphenyl 14 4-(trans-4-(2-fluoroethyl)cyclohexyl)-4'-(trans-4-propoxymethylcyclohexyl)biphenyl

N-I 292

15 4-(trans-4-(5-fluoropentyl)cyclohexyl)-4'-(trans-4-ethenylcyclohexyl)biphenyl 16 (E)-4-(trans-4-(3-fluoropropyl)cyclohexyl)-4'-(trans-4-(1-propenyl)cyclohexyl)biphenyl 17 (E)-4-(trans-4-(2-fluoroethyl)cyclohexyl)-4'-(trans-4-(3-butenyl)cyclohexyl)biphenyl 18 4-(trans-4-(4-fluorobutyl)cyclohexyl)-4'-(trans-4-(2-propenyloxymethyl)cyclohexyl)biphenyl 19 4-(trans-4-(5-bromopentyl)cyclohexyl)-4'-(trans-4-propylcyclohexyl)biphenyl 20 4-(trans-4-(4-fluorobutyl)cyclohexyl)-4'-(2-(trans-4-propylcyclohexyl)ethyl)biphenyl 21 4-(trans-4-(2-fluoroethyl)cyclohexyl)-4'-(2-(trans-4-pentylcyclohexyl)ethyl)biphenyl 22 4-(trans-4-(5-fluoropentyl)cyclohexyl)-4'-(2-(trans-4-methoxypropylcyclohexyl)ethyl)biphenyl 23 4-(2-(trans-4-fluoromethylcyclohexyl)ethyl)-4'-(trans-4-pentylcyclohexyl)biphenyl 24 4-(2-(trans-4-(7-fluoroheptyl)cyclohexyl)ethyl)-4'-(trans-4-ethylcyclohexyl)biphenyl 25 (E)-4-(2-(trans-4-(3-fluoropropyl)cyclohexyl)ethyl)-4'-(trans-4-(1-butenyl)cyclohexyl)biphenyl 26 4-(2-(trans-4-(5-fluoropentyl)cyclohexyl)ethyl)-4'-(trans-4-(2-propenyl)cyclohexyl)biphenyl 27 4-(2-(trans-4-chloromethylcyclohexyl)ethyl)-4'-(trans-4-propylcyclohexyl)biphenyl 28 4-(2-(trans-4-chloromethylcyclohexyl)ethyl)-4'-(trans-4-butylcyclohexyl)biphenyl 29 4-(3-fluoropropyl)-4'''-ethyl-1,1':4',1'':4'',1'''-quaterphenyl 30 4-(trans-4-(4-(4-fluorobutyl)phenyl)cyclohexyl)-4'-pentylbiphenyl 31 (2-fluoroethyl)-4-(trans-4-(trans-4-(4-methylphenyl)cyclohexyl)cyclohexyl)benzene 32 (trans-4-fluoromethylcyclohexyl)-4-(trans-4-(butylphenyl)cyclohexyl)benzene 33 (trans-4-(3-fluoropropyl)cyclohexyl)-4-(trans-4-(trans-4-propylcyclohexyl)cyclohexyl)benzene 34 4-(5-fluoropentyl)-4'''-pentyl-1,1':4',1'':4'',1'''-quatercyclohexane

EXAMPLE 2

Preparation of 4-(trans-4-(3-fluoropropyl)cyclohexyl)-2'-fluoro-4'-(trans-4-pentylcyclohexyl)biphenyl (in general formula (1), R is $C_5H_{11}$, m is 3, X is F, both $A_1$ and $A_4$ are trans-1,4-cyclohexylene groups, $A_2$ is a 2-fluoro-1,4-phenylene group, $A_3$ is a 1,4-phenylene group, all of $Z_1$, $Z_2$, and $Z_3$ are covalent bonds)(No. 35)

4-(trans-4-(3-hydroxypropyl)cyclohexyl)-2'-fluoro-4'-(trans-4-pentylcyclohexyl)biphenyl 3.2 g (0.007 mol) and dichloromethane 30 ml were mixed. To the mixture, a solution of DAST 1.7 g (0.011 mol) in dichloromethane 4 ml were added dropwise to maintain the temperature at −50 °C., and stirred for 30 minutes at the same temperature. Then, the temperature was increased slowly and the mixture was stirred for 5 hours at room temperature.

The reaction mixture was poured into ice water 50 ml and extracted with dichloromethane 60 ml. The obtained organic phase was washed with water three times and dried over anhydrous magnesium sulfate. The solvent was distilled out under reduced pressure, the residue was chromatographed over silica gel (elate: toluene/heptane) to obtain 2.7 g of crude 4-(trans-4-(3-fluoropropyl)cyclohexyl)-2'-fluoro-4'-(trans-4-pentylcyclohexyl)biphenyl. The resulting compound was recrystallized from ethyl acetate, and the title compound 1.4 g (yield: 43.6%) was obtained.

Moreover, the structure was supported by each spectrum data.

Mass spectrometric analysis: 466 ($M^+$)

$^1$H-NMR (CDCl$_3$, TMS internal standard)

δ (ppm)

0.84–2.62 (m, 35H)

4.45 (dt, 2H)

7.33 (m, 7H)

The following compounds are prepared according to the above method of Example 2 (No.36–No.68).

No.

36 4-(trans-4-(4-fluorobutyl)cyclohexyl)-2'-fluoro-4'-(trans-4-methylcyclohexyl)biphenyl 37 4-(trans-4-(5-fluoropentyl)cyclohexyl)-2'-fluoro-4'-(trans-4-ethylcyclohexyl)biphenyl 38 4-(trans-4-fluoromethylcyclohexyl)-2'-fluoro-4'-(trans-4-propylcyclohexyl)biphenyl 39 4-(trans-4-(4-fluorobutyl)cyclohexyl)-2'-fluoro-4'-(trans-4-butylcyclohexyl)biphenyl 40 4-(trans-4-fluoromethylcyclohexyl)-2'-fluoro-4'-(trans-4-butylcyclohexyl)biphenyl 41 4-(trans-4-fluoromethylcyclohexyl)-2'-fluoro-4'-(trans-4-pentylcyclohexyl)biphenyl 42 4-(trans-4-(3-bromopropyl)cyclohexyl)-2'-fluoro-4'-(trans-4-propylcyclohexyl)biphenyl 43 4-(trans-4-(4-fluorobutyl)cyclohexyl)-2'-fluoro-4'-(trans-4-ethenylcyclohexyl)biphenyl 44 2-fluoro-4-(trans-4-(2-fluoroethyl)cyclohexyl)-4'-(trans-4-ethylcyclohexyl)biphenyl 45 2-fluoro-4-(trans-4-(3-fluoropropyl)cyclohexyl-4'-(trans-4-propylcyclohexyl)biphenyl C 43 Sx 124 N 302 I 46 2-fluoro-4-(trans-4-(5-fluoropentyl)cyclohexyl)-4'-(trans-4-propylcyclohexyl)biphenyl C 79 Sx 118 N 294 I 47 2-fluoro-4-(trans-4-(6-fluorohexyl)cyclohexyl)-4'-(trans-4-pentylcyclohexyl)biphenyl 48 2-fluoro-4-(trans-4-(7-fluoroheptyl)cyclohexyl)-4'-(trans-4-octylcyclohexyl)biphenyl 49 2-fluoro-4-(trans-4-(3-fluoropropyl)cyclohexyl)-4'-(trans-4-butylcyclohexyl)biphenyl 50 2-fluoro-4-(trans-4-(5-fluoropentyl)cyclohexyl)-4'-(trans-4-methoxymethylcyclohexyl)biphenyl 51 4-(trans-4-fluoromethylcyclohexyl)-3'-fluoro-4'-(trans-4-propylcyclohexyl)biphenyl 52 4-(trans-4-(3-fluoropropyl)cyclohexyl)-3'-fluoro-4'-(trans-4-propylcyclohexyl)biphenyl 53 4-(trans-4-(6-fluorohexyl)cyclohexyl)-3'-fluoro-4'-(trans-4-butylcyclohexyl)biphenyl 54 4-(trans-4-(4-fluorobutyl)cyclohexyl)-3'-fluoro-4'-(trans-4-butylcyclohexyl)biphenyl 55 3-fluoro-4-(trans-4-(3-fluoropropyl)cyclohexyl)-4'-(trans-4-ethylcyclohexyl)biphenyl 56 3-fluoro-4-(trans-4-(4-fluorobutyl)cyclohexyl)-4'-(trans-4-butylcyclohexyl)biphenyl 57 (E)-3-fluoro-4-(trans-4-(2-fluoroethyl)cyclohexyl)-4'-(trans-4-(1-pentenyl)cyclohexyl)biphenyl 58 4-(trans-4-(5-fluoropentyl)cyclohexyl)-2',6'-difluoro-4'-(trans-4-methylcyclohexyl)biphenyl 59 4-(trans-4-(3-fluoropropyl)cyclohexyl)-2',5'-difluoro-4'-(trans-4-propylcyclohexyl)biphenyl 60 2,3-difluoro-4-(trans-4-(2-fluoroethyl)cyclohexyl)-4'-(trans-4-ethylcyclohexyl)biphenyl 61 3, 5-difluoro-4-(trans-4-(5-fluoropentyl)cyclohexyl)-4'-(trans-4-butylcyclohexyl)biphenyl 62 2-fluoro-4-(trans-4-(3-fluoropropyl)cyclohexyl)-2'-fluoro-4'-(trans-4-ethylcyclohexyl)biphenyl 63 2-fluoro-4-(trans-4-(3-fluoropropyl)cyclohexyl) -2'-fluoro-4'-(trans-4-propylcyclohexyl)biphenyl 64 2-fluoro-4-(trans-4-(2-fluoroethyl)cyclohexyl) -2'-fluoro -4'-(trans-4-butylcyclohexyl)biphenyl 65 2-fluoro-4-(trans-4-(5-fluoropentyl)cyclohexyl)-2'-fluoro-4'-(trans-4-pentylcyclohexyl)biphenyl 66 3-fluoro-4-(trans-4-(10-fluorodecyl)cyclohexyl)-2'-fluoro-4'-(trans-4-methylcyclohexyl)biphenyl 67 4-(trans-4-(7-fluoroheptyl)cyclohexyl)-3'-fluoro-4'-(2-(trans-4-ethylcyclohexyl)ethyl)biphenyl 68 2-fluoro-4-(2-(trans-4-(3-fluoropropyl)cyclohexyl)ethyl) -4'-(trans-4-pentylcyclohexyl)biphenyl

EXAMPLE 3

Preparation of 4-(5-fluoropentyl)-4'-(trans-4-(trans-4-propylcyclohexyl)cyclohexyl)biphenyl (in general formula (1), R is $C_3H_7$, m is 5, X is F, both $A_1$ and $A_2$ are trans-1,4-cyclohexylene groups, both $A_3$ and $A_4$ are 1,4-phenylene groups, and all of $Z_1$, $Z_2$, and $Z_3$ are covalent bonds)(No. 69)

4-(5-Hydroxypentyl)-4'-(trans-4-(trans-4-propylcyclohexyl)cyclohexyl)biphenyl 5.2 g (0.012 mol) and dichloromethane 45 ml were mixed. To the mixture, a solution of DAST 2.8 g (0.018 mol) in dichloromethane 6 ml were added dropwise to maintain the temperature at −50° C., and stirred for 30 minutes at the same temperature. Then, the temperature was increased slowly and the mixture was stirred for 6 hours at room temperature.

The reaction mixture was poured into ice water 100 ml and extracted with dichloromethane 100 ml.

The obtained organic phase was washed with water three times and dried over anhydrous magnesium sulfate. The solvent was distilled out under reduced pressure, the residue was chromatographed over silica gel (elute: toluene/heptane) to obtain 4.9 g of crude 4-(5-fluoropentyl)-4'-(trans-4-(trans-4-propylcyclohexyl)cyclohexyl)biphenyl. The resulting compound was recrystallized from ethyl acetate, and 2.0 g the title compound (yield: 38.5%) was obtained.

Moreover, the structure was supported by each spectrum data. Mass spectrometric analysis: 448 ($M^+$)

$^1$H-NMR (CDCl$_3$, TMS internal standard)

δ (ppm)

0.90–2.63 (m, 35H)

4.44 (dt, 2H)

7.38 (dd, 8H)

The following compounds are prepared according to the above method of Example 3 (No.70–No.107).

No.

70 4-(2-fluoroethyl)-4'-(trans-4-(trans-4-methylcyclohexyl)cyclohexyl)biphenyl 71 4-(3-fluoropropyl)-4'-(trans-4-(trans-4-ethylcyclohexyl)cyclohexyl)biphenyl 72 4-(4-fluorobutyl)-4'-(trans-4-(trans-4-propylcyclohexyl)cyclohexyl)biphenyl 73 4-(5-fluoropentyl)-4'-(trans-4-(trans-4-propylcyclohexyl)cyclohexyl)biphenyl 74 4-(7-fluoroheptyl)-4'-(trans-4-(trans-4-propylcyclohexyl)cyclohexyl)biphenyl 75 4-(4-fluorobutyl)-4'-(trans-4-(trans-4-butylcyclohexyl)cyclohexyl)biphenyl 76 4-(3-fluoropropyl)-4'-(trans-4-(trans-4-pentylcyclohexyl)cyclohexyl)biphenyl 77 (E)-4-(2-fluoroethyl)-4'-(trans-4-(trans-4-(3-pentenyl)cyclohexyl)cyclohexyl)biphenyl 78 (Z)-4-(4-fluorobutyl)-4'-(trans-4-(trans-4-(4-hexenyl)cyclohexyl)cyclohexyl)biphenyl 79 4-(3-bromopropyl)-4'-(trans-4-(trans-4-pentylcyclohexyl)cyclohexyl)biphenyl 80 4-chloromethyl-4'-(trans-4-(trans-4-propylcyclohexyl)cyclohexyl)biphenyl 81 4-(trans-4-(trans-4-(3-fluoropropyl)cyclohexyl)cyclohexyl)-4'-methylbiphenyl 82 4-(trans-4-(trans-4-(2-fluoroethyl)cyclohexyl)cyclohexyl)-4'-propylbiphenyl 83 4-(trans-4-(trans-4-fluoromethylcyclohexyl)cyclohexyl)-4'-butylbiphenyl 84 4-(trans-4-(trans-4-(5-fluoropentyl)cyclohexyl)cyclohexyl)-4'-pentylbiphenyl 85 4-(trans-4-(trans-4-(6-fluorohexyl)cyclohexyl)cyclohexyl)-4'-methoxybiphenyl 86 4-(3-fluoropropyl)-4'-(trans-4-(2-(trans-4-ethylcyclohexyl)ethyl)cyclohexyl)biphenyl 87 4-(4-fluorobutyl)-4'-(trans-4-(2-(trans-4-propylcyclohexyl)ethyl)cyclohexyl)biphenyl 88 4-(4-fluorobutyl)-4'-(trans-4-(2-(trans-4-pentylcyclohexyl)ethyl)cyclohexyl)biphenyl 89 4-fluoromethyl-4'-(trans-4-(2-(trans-4-propylcyclohexyl)ethyl)cyclohexyl)biphenyl 90 4-(trans-4-(2-(trans-4-(3-fluoropropyl)cyclohexyl)ethyl)cyclohexyl)-4'-ethylbiphenyl 91 4-(trans-4-(2-(trans-4-(5-fluoropentyl)cyclohexyl)ethyl)cyclohexyl)-4'-pentylbiphenyl 92 4-(2-(4-(trans-4-(trans-4-methylcyclohexyl)cyclohexyl)phenyl)ethyl)-(4-fluorobutyl)benzene 93 4-(2-(4-(trans-4-(trans-4-propylcyclohexyl)cyclohexyl)phenyl)ethyl)-fluoromethylbenzene 94 4-(2-(4-(trans-4- (trans-4-pentylcyclohexyl)cyclohexyl)phenyl)ethyl)-fluoromethylbenzene 95 4-(2-(4-(trans-4-(trans-4-(3-butenyl)cyclohexyl)cyclohexyl)phenyl)ethyl) fluoromethylbenzene 96 4-hexyl-(2-(4-(trans-4-(trans-4-(2-fluoroethyl)cyclohexyl)cyclohexyl)phenyl)ethyl)benzene 97 4-ethoxyethyl-(2-(4-(trans-4-(trans-4-(4-fluorobutyl)cyclohexyl)cyclohexyl)phenyl)ethyl)benzene 98 3-fluoro-4-(7-fluoroheptyl)-4'-(trans-4-(trans-4-pentylcyclohexyl)cyclohexyl)biphenyl 99 4-(4-fluorobutyl)-2'-fluoro-4'-(trans-4-(trans-4-propylcyclohexyl)cyclohexyl)biphenyl 100 4-(4-fluorobutyl)-2'-fluoro-4'-(trans-4-(trans-4-butylcyclohexyl)cyclohexyl)biphenyl 101 3-fluoro-4-(trans-4-(trans-4-(5-fluoropentyl)cyclohexyl)cyclohexyl)-4'-ethylbiphenyl 102 4-(7-fluoroheptyl)-2'-fluoro-4'-(trans-4-(2-(trans-4-methylcyclohexyl)ethyl)cyclohexyl)biphenyl 103 3,5-difluoro-4-(4-fluorobutyl)-4'-(trans-4-(trans-4-propylcyclohexyl)cyclohexyl)biphenyl 104 3-fluoro-4-fluoromethyl-2'-fluoro-4'-(trans-4-(2-(trans-4-nonylcyclohexyl)ethyl)cyclohexyl)biphenyl 105 3-fluoro-4-(trans-4-(2-(trans-4-fluoromethylcyclohexyl)ethyl)cyclohexyl)-4'-methylbiphenyl 106 4-(2-(2-fluoro-4-(trans-4-(trans-4-ethenylcyclohexyl)cyclohexyl)phenyl)ethyl)-fluoromethylbenzene 107 2-fluoro-4-butyl-(2-(2-fluoro-4-(trans-4-(trans-4-(2-fluoroethyl)cyclohexyl)cyclohexyl)phenyl)ethyl)benzene

EXAMPLE 4

Preparation of 4-(3-fluoropropyl)-4'-(2-(trans-4-(trans-4-methylcyclohexyl)cyclohexyl)ethyl)biphenyl (in general formula (1), R is $CH_3$, m is 3, X is F, both $A_1$ and $A_2$ are trans-1,4-cyclohexylene groups, both $A_3$ and $A_4$ are 1,4-phenylene groups, both $Z_1$ and $Z_3$ are covalent bonds, $Z_2$ is —$(CH_2)_2$—)(No. 108) 4-(3-Hydroxypropyl)-4'-(2-(trans-4-(trans-4-methylcyclohexyl)cyclohexyl)ethyl)biphenyl 5.9 g (0.014 mol) and dichloromethane 60 ml were mixed. To the mixture, a solution of DAST 3.4 g (0.021 mol) in dichloromethane 7 ml were added dropwise to maintain the temperature at −50° C., and stirred for 30 minutes at the same temperature. Then, the temperature was increased slowly and the mixture was stirred for 7 hours at room temperature.

The reaction mixture was poured into ice water 150 ml and extracted with dichloromethane 120 ml.

The obtained organic phase was washed with water three times and dried over anhydrous magnesium sulfate. The solvent was distilled out under reduced pressure, the residue was chromatographed over silica gel (elute: toluene/heptane) to obtain 5.0 g of crude 4-(3-fluoropropyl)-4'-(2-(trans-4-(trans-4-methylcyclohexyl)cyclohexyl)ethyl)biphenyl. The resulting compound was recrystallized from ethyl acetate, and 3.2 g of the title compound (yield: 54.2%) was obtained.

Moreover, the structure was supported by each spectrum data.

Mass spectrometric analysis: 420 ($M^+$)

$^1$H-NMR ($CDCl_3$, TMS internal standard)

δ (ppm)

0.65–2.75 (m, 31H)

4.43 (dt, 2H)

7.38 (dd, 8H)

The following compounds are prepared according to the above method of Example 4 (No.109–No.148).

No.

109 4-fluoromethyl-4'-( 2-(trans-4-(trans-4-propylcyclohexyl)cyclohexyl)ethyl)biphenyl 110 4-(3-fluoropropyl)-4'-(2-(trans-4-(trans-4-propylcyclohexyl)cyclohexyl)ethyl)biphenyl 111 4-(5-fluoropentyl)-4'-(2-(trans-4-(trans-4-propylcyclohexyl)cyclohexyl)ethyl)biphenyl 112 4-fluoromethyl-4'-(2-(trans-4-(trans-4-butylcyclohexyl)cyclohexyl)ethyl)biphenyl 113 4-(2-fluoroethyl)-4'-(2-(trans-4-(trans-4-pentylcyclohexyl)cyclohexyl)ethyl)biphenyl 114 4-(8-fluorooctyl)-4'-(2- (trans-4-(trans-4-decylcyclohexyl)cyclohexyl)ethyl)biphenyl 115 (E)-4-(2-fluoroethyl)-4'-(2-(trans-4-(trans-4-(1-propenyl)cyclohexyl)cyclohexyl)ethyl)biphenyl 116 (Z)-4-(4-fluorobutyl)-4'-(2-(trans-4-(trans-4-(2-butenyl)cyclohexyl)cyclohexyl)ethyl)biphenyl 117 (E)-4-fluoromethyl-4'-(2-(trans-4-(trans-4-(3-pentenyl)cyclohexyl)cyclohexyl)ethyl)biphenyl 118 4-(6-fluorohexyl)-4'-(2-(trans-4-(trans-4-methoxycyclohexyl)cyclohexyl)ethyl)biphenyl 119 4-(2-fluoroethyl)-4'-(2-(trans-4-(trans-4-methoxypropylcyclohexyl)cyclohexyl)ethyl)biphenyl 120 4-chloromethyl-4'-(2-(trans-4-(trans-4-propylcyclohexyl)cyclohexyl)ethyl)biphenyl 121 4-(2-chloroethyl)-4'-(2-(trans-4-(trans-4-butylcyclohexyl)cyclohexyl)ethyl)biphenyl 122 4-(3-iodopropyl)-4'-(2- (trans-4-(trans-4-pentylcyclohexyl)cyclohexyl)ethyl)biphenyl 123 4-(2-(trans-4-(trans-4-(2-fluoroethyl)cyclohexyl)cyclohexyl)ethyl)-4'-ethylbiphenyl 124 4-(2-(trans-4-(trans-4-(4-fluorobutyl)cyclohexyl)cyclohexyl)ethyl)-4'-propylbiphenyl 125 4-(2-(trans-4-(trans-4-(4-fluorobutyl)cyclohexyl)cyclohexyl)ethyl)-4'-butylbiphenyl 126 4-(2-(trans-4-(trans-4-(3-fluoropropyl)cyclohexyl)cyclohexyl)ethyl)-4'-pentylbiphenyl 127 4-(2-(trans-4-(trans-4-(5-fluoropentyl)cyclohexyl)cyclohexyl)ethyl)-4'-methylbiphenyl 128 4-(2-(trans-4-(trans-4-(3-fluoropropyl)cyclohexyl)cyclohexyl)ethyl)-4'-pentyloxybiphenyl 129 4-(2-(trans-4-(trans-4-(3-fluoropropyl)cyclohexyl)cyclohexyl)ethyl)-4'-ethoxymethylbiphenyl 130 4-(2-(trans-4-(trans-4-(5-fluoropentyl)cyclohexyl)cyclohexyl)ethyl)-4'-methoxyethylbiphenyl 131 4-(2- (4-(trans-4-methylcyclohexyl)phenyl)ethyl)-(trans-4-(3-fluoropropyl)cyclohexyl)benzene 132 4-(2-(4-(trans-4-propylcyclohexyl)phenyl)ethyl)-(trans-4-(2-fluoroethyl)cyclohexyl)benzene 133 4-(2-(4-(trans-4-butylcyclohexyl)phenyl)ethyl)-(trans-4-(5-fluoropentyl)cyclohexyl)benzene 134 4-(2-(4-(trans-4-hexylcyclohexyl)phenyl)ethyl)-(trans-4-(4-fluorobutyl)cyclohexyl)benzene 135 4-(2-(4-(trans-4-ethenylcyclohexyl)phenyl)ethyl)-(trans-4-(3-fluoropropyl)cyclohexyl)benzene 136 4-(2-(4-(trans-4-(3-butenyl)cyclohexyl)phenyl)ethyl)-(trans-4-(2-fluoroethyl)cyclohexyl)benzene 137 4-(2-(4-(trans-4-metoxyethylcyclohexyl)phenyl)ethyl)-(trans-4-(5-fluoropentyl)cyclohexyl)benzene 138 4- (2-(4- (trans-4-propoxycyclohexyl)phenyl)ethyl)-(trans- 4-(3-fluoropropyl)cyclohexyl)benzene 139 4-(2-fluoroethyl)-3'-fluoro-4'-(2-(trans-4-(trans-4-propylcyclohexyl)cyclohexyl)ethyl)biphenyl 140 3-fluoro-4-(3-fluoropropyl)-4'-(2-(trans-4-(trans-4-pentylcyclohexyl)cyclohexyl)ethyl)biphenyl 141 2-fluoro-4-(5-fluoropentyl)-2'-fluoro-4'-(2-(trans-4-(trans-4-pentylcyclohexyl)cyclohexyl)ethyl)biphenyl 142 4-chloromethyl-2'-fluoro-4'-(2-(trans-4-(trans-4-propylcyclohexyl)cyclohexyl)ethyl)biphenyl 143 2-fluoro-4-(2- (trans-4-(trans-4- (4-fluorobutyl)cyclohexyl)cyclohexyl)ethyl)-4'-methylbiphenyl 144 3-fluoro-4-(2-(trans-4-(trans-4-(7-fluoroheptyl)cyclohexyl)cyclohexyl)ethyl)-4'-ethylbiphenyl 145 3-fluoro-4-(2-(trans-4-(trans-4-(3-fluoropropyl)cyclohexyl)cyclohexyl)ethyl)-2'-fluoro-4'-butoxybiphenyl 146 4-(2-(2-fluoro-4-(trans-4-pentylcyclohexyl)phenyl)ethyl)-(trans-4-fluoromethylcyclohexyl)benzene 147 2-fluoro-4-(2-(2-fluoro-4-(trans-4-propylcyclohexyl)phenyl)ethyl)-(trans-4-(3-fluoropropyl)cyclohexyl)benzene 148 3-fluoro-4-(2-(2-fluoro-4-(trans-4-propylcyclohexyl) phenyl)ethyl)-(trans-4-(5-fluoropentyl)cyclohexyl) benzene

EXAMPLE 5

Preparation of 4-(trans-4-(2-(trans-4-(trans-4-ethylcyclohexyl)cyclohexyl)ethyl)cyclohexyl)-(4-fluorobutyl)benzene (in general formula (1), R is $C_2H_5$, m is 4, X is F, $A_1$, $A_2$ and $A_3$ are trans-1,4-cyclohexylene groups, $A_4$ is a 1,4-phenylene group, both $Z_1$ and $Z_3$ are covalent bonds, $Z_2$ is —$(CH_2)_2$—)(No. 149)

4-(trans-4-(2-(trans-4-ethylcyclohexyl)cyclohexyl)ethyl) cyclohexyl)-(4-hydroxybutyl)benzene 4.4 g (0.010 mol) and dichloromethane 45 ml were mixed.

To the mixture, a solution of DAST 2.4 g (0.015 mol) in dichloromethane 5 ml were added dropwise to maintain the temperature at −50° C., and stirred for 30 minutes at the same temperature. Then, the temperature was increased slowly and the mixture was stirred for 5 hours at room temperature.

The reaction mixture was poured into ice water 100 ml and extracted with dichloromethane 90 ml. The obtained organic phase was washed with water three times and dried over anhydrous magnesium sulfate. The solvent was distilled out under reduced pressure, and the residue was chromatographed over silica gel (elute: toluene/heptane) to obtain 3.9 g of crude 4-(trans-4-(2-(trans-4-(trans-4-ethylcyclohexyl)cyclohexyl)ethyl)cyclohexyl)-(4-fluorobutyl)benzene. The resulting compound was recrystallized from ethyl acetate, and 1.9 g of the title compound (yield: 43.2%) was obtained.

Moreover, the structure was supported by each spectrum data.

Mass spectrometric analysis: 454 ($M^+$)

$^1$H-NMR (CDCl$_3$, TMS internal standard)

δ (ppm)

0.69–2.53 (m, 45H)

4.45 (dt, 2H)

7.10 (s, 4H)

The following compounds are prepared according to the above method of Example 5 (No.150–No.205).

No.

150 4-(trans-4-(2-(trans-4-(trans-4-methyleyclohexyl) cyclohexyl)ethyl)cyclohexyl)-(3-fluoropropyl)benzene 151 4-(trans-4-(2-(trans-4-(trans-4-propylcyclohexyl) cyclohexyl)ethyl)cyclohexyl)-(5-fluoropentyl)benzene 152 4-(trans-4-(2-(trans-4-(trans-4-propylcyclohexyl) cyclohexyl)ethyl)cyclohexyl)-fluoromethylbenzene 153 4-(trans-4-(2-(trans-4-(trans-4-pentylcyclohexyl) cyclohexyl)ethyl)cyclohexyl)-( 2-fluoroethyl)benzene 154 4-(trans-4-(2-(trans-4-(trans-4-butylcyclohexyl) cyclohexyl)ethyl)cyclohexyl)-fluoromethylbenzene 155 4-(trans-4-(2-(trans-4-(trans-4-pentylcyclohexyl) cyclohexyl)ethyl)cyclohexyl)-fluoromethylbenzene 156 4-(trans-4-(2-(trans-4-(trans-4-nonylcyclohexyl) cyclohexyl)ethyl)cyclohexyl)-fluoromethylbenzene 157 (Z)-4-(trans-4-(2-(trans-4-(trans-4-(2-pentenyl) cyclohexyl)cyclohexyl)ethyl)cyclohexyl)-(3-fluoropropyl)benzene 158 4-(trans-4-(2-(trans-4-(trans-4-propylcyclohexyl) cyclohexyl)ethyl)cyclohexyl)-(4-chlorobutyl)benzene 159 4-(trans-4-(2-(trans-4-(trans-4-pentylcyclohexyl) cyclohexyl)ethyl)cyclohexyl)-(4-chlorobutyl)benzene 160 4-methyl-(trans-4-(2-(trans-4-(trans-4-fluoromethylcyclohexyl)cyclohexyl)ethyl)cyclohexyl) benzene 161 4-propyl-(trans-4-(2-(trans-4-(trans-4-(2-fluoroethyl) cyclohexyl)cyclohexyl)ethyl)cyclohexyl)benzene 162 4-pentyl-(trans-4-(2-(trans-4-(trans-4-(5-fluoropentyl)cyclohexyl)cyclohexyl)ethyl)cyclohexyl) benzene 163 4-methoxybutyl-(trans-4-(2-(trans-4-(trans-4-(3-fluoropropyl)cyclohexyl)cyclohexyl)ethyl)cyclohexyl) benzene 164 4-(trans-4-(trans-4-(trans-4-ethylcyclohexyl) cyclohexyl)cyclohexyl)-(2-fluoroethyl)benzene 165 4-(trans-4-(trans-4-(trans-4-ethylcyclohexyl) cyclohexyl)cyclohexyl)-(3-fluoropropyl)benzene 166 4-(trans-4-(trans-4-(trans-4-propylcyclohexyl) cyclohexyl)cyclohexyl)-fluoromethylbenzene 167 4-(trans-4-(trans-4- (trans-4-propylcyclohexyl) cyclohexyl)cyclohexyl)-(4-fluorobutyl)benzene 168 4-(trans-4-(trans-4-(trans-4-pentylcyclohexyl) cyclohexyl)cyclohexyl)-fluoromethylbenzene 169 4-(trans-4-(trans-4-(trans-4-ethenylcyclohexyl) cyclohexyl)cyclohexyl)-(5-fluoropentyl)benzene 170 4-(trans-4-(trans-4-(trans-4-methylcyclohexyl) cyclohexyl)cyclohexyl)-(4-chlorobutyl)benzene 171 4-(trans-4-(trans-4-(trans-4- (3-butenyl)cyclohexyl) cyclohexyl)cyclohexyl)-(3-fluoropropyl)benzene 172 4-methyl-(trans-4-(trans-4-(trans-4-(3-fluoropropyl) cyclohexyl)cyclohexyl)cyclohexyl)benzene 173 4-ethyl-(trans-4-(trans-4-(trans-4-(3-fluoropropyl) cyclohexyl)cyclohexyl)cyclohexyl)benzene 174 4-propyl-(trans-4-(trans-4-(trans-4-(4-fluorobutyl) cyclohexyl)cyclohexyl)cyclohexyl)benzene 175 4-propyl-(trans-4-(trans-4-(trans-4-(5-fluoropentyl) cyclohexyl)cyclohexyl)cyclohexyl)benzene 176 4-butyl-(trans-4-(trans-4-(trans-4-(4-fluorobutyl) cyclohexyl)cyclohexyl)cyclohexyl)benzene 177 4-heptyl-(trans-4-(trans-4-(trans-4-(8-fluorooctyl) cyclohexyl)cyclohexyl)cyclohexyl)benzene 178 (E)-4-(3-pentenyl)-(trans-4-(trans-4-(trans-4-(2-fluoroethyl)cyclohexyl)cyclohexyl)cyclohexyl) benzene 179 4-pentyloxy-(trans-4-(trans-4-(trans-4-(4-fluorobutyl)cyclohexyl)cyclohexyl)cyclohexyl) benzene 180 4-(2-(trans-4-(trans-4-(trans-4-ethylcyclohexyl) cyclohexyl)cyclohexyl)ethyl)-(2-fluoroethyl)benzene 181 4-(2-(trans-4- (trans-4-(trans-4-ethylcyclohexyl) cyclohexyl)cyclohexyl)ethyl)-(4-fluorobutyl)benzene 182 4-(2-(trans-4-(trans-4-(trans-4-propylcyclohexyl) cyclohexyl)cyclohexyl)ethyl)-fluoromethylbenzene 183 4-(2-(trans-4-(trans-4-(trans-4-propylcyclohexyl) cyclohexyl)cyclohexyl)ethyl)-(2-fluoroethyl)benzene fluoromethylbenzene 184 4-(2-(trans-4-(trans-4-(trans-4-propylcyclohexyl) cyclohexyl)cyclohexyl)ethyl)-(4-fluorobutyl)benzene 185 4-(2-(trans-4-(trans-4-(trans-4-butylcyclohexyl) cyclohexyl)cyclohexyl)ethyl)-fluoromethylbenzene 186 4-(2-(trans-4-(trans-4-(trans-4-pentylcyclohexyl) cyclohexyl)cyclohexyl)ethyl)-fluoromethylbenzene 187 4-(2-(trans-4-(trans-4-(trans-4-pentylcyclohexyl) cyclohexyl)cyclohexyl)ethyl)-(3-fluoropropyl)benzene 188 (E)-4-(2-(trans-4-(trans-4-(trans-4-(1-propenyl) cyclohexyl)cyclohexyl)cyclohexyl)ethyl)-(5-fluoropentyl)benzene 189 4-ethyl-(2-(trans-4-(trans-4-(trans-4-(3-fluoropropyl) cyclohexyl)cyclohexyl)cyclohexyl)ethyl)benzene 190 4-propyl-(2-(trans-4-(trans-4-(trans-4-(5-fluoropentyl)cyclohexyl)cyclohexyl)cyclohexyl)ethyl) benzene 191 4-butyl-(2-(trans-4-(trans-4-(trans-4-(4-fluorobutyl) cyclohexyl)cyclohexyl)cyclohexyl)ethyl)benzene 192 (E)-4-(1-butenyl)-(2- (trans-4-(trans-4-(trans-4-(2-fluoroethyl)cyclohexyl)cyclohexyl)cyclohexyl)ethyl) benzene 193 4-methoxypentyl-(2-(trans-4-(trans-4-(trans-4-(6-fluorohexyl)cyclohexyl)cyclohexyl)cyclohexyl)ethyl) benzene 194 4-(trans-4-(trans-4-(2-(trans-4-propylcyclohexyl) ethyl)cyclohexyl)cyclohexyl)-fluoromethylbenzene 195 4-(trans-4-(trans-4-(2-(trans-4-butylcyclohexyl) ethyl)cyclohexyl)cyclohexyl)-(5-fluoropentyl)benzene 196 4-(trans-4-(trans-4-(2-(trans-4-heptylcyclohexyl) ethyl)cyclohexyl)cyclohexyl)-(2-fluoroethyl)benzene 197 4-(trans-4-(trans-4-(2-(trans-4-ethoxyethylcyclohexyl)ethyl)cyclohexyl)cyclohexyl)-(3-fluoropropyl)benzene 198 4-methyl-(trans-4-(trans-4-(2-trans-4-(5-fluoropentyl)cyclohexyl)ethyl)cyclohexyl)cyclohexyl) benzene 199 4-propyl-(trans-4-(trans-4-(2-(trans-4-(4-fluorobutyl) cyclohexyl)ethyl)cyclohexyl)cyclohexyl)benzene 200 4-pentyl-(trans-4-(trans-4-(2-(trans-4-(5-fluoropentyl)cyclohexyl)ethyl)cyclohexyl)cyclohexyl) benzene 201 4-(2-propenyl)-(trans-4-(trans-4-(2-trans-4-(3-fluoropropyl)cyclohexyl)ethyl)cyclohexyl)cyclohexyl) benzene 202 2-fluoro-4-(trans-4-(2- (trans-4-(trans-4-ethylcyclohexyl)cyclohexyl)ethyl)cyclohexyl)-(2-fluoroethyl)benzene 203 2,6-difluoro-4-(trans-4-(trans-4-(trans-4-pentylcyclohexyl)cyclohexyl)cyclohexyl)-(3-fluoropropyl)benzene 204 2-fluoro-4-propyl-(trans-4-(trans-4-(trans-4-(5-fluoropentyl)cyclohexyl)cyclohexyl)cyclohexyl) benzene 205 3-fluoro-(2-(trans-4-(trans-4-(trans-4-methylcyclohexyl)cyclohexyl)cyclohexyl)ethyl)-fluoromethylbenzene

EXAMPLE 6

Preparation of 4-(trans-4-(2-fluoroethyl)cyclohexyl)-4"-ethyl- 1,1':4',1"-terphenyl (in general formula (1), R is $C_2H_5$, m is 2, X is F, $A_1$, $A_2$ and $A_3$ are 1,4-phenylene groups, $A_4$ is a trans-1,4-cyclohexylene group, $Z_1$, $Z_2$ and $Z_3$ are covalent bonds)(No. 206)

4-(trans-4-(2-hydroxyethyl)cyclohexyl)-4"-ethyl-1,1':4', 1"-terphenyl 4.8 g (0.013 mol) and dichloromethane 50 ml were mixed. To the mixture, a solution of DAST 3.0 g (0.019 mol) in dichloromethane 6 ml were added dropwise to maintain the temperature at -50 ° C, and stirred for 30 minutes at the same temperature. Then, the temperature was increased slowly and the mixture was stirred for 5 hours at room temperature.

The reaction mixture was poured into ice water 100 ml and extracted with dichloromethane 100 ml.

The obtained organic phase was washed with water three times and dried over anhydrous magnesium sulfate.

The solvent was distilled out under reduced pressure, and the residue was chromatographed over silica gel (elute: toluene/heptane) to obtain 4.3 g of crude 4-(trans-4-(2-fluoroethyl)cyclohexyl)-4"-ethyl-1,1':4',1"-terphenyl. The resulting compound was recrystallized from ethyl acetate, and 1.7 g the title compound (yield: 35.4%) was obtained.

Moreover, the structure was supported by each spectrum data.

Mass spectrometric analysis: 386 ($M^+$)

$^1$H-NMR (CDCl$_3$, TMS internal standard)

δ (ppm)

0.80–2.76 (m, 27H)

4.44 (dt, 2H)

7.30–7.75 (m, 12H)

The following compounds are prepared according to the above method of Example 6 (No.207–No.247).

No.

207 4-(trans-4-(3-fluoropropyl)cyclohexyl)-4"-ethyl-1, 1':4',1"-terphenyl 208 4-(trans-4-(4-fluorobutyl)cyclohexyl)-4"-propyl-1, 1':4',1"-terphenyl 209 4-(trans-4-(2-fluoroethyl)cyclohexyl)-4"-pentyl-1,1':4',1"-terphenyl 210 $^4$-(trans-4-(4-fluorobutyl)cyclohexyl)-4"-heptyloxy-1,1':4',1"-terphenyl 211 4-(3-fluoropropyl)-4"-(trans-4-methylcyclohexyl)-1, 1':4',1"-terphenyl 212 4-(5-fluoropentyl)-4"-(trans-4-ethylcyclohexyl)-1, 1':4',1"-terphenyl 213 4-(4-fluorobutyl)-4"-(trans-4-propylcyclohexyl)-1, 1':4',1"-terphenyl 214 4-(4-fluorobutyl)-4"-(trans-4-butylcyclohexyl)-1, 1':4',1"-terphenyl 215 4-(5-fluoropentyl)-4"-(trans-4-pentylcyclohexyl)-1, 1': 4',1"-terphenyl 216 4-(4-fluoromethyl)-4"-(trans-4-decylcyclohexyl)-1, 1':4',1"-terphenyl 217 4-(7-fluoroheptyl)-4"-(trans-4-(4-pentenyl) cyclohexyl)-1,1':4',1"-terphenyl 218 4-(3-chloropropyl)-4"-(trans-4-butylcyclohexyl)-1, 1':4',1"-terphenyl 219 4-(trans-4-(4-fluorobutyl)cyclohexyl)-4'-(2-(4-ethylphenyl)ethyl)biphenyl 220 4-(trans-4-(3-fluoropropyl)cyclohexyl)-4'-(2-(4-propylphenyl)ethyl)biphenyl 221 4-(trans-4-(6-fluorohexyl)cyclohexyl)-4'-(2-(4-butylphenyl)ethyl)biphenyl 222 4-(trans-4-(2-fluoroethyl)cyclohexyl)-4'-(2-(4-hexylphenyl)ethyl)biphenyl 223 (Z)-4-(trans-4-(4-fluoromethylcyclohexyl)-4'-(2-(4-(4-hexenyl)phenyl)ethyl)biphenyl 224 4-(2-(trans-4-(4-fluorobutyl)cyclohexyl)ethyl)-4"-propyl-1,1':4',1"-terphenyl 225 4-(2-(trans-4-(5-fluoropentyl)cyclohexyl)ethyl)-4"-pentyl-1,1':4',1"-terphenyl 226 4-(2-(trans-4-(2-fluoroethyl)cyclohexyl)ethyl)-4"-heptyl-1,1':4',1"-terphenyl 227 4-(2-(trans-4-(3-fluoropropyl)cyclohexyl)ethyl)-4"-propoxymethyl-1,1':4',1"-terphenyl 228 4-(2-(4-(5-fluoropentyl)phenyl)ethyl)-4'-(trans-4-methylcyclohexyl)biphenyl 229 4-(2-(4-(2-fluoroethyl)phenyl)ethyl)-4'-(trans-4-ethylcyclohexyl)biphenyl 230 4-(2-(4-fluoromethylphenyl)ethyl)-4'-(trans-4-nonylcyclohexyl)biphenyl 231 (E) -4-(2-(4- (3-fluoropropyl)phenyl) ethyl) -4'-(trans-4-(1-butenyl)cyclohexyl)biphenyl 232 4-(2-fluoroethyl)-4"-(2-(trans-4-propylcyclohexyl) ethyl)-1,1':4',1"-terphenyl 233 4-(5-fluoropentyl)-4"-(2-(trans-4-propylcyclohexyl) ethyl)-1,1':4',1"-terphenyl 234 4-(3-fluoropropyl)-4"-(2-(trans-4-heptylcyclohexyl) ethyl)-1,1':4',1"-terphenyl 235 4-(4-fluorobutyl)-4"-(2-(trans-4-methoxymethylcyclohexyl)ethyl)-1,1':4',1"-terphenyl 236 4-(2-(4- (trans-4-(3-fluoropropyl)cyclohexyl)phenyl) ethyl)-4'-methylbiphenyl 237 4-(2-(4-(trans-4-(5-fluoropentyl)cyclohexyl)phenyl) ethyl)-4'-ethylbiphenyl 238 4-(2-(4- (trans-4-(2-fluoroethyl) cyclohexyl)phenyl) ethyl)-4'-octylbiphenyl 239 4-fluoromethyl-4'-(2-(4-(trans-4-ethylcyclohexyl) phenyl)ethyl)biphenyl 240 4-(4-fluorobutyl)-4'-(2-(4-(trans-4-ethylcyclohexyl) phenyl)ethyl)biphenyl 241 4-(6-fluorohexyl)-4'-(2-(4-(trans-4-hexylcyclohexyl) phenyl)ethyl)biphenyl 242 4-(3-fluoropropyl)-4'-(2-(4-(trans-4-(4-pentenyl) cyclohexyl)phenyl)ethyl)biphenyl 243 2-fluoro-4-(trans-4-(4-fluorobutyl)cyclohexyl)-2'-fluoro-4"-butyl-1,1':4',1"-terphenyl 244 3-fluoro-4-(5-fluoropentyl)-2'-fluoro-2"-fluoro-4'"-(trans-4-ethylcyclohexyl)-1,1':4',1"-terphenyl 245 4-(2-(2-fluoro-4-(trans-4-(3-fluoropropyl) cyclohexyl)phenyl)ethyl)-4'-methylbiphenyl 246 4-fluoromethyl-3'-fluoro-4'-(2-(2-(fluoro-4-(trans-4-propylcyclohexyl)phenyl)ethyl)biphenyl 247 4-chloromethyl-3'-fluoro-4'-(2-(2-fluoro-4-(trans-4-propylcyclohexyl)phenyl)ethyl)biphenyl 248 2-(4-(trans-4-(5-fluoropentyl)cyclohexyl)phenyl)-5-(4-propylphenyl)pylimidine 249 2-(trans-4-(4'-(3-fluoropropyl)biphenyl-4-yl) cyclohexyl)-5-pentyldioxane In the following, the use of the compounds of the present invention as constituents of liquid crystal compositions are exemplified. In each use examples, NI shows nematic phase-isotropic phase transition temperature (° C.), $\Delta \epsilon$ shows a dielectric anisotropy value, $\Delta n$ shows a refractive index anisotropy value, $\eta$ shows a viscosity at 20° C. (mPa.s) and $V_{10}$ shows a threshold voltage (V).

EXAMPLE 7 (use example 1)

Liquid crystal composition containing the following compound of a cyanophenylcyclohexane type:

| | |
|---|---|
| 4-(trans-4-propylcyclohexyl)benzonitrile | 24% by weight |
| 4-(trans-4-pentylcyclohexyl)benzonitrile | 36% by weight |
| 4-(trans-4-heptylcyclohexyl)benzonitrile | 25% by weight |
| 4-(trans-4-pentylcyclohexyl)-4'-cyanobiphenyl | 15% by weight |

The above composition has the following values of physical properties.

NI: 72.4, $\Delta\epsilon$: 11.0, $\Delta n$: 0.137, $\eta$: 27.2, $V_{10}$: 1.78 at cell thickness 9 µm.

To 85% by weight of the composition, 15% by weight of 4-(trans-4-(4-fluorobutyl)cyclohexyl)- 4'-(trans-4-butylcyclohexyl)biphenyl (compound No. 1) was mixed to obtain a nematic liquid crystal composition. The values of physical properties of this liquid crystal composition is as follows.

NI: 98.6, $\Delta \epsilon$: 9.9, $\Delta n$: 0.141, $\eta$: 33.5, $V_{10}$: 1.94 at cell thickness 8.7 µm.

Although the composition had been left at −20° C. in a freezer, no crystal were found in over 60 days.

EXAMPLE 8 (use example 2)

The same procedure as in Example 7 was repeated except that 4-(trans-4-(4-fluorobutyl)cyclohexyl)-4'-(trans-4-butylcyclohexyl)biphenyl (compound No. 1) was changed to 4-(trans-4-(5-fluoropentyl)cyclohexyl)-4'-(trans-4-ethenylcyclohexyl)biphenyl (compound No. 15). The values of physical properties of this liquid crystal composition are as follows.

NI: 99.8, $\Delta \epsilon$: 9.7, $\Delta n$: 0.143, 7) : 33.1, $V_{10}$: 1.98 at cell thickness 8.7 µm.

Although the composition had been left at −20° C. in a freezer, no crystals were found in over 60 days.

EXAMPLE 9 (use example 3)

The values of physical properties of the liquid crystal composition of composition example 23 are as follows.

NI: 96.6, $\Delta \epsilon$: 7.1, $\Delta n$: 0.162, $\eta$:17.0, $V_{10}$: 2.10.

EXAMPLE 10 (use example 4)

The values of physical properties of the liquid crystal composition of composition example 24 are as follows.

NI: 93.2, $\Delta \epsilon$: 8.7, $\Delta n$ : 0.149, $\eta$: 19.8, $V_{10}$: 1.99.

EXAMPLE 11 (use example 5)

The values of physical properties of the liquid crystal composition of composition example 25 are as follows.

NI: 97.7, $\Delta \epsilon$: 30.9, $\Delta n$: 0.147, $\eta$: 89.1, $V_{10}$: 0.86.

EXAMPLE 12 (use example 6)

The values of physical properties of the liquid crystal composition of composition example 26 are as follows.

NI: 103.6, $\Delta \epsilon$: 6.4, $\Delta n$ : 0.198, $\eta$: 39.5, $V_{10}$: 2.28.

EXAMPLE 13 (use example 7)

The values of physical properties of the liquid crystal composition of composition example 27 are as follows.

NI: 72.3, $\Delta \epsilon$: 11.5, $\Delta n$: 0.122, $\eta$: 40.9, $V_{10}$: 1.30.

EXAMPLE 14 (use example 8)

The values of physical properties of the liquid crystal composition of composition example 28 are as follows.

NI: 84.7, $\Delta \epsilon$: 8.1, $\Delta n$: 0.141, $\eta$: 20.0, $V_{10}$: 1.75.

EXAMPLE 15 (use example 9)

The values of physical properties of the liquid crystal composition of composition example 29 are as follows.

NI: 84.6, $\Delta$: 23.5, $\Delta n$: 0.118, $\eta$: 39.0, $V_{10}$: 0.99.

EXAMPLE 16 (use example 10)

The values of physical properties of the liquid crystal composition of composition example 30 are as follows.

NI: 93.6, $\Delta \epsilon$: 28.2, $\Delta n$ : 0.140, $\eta$: 41.6, $V_{10}$:1.00.

EXAMPLE 17 (use example 11)

The values of physical properties of the liquid crystal composition of composition example 31 are as follows.

NI: 68.1, $\Delta\epsilon$: 9.9, $\Delta n$ : 0.115, $\eta$: 28.8, $V_{10}$: 1.36.

EXAMPLE 18 (use example 12)

The values of physical properties of the liquid crystal composition of composition example 32 are as follows.

NI: 76.3, $\Delta\epsilon$: 6.5, $\Delta n$ : 0.164, $\eta$: 24.3, $V_{10}$: 1.78.

EXAMPLE 19 (use example 13)

The values of physical properties of the liquid crystal composition of composition example 33 are as follows.

NI: 106.7, $\Delta \epsilon$: 5.0, $\Delta n$ : 0.097, $\eta$: 27.6, $V_{10}$: 2.22.

EXAMPLE 20 (use example 14)

The values of physical properties of the liquid crystal composition of composition example 34 are as follows.

NI:96.4, $\Delta \epsilon$:3.2, $\Delta n$:0.096, $\eta$:22.5, $V_{10}$:2.69.

EXAMPLE 21 (use example 15)

The values of physical properties of the liquid crystal composition of composition example 35 are as follows.

NI: 93.4, $\Delta \epsilon$: 5.7, $\Delta n$ : 0.120, $\eta$: 27.6, $V_{10}$: 2.00.

EXAMPLE 22 (use example 16)

The values of physical properties of the liquid crystal composition of composition example 36 are as follows.

NI: 83.0, $\Delta \epsilon$: 8.4, $\Delta n$ 0.090, $\eta$: 29.9, $V_{10}$:1.60.

EXAMPLE 23 (use example 17)

The values of physical properties of the liquid crystal composition of composition example 37 are as follows.

NI: 94.7, $\Delta \epsilon$: 4.8, $\Delta n$: 0.125, $\eta$:22.4, $V_{10}$: 2.34.

EXAMPLE 24 (use example 18)

The values of physical properties of the liquid crystal composition of composition example 38 are as follows.

NI: 99.3, $\Delta\epsilon$ : 8.9, $\Delta n$ : 0.116, $\eta$:35.2, $V_{10}$:1.77.

EXAMPLE 25 (use example 19)

The values of physical properties of the liquid crystal composition of composition example 39 are as follows.

NI: 89.4, $\Delta \epsilon$: 4.5, $\Delta n$ : 0.093, $\eta$:15.8, $V_{10}$: 2.40.

EXAMPLE 26 (use example 20)

The values of physical properties of the liquid crystal composition of composition example 40 are as follows.

NI: 81.1, $\Delta \epsilon$: 8.2, $\Delta n$: 0.095, $\eta$: 28.7, $V_{10}$:1.75.

EXAMPLE 27 (use example 21)

The values of physical properties of the liquid crystal composition of composition example 41 are as follows.

NI: 95.9, $\Delta \epsilon$: 7.3, $\Delta n$ : 0.134, $\eta$:35.3, $V_{10}$: 1.91.

Moreover, although the liquid crystal compositions in the above examples 9–27 had been left at −20° C. in a freezer, no crystal were found in over 60 days.

EXAMPLE 28 (use example 22)

To 85% by weight of mother liquid crystal composition (a) containing 3,4-difluoro-(trans-4-(trans-4-ethylcyclohexyl)cyclohexyl)benzene, 3,4-difluoro-(trans-4-(trans-4-propylcyclohexyl)cyclohexyl)benzene and 3,4-difluoro-(trans-4-(trans-4-pentylcyclohexyl)cyclohexyl) benzene, which are liquid crystal compounds of a fluorine type, at the same weight, 15% by weight of 4-(trans-4-(4-fluorobutyl)cyclohexyl)-4'-(trans-4-butylcyclohexyl) biphenyl (compound No. 1), or 4,4'-bis (trans-4-butylcyclohexyl)biphenyl for comparison, or 4-(trans-4-(trans-4-propylcyclohexyl)cyclohexyl)benzonitrile, respectively, was mixed to obtain nematic composition (b), (c) and (d).

The temperature change of voltage holding rates (%) of these liquid crystal compositions is measured and the results are shown in FIG. 1.

Furthermore, the vertical axis shows the voltage holding rate and the horizontal axis shows the temperature measured (° C.).

As shown in the figure, liquid crystal composition (b) of the present invention shows a high voltage holding rate in the region of measured temperatures. From the results, it is known that the composition can be used as a necessary liquid crystal composition for TFT.

COMPARISON EXAMPLE 1

The same procedure as in Example 7 was repeated except that 4-(trans-4-(4-fluorobutyl)cyclohexyl)-4'-(trans-4-butylcyclohexyl)biphenyl (compound No. 1) was changed to 4,4'-bis(trans-4-butylcyclohexyl)biphenyl which is a comparative compound having the same structure but not substited by fluorine. The values of physical properties of this liquid crystal composition are as follows.

NI: 98.8, $\Delta \epsilon$:9.6, $\Delta n$: 0.140, $\eta$:33.3, $V_{10}$: 2.00 at cell thickness 8.7 $\mu$m.

Although the composition had been left at −20° C. in a freezer, crystal were at 34 days.

From the results, compared the compounds of the present invention with the compounds of comparative examples, it is known that the lowering of transition temperatures of isotropic phases and the increase of viscosity are controlled to the same extent, but the compatibility of the former compound is more improved than the latter compound.

As described above, the compounds of the present invention have very excellent stability, and it can improve the compatibility with the other liquid crystal materials during a high transition temperature of the isotropic phase and low viscosity are held.

INDUSTRIAL APPLICABILITY

Accordingly, when the compounds of the present invention are used as constituents of liquid crystal compositions, such compounds have excellent compatibility with the other liquid crystal materials, and it is possible to provide new liquid crystal compounds having desired physical properties by selecting six rings, substituent groups and/or bonding groups of molecular-constituting elements.

What is claimed is:

1. A liquid crystalline compound which is represented by the formula (1):

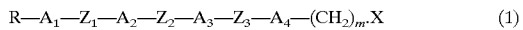

wherein R indicates H or an alkyl group having 1 to 10 carbon atoms (one or more methylene groups (—CH$_2$—) in the alkyl group may be replaced by —O—, —S—, —CO—; —CH=CH— or —C≡C—, but —O— or —S— are not continuous), m indicates an integer of 1 to 10; X indicates F, Cl, Br, I or OH; $A_1$, $A_2$, $A_3$, and $A_4$, each independently indicate a trans 1,4-cyclohexylene group, a 1,4-phenylene group with the proviso that when at least two of $A_1$, $A_2$, $A_3$, and $A_4$ are 1, 4-phenylene groups, one of $A_1$, $A_2$, $A_3$, and $A_4$ may have one hydrogen substituted by a fluorine atom, cyclohexenylenediyl group, a pyrimidine-2,5-diyl group, a pyridine-2,5-diyl group or a 1,3-dioxane-2,5-diyl group; $Z_1$, $Z_2$ and $Z_3$, each independently, indicate —(CH$_2$)$_2$— or a covalent bond, and at least two of $Z_1$, $Z_2$, and $Z_3$, indicated covalent bond; with the proviso that $A_2$ to $A_4$ are never all cyclohexylene groups.

2. A liquid crystalline compound according to claim 1, wherein X is F.

3. A liquid crystalline compound according to claim 1, wherein X is OH.

4. A liquid crystalline compound according to claim 2, wherein $Z_1$, $Z_2$ and $Z_3$ are covalent bonds.

5. A liquid crystalline compound according to claim 2, wherein $Z_1$ is —(CH$_2$)$_2$—.

6. A liquid crystalline compound according to claim 2, wherein $Z_2$ is —(CH$_2$)$_2$—.

7. A liquid crystalline compound according to claim 2, wherein $Z_3$ is —(CH$_2$)$_2$—.

8. A liquid crystalline compound according to claim 4, wherein both $A_1$ and $A_4$ are the trans 1,4-cyclohexylene group, and both $A_2$ and $A_3$ are the 1,4-phenylene group in which one or more hydrogen atoms on the ring may be substituted by a fluorine atom.

9. A liquid crystalline compound according to claim 4, wherein both $A_1$ and $A_2$ are the 1,4-phenylene group in which one or more hydrogen atoms on the ring may be substituted by a fluorine atom, and both $A_3$ and $A_4$ are the trans 1,4-cyclohexylene group.

10. A liquid crystalline compound according to claim 6, wherein both $A_1$ and $A_2$ are the 1,4-phenylene group in which one or more hydrogen atoms on the ring may be substituted by a fluorine atom, and both $A_3$ and $A_4$ are the trans 1,4-cyclohexylene group.

11. A liquid crystal composition comprising at least one of liquid crystalline compounds according to claim 1.

12. A liquid crystal composition, characterized in that it comprises a first constituent comprising at least one compound selected from the group consisting of the liquid crystalline compounds described in claim 1 and a second constituent comprising at least one compound selected from the group consisting of the compounds represented by formulas (2), (3) and (4):

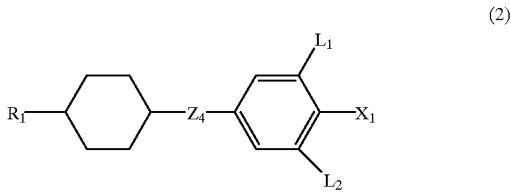

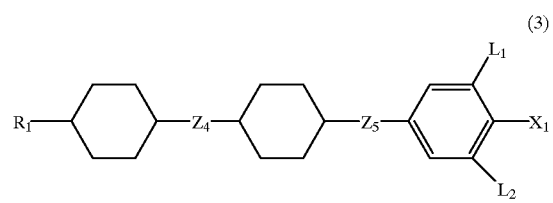

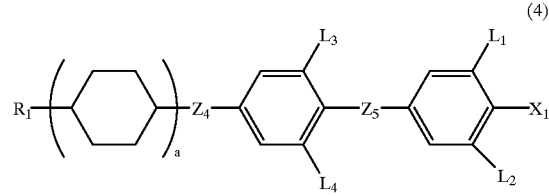

wherein $R_1$ indicates an alkyl group having 1 to 10 carbon atoms; $X_1$ indicates F, Cl, OCF$_3$, OCF$_2$H, CF$_2$H or CFH$_2$; $L_1$, $L_2$, $L_3$ and $L_4$, each independently indicate H or F; Z, and Z,, each independently, indicate —(CH$_2$)$_2$—, —CH=CH—, or a covalent bond, and a indicates 1 or 2.

13. A liquid crystal composition, characterized in that it comprises a first constituent comprising at least one compound selected from the group consisting of the liquid crystalline compounds described in claim 1 and a second constituent comprising at least one compound selected from the group consisting of the compounds represented by formulas (5), (6), (7), (8) and (9):

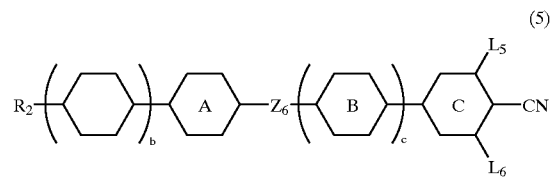

wherein $R_2$ indicates F, an alkyl group having 1 to 10 carbon atoms or an alkenyl group having 2 to 10 carbon atoms; any methylene group (—CH$_2$—) in the alkyl group or the alkenyl group may be replaced by an oxygen atom, but two or ore methylene groups are not continuously replaced by the oxygen atom; ring A indicates a trans-1,4-cyclohexylene group, a 1,4-phenylene group or a 1,3-dioxane-2,5-diyl group; ring B indicates a trans-1,4-cyclohexylene group, a 1,4-phenylene group or a pyrimidine-,5-diyl group; ring C indicates a trans-1,4-cyclohexylene group or a 1,4-phenylene group; $Z_6$ indicates —(CH$_2$)$_2$—, —COO— or a covalent bond; $L_5$ and $L_6$, each independently, indicate H or F; and b and c, each independently, indicate 0 or 1, (6)

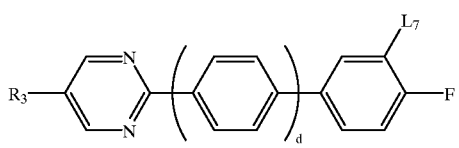

wherein $R_3$ indicates an alkyl group having 1 to 10 carbon atoms, $L_7$ indicates H or F; and d indicates 0 or 1, (7)

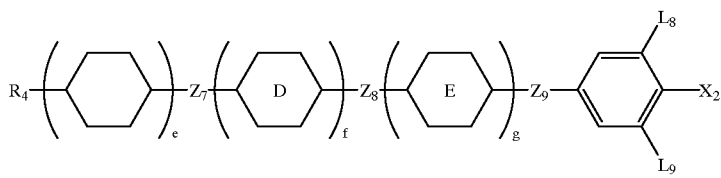

wherein $R_4$ indicates an alkyl group having 1 to 10 carbon atoms; ring D and ring E, each independently, indicate trans-1,4-cyclohexylene group or a 1,4-phenylene group; $Z_7$ and $Z_8$, each independently, indicate —COO— or a covalent bond; $Z_9$ indicates —COO— or —C≡C—; $L_8$ and $L_9$, each independently, indicate H or F; $X_2$ is F, $OCF_3$, $OCF_2H$, $CF_3$, $CF_2H$ or $CFH_2$; when $X_2$ indicates $OCF_3$, $OCF_2H$, $OCF_2H$, $CF_3$, $CF_2H$ or $CFH_2$, $L_8$ and $L_9$ both indicate H; e, f and g, each independently, indicates 0 or 1, (8)

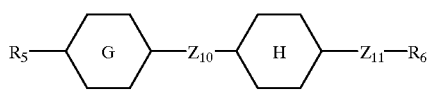

wherein $R_5$ and $R_6$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring G indicates a trans-1,4-cyclohexylene group, a 1,4-phenylene group or a pyrimidine-2,5-diyl group; ring H indicates a trans-1,4-cyclohexylene group or a 1,4-phenylene group; $Z_{10}$ indicates —$(CH_2)_2$—, —COO—, —CH=CH—C≡C— or a covalent bond; $Z_{11}$ indicates —COO— or a covalent bond, and (9)

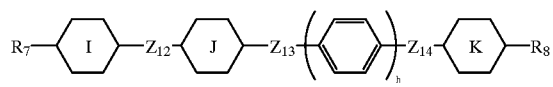

le;2qwherein $R_7$ and $R_8$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring I indicates a trans-1,4-cyclohexylene group, a 1,4-phenylene group or a pyrimidine-2,5-diyl group; ring J indicates a trans-1,4-cyclohexylene group, a 1,4-phenylene group in which one or more hydrogen atoms on the ring may be substituted by a fluoric atom, or a pyrimidine-2,5-dyl group; ring K indicates a trans-1,4-cyclohexylene group or a 1,4-phenylene group, $Z_{12}$ and $Z_{14}$, each independently, indicate —COO—, —$(CH_2)_2$— or a covalent bond, $Z_{13}$ indicates —CH=CH—, —C—C—, —COO— or a covalent bond; and h indicates 0 or 1.

14. A liquid crystal composition, characterized in that it comprises comprising at least one compound selected from the group consisting of the liquid crystalline compounds described in claim 1, and a second constituent comprising at least one compound selected from the group consisting of the compounds represented by formulas (2), (3) and (4):

(2)

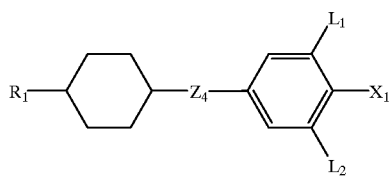

(3)

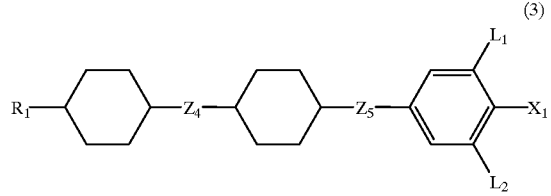

(4)

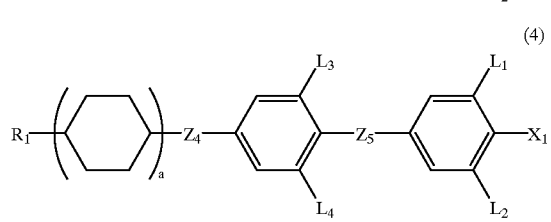

wherein $R_1$ indicates an alkyl group having 1 to 10 carbon atoms; $X_1$ indicates F, Cl, $OCF_3$, $OCF_2H$, $CF_2H$ or $CFH_2$; $L_1$, $L_2$, $L_3$ and $L_4$, each independently indicate H or F; $Z_4$ and $Z_5$, each independently, indicate —$(CH_2)_2$—, —CH=CH—, or a covalent bond, and a indicates 1 or 2, and at least one compound selected from the group consisting of the compounds represented by formulas (5), (6), (7), (8) and (9):

(5)

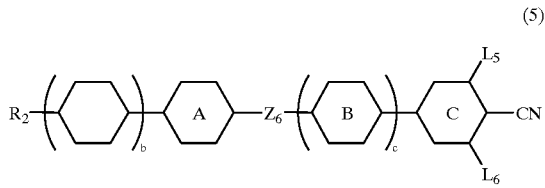

wherein $R_3$ indicates F, an alkyl group having 1 to 10 carbon atoms or an alkenyl group having 2 to 10 carbon atoms; any methylene group (—$CH_3$—) in the alkyl group or the alkenyl group may be replaced by an oxygen atom, but two or ore methylene groups are not continuously replaced by the oxygen atom; ring A indicates a trans-1,4-cyclohexylene group, a 1,4-phenylene group or a 1,3-dioxane-2,5-diyl group; ring B indicates a trans-1,4-cyclohexylene group, a 1,4-phenylene group or a pyrimidine-,5-diyl group; ring C indicates a trans-1,4-cyclohexylene group or a 1,4-phenylene group; $Z_6$ indicates —$(CH_2)_3$—, —COO— or a covalent bond; $L_5$ and $L_6$, each independently, indicate R or F; and b and c, each independently, indicate 0 or 1, (6)

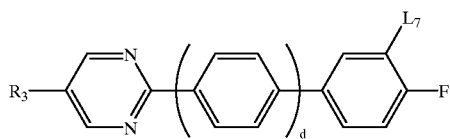

wherein $R_3$ indicates an alkyl group having 1 to 10 carbon atoms, $L_7$ indicates H or F; and d indicates 0 or 1, (7)

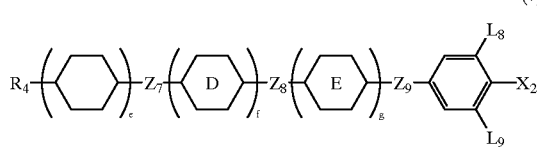

wherein $R_4$ indicates an alkyl group having 1 to 10 carbon atoms; ring D and ring E, each independently, indicate trans-1,4-cyclohexylene group or a 1,4-phenylene group; $Z_7$ and $Z_8$, each independently, indicate —COO— or a covalent bond; $Z_9$ indicates —COO— or —C≡C—; $L_8$ and $L_9$, each independently, indicate H or F; $X_2$ is F, $OCF_3$, $OCF_2H$, $CF_3$, $CF_3H$ or $CFH_2$; when $X_2$ indicates $OCF_3$, $OCF_2H$, $OCF_3H$, $CF_3$, $CF_3H$ or $CFH_2$, $L_8$ and $L_9$ both indicate H; e, f and g, each independently, indicates 0 or 1, (8)

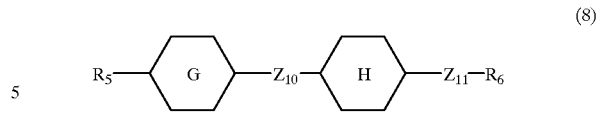

wherein $R_5$ and $R_6$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring G indicates a trans-1,4-cyclohexylene group, a 1,4-phenylene group or a pyrimidine-2,5-diyl group; ring H indicates a trans-1,4-cyclohexylene group or a 1,4-phenylene group; $Z_{10}$ indicates —$(CH_2)_2$—, —COO—, —CH=CH—C≡C— or a covalent bond; $Z_{14}$ indicates —COO— or a covalent bond, and (9)

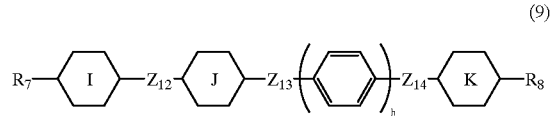

wherein $R_7$ and $R_8$, each independently, indicate an alkyl group having 1 to 10 carbon atoms or an alkenyl group having 2 to 10 carbon atoms, and in any case, any methylene group (—$CH_2$—) may be replaced by an oxygen atom (—O—), but two or more methylene groups are not continuously replaced by an oxygen atom; ring I indicates a trans-1,4-cyclohexylene group, a 1,4-phenylene group or a pyrimidine-2,5-diyl group; ring J indicates a trans-1,4-cyclohexylene group, a 1,4-phenylene group in which one or more hydrogen atoms on the ring may be substituted by a fluoric atom, or a pyrimidine-2,5-dyl group; ring K indicates a trans-1,4-cyclohexylene group or a 1,4-phenylene group, $Z_{12}$ and $Z_{14}$, each independently, indicate —COO—, —$(CH_2)_2$— or a covalent bond, $Z_{13}$ indicates —CH=CH—, —C≡C—, —COO— or a covalent bond; and h indicates 0 or 1.

15. A liquid crystal display device comprising the liquid crystal compositions described in claim 11.

16. A liquid crystal display device comprising the liquid crystal compositions described in claim 12.

17. A liquid crystal display device comprising the liquid crystal compositions described in claim 13.

18. A liquid crystal display device comprising the liquid crystal compositions described in claim 14.

* * * * *